United States Patent
Chen et al.

(10) Patent No.: US 9,422,517 B2
(45) Date of Patent: Aug. 23, 2016

(54) MICROSCALE AND NANOSCALE STRUCTURES FOR MANIPULATING PARTICLES

(75) Inventors: Grace Chen, Cambridge, MA (US); Fabio Fachin, Cambridge, MA (US); Mehmet Toner, Wellesley, MA (US); Brian Wardle, Lexington, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 168 days.

(21) Appl. No.: 13/812,934

(22) PCT Filed: Jul. 29, 2011

(86) PCT No.: PCT/US2011/045880
§ 371 (c)(1),
(2), (4) Date: Oct. 1, 2013

(87) PCT Pub. No.: WO2012/016136
PCT Pub. Date: Feb. 2, 2012

(65) Prior Publication Data
US 2014/0030788 A1   Jan. 30, 2014

Related U.S. Application Data

(60) Provisional application No. 61/369,608, filed on Jul. 30, 2010, provisional application No. 61/401,663, filed on Aug. 16, 2010.

(51) Int. Cl.
*B07B 9/00* (2006.01)
*C12M 1/12* (2006.01)
(Continued)

(52) U.S. Cl.
CPC .......... *C12M 25/16* (2013.01); *B01L 3/502707* (2013.01); *B01L 3/502746* (2013.01);
(Continued)

(58) Field of Classification Search
CPC ................. G01N 2015/0038; G01N 33/48721
USPC .................................................. 209/155, 156
See application file for complete search history.

(56) References Cited

U.S. PATENT DOCUMENTS 5,443,727 A * 8/1995 Gagnon ........................ 210/490
5,837,115 A   11/1998 Austin et al.
(Continued)

FOREIGN PATENT DOCUMENTS

WO   2004/029221   4/2004
WO   2004/113877   12/2004
(Continued)

OTHER PUBLICATIONS

International Search Report and Written Opinion mailed Mar. 27, 2012 in International Application No. PCT/US2011/045880, 13 pgs.
(Continued)

*Primary Examiner* — Howard Sanders
(74) *Attorney, Agent, or Firm* — Fish & Richardson P.C.

(57) ABSTRACT

The devices and systems described herein include one or more fluid paths, e.g., channels, and one or more selectively permeable obstacles arranged in the fluid path(s), each including a plurality of aligned nanostructures, e.g., nanotubes or nanorods, defining an outer surface of the obstacle and an internal network of voids. The obstacle(s) can further include binding moieties applied to the outer surface and/or to the surfaces of the individual nanostructures within the obstacle(s). The devices can be manufactured by forming the dense groupings of nanostructures to extend outwards and upwards from a substrate; forming a fluidic channel, bonding the fluidic channel to the substrate; and optionally applying binding moieties to the obstacles. The devices can be used to manipulate cells within fluid samples.

20 Claims, 33 Drawing Sheets

(51) Int. Cl.
  *B01L 3/00*   (2006.01)
  *G01N 15/14*  (2006.01)
(52) U.S. Cl.
  CPC ...... *B01L3/502761* (2013.01); *G01N 15/1404* (2013.01); *B01L 2200/0652* (2013.01); *B01L 2200/0668* (2013.01); *B01L 2300/0896* (2013.01); *B01L 2400/086* (2013.01); *G01N 2015/1413* (2013.01)

(56) References Cited

U.S. PATENT DOCUMENTS

| | | | |
|---|---|---|---|
| 7,279,134 B2* | 10/2007 | Chan et al. | 422/503 |
| 7,290,667 B1 | 11/2007 | Bakajin et al. | |
| 2004/0053422 A1 | 3/2004 | Chan et al. | |
| 2004/0144651 A1 | 7/2004 | Huang et al. | |
| 2004/0262636 A1 | 12/2004 | Yang et al. | |
| 2005/0255014 A1* | 11/2005 | Glover et al. | 422/190 |
| 2006/0134599 A1 | 6/2006 | Toner et al. | |
| 2007/0026413 A1 | 2/2007 | Toner et al. | |
| 2007/0264675 A1 | 11/2007 | Toner et al. | |
| 2008/0044911 A1* | 2/2008 | Bock et al. | 436/63 |
| 2008/0075954 A1 | 3/2008 | Wardle et al. | |
| 2009/0311166 A1 | 12/2009 | Hart et al. | |
| 2010/0255303 A1 | 10/2010 | Wardle et al. | |
| 2014/0079601 A1* | 3/2014 | Rubner | B01L 3/502707 422/501 |

FOREIGN PATENT DOCUMENTS

| | | |
|---|---|---|
| WO | 2007/136755 | 11/2007 |
| WO | 2009-029218 | 3/2009 |
| WO | 2010/120273 | 10/2010 |
| WO | 2011/014258 | 2/2011 |

OTHER PUBLICATIONS

Bedewy et al., "Collective Mechanism for the Evolution and Self-Termination of Vertically Aligned Carbon Nanotube Growth," J. Phys. Chem. C, 113(48):20576-20582 (2009).

Garcia et al., "Fabrication and Nanocompression Testing of Aligned Carbon-Nanotube—Polymer Nanocomposites," Adv. Mater., 19:2151-2156 (2007).

Garcia et al., "Fabrication of composite microstructures by capillarity-driven wetting of aligned carbon nanotubes with polymers," Nanotechnology, 18(16), 165602 (11 pages) (2007).

Hart et al., "Rapid growth and flow-mediated nucleation of millimeter-scale aligned carbon nanotube structures from a thin-film catalyst," J. Phys. Chem. B, 110(16), 8250-8257 (Apr. 2006).

Huang et al., "Continuous Particle Separation Through Deterministic Lateral Displacement," Science, 304(5673), 987-990 (May 2004).

Wardle et al., "Fabrication and Characterization of Ultrahigh-Volume- Fraction Aligned Carbon Nanotube—Polymer Composites," Adv. Mater., 20(14), 2707-2714 (Jul. 2008).

* cited by examiner

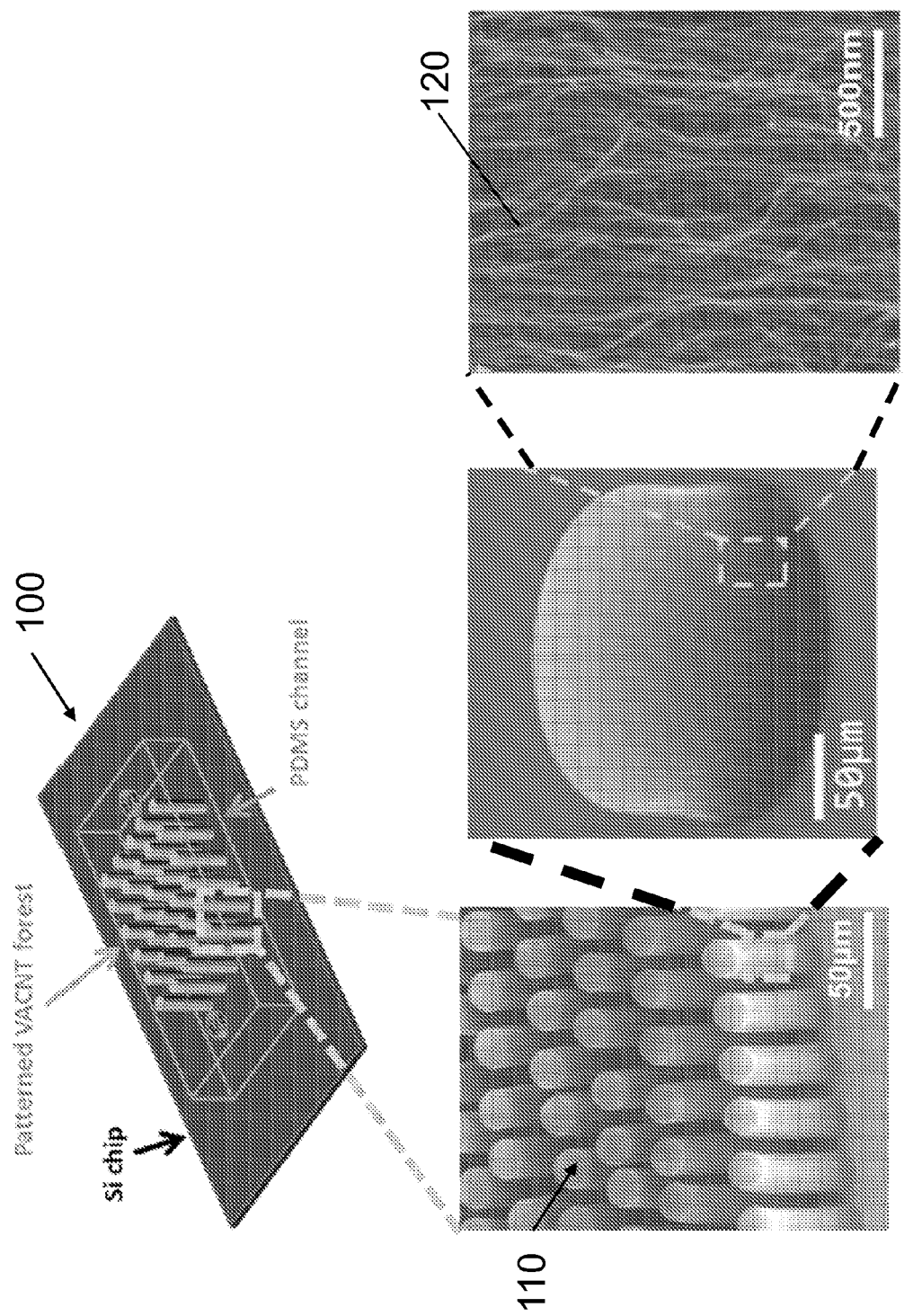

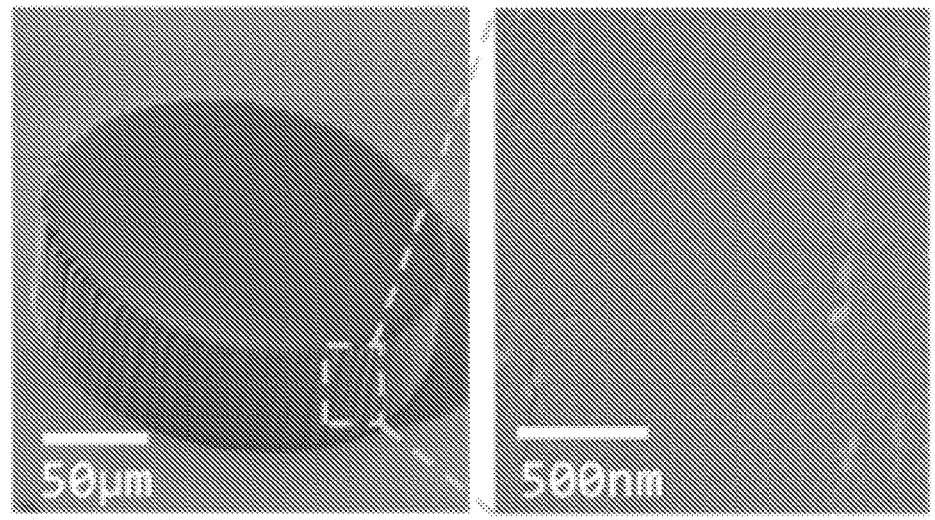
FIG. 3A  FIG. 3B
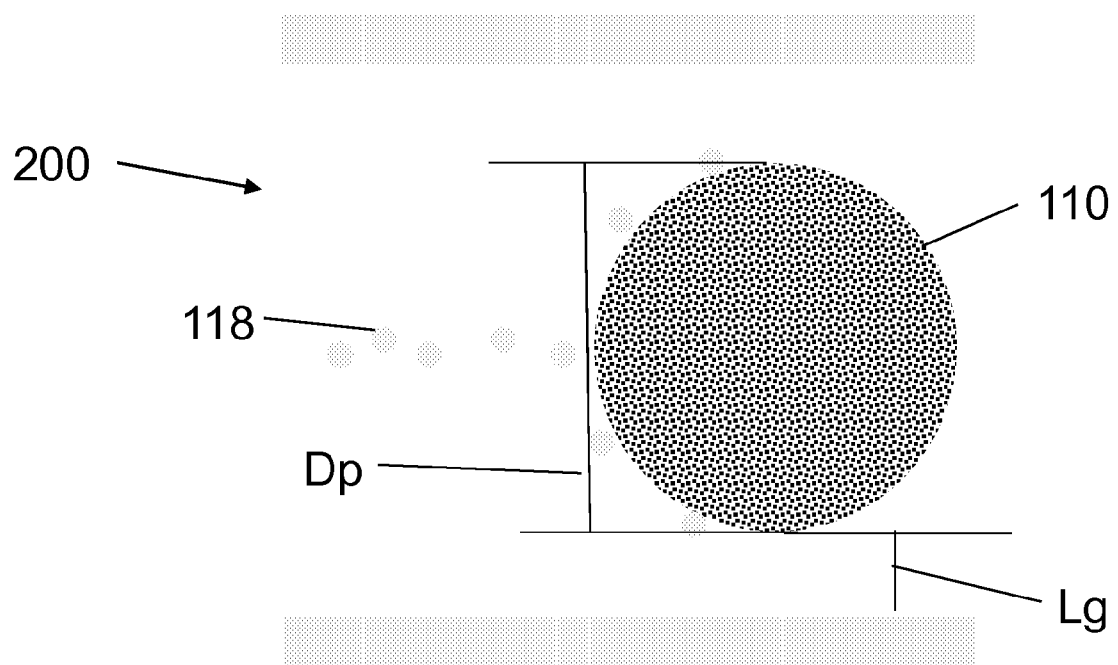
FIG. 4

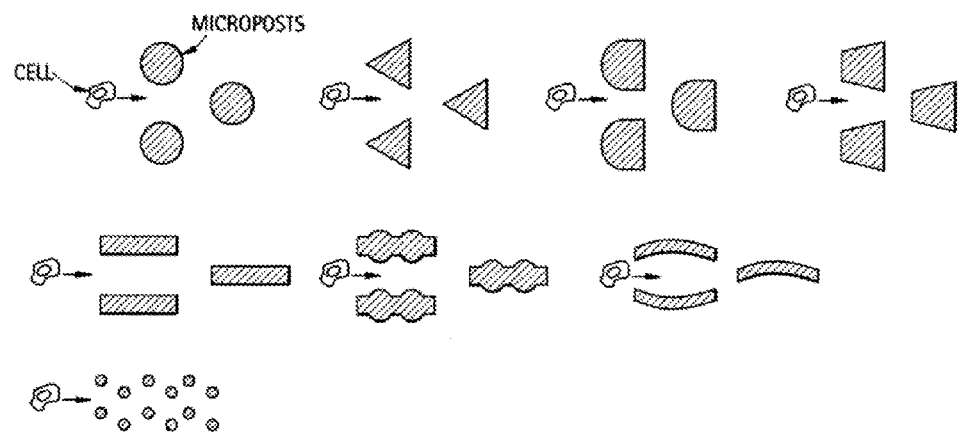
FIG. 6
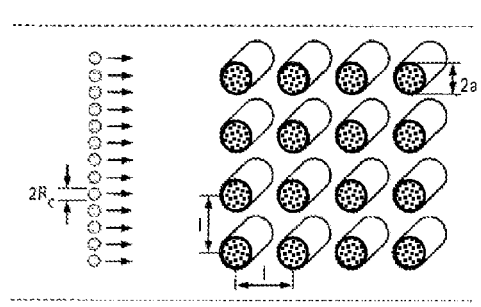     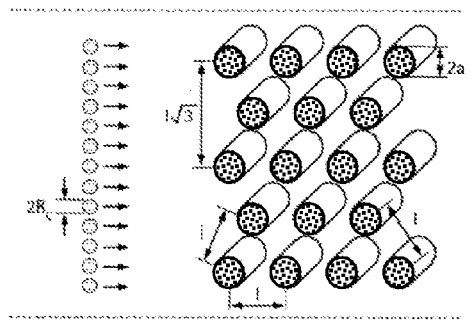
FIG. 7A     FIG. 7B

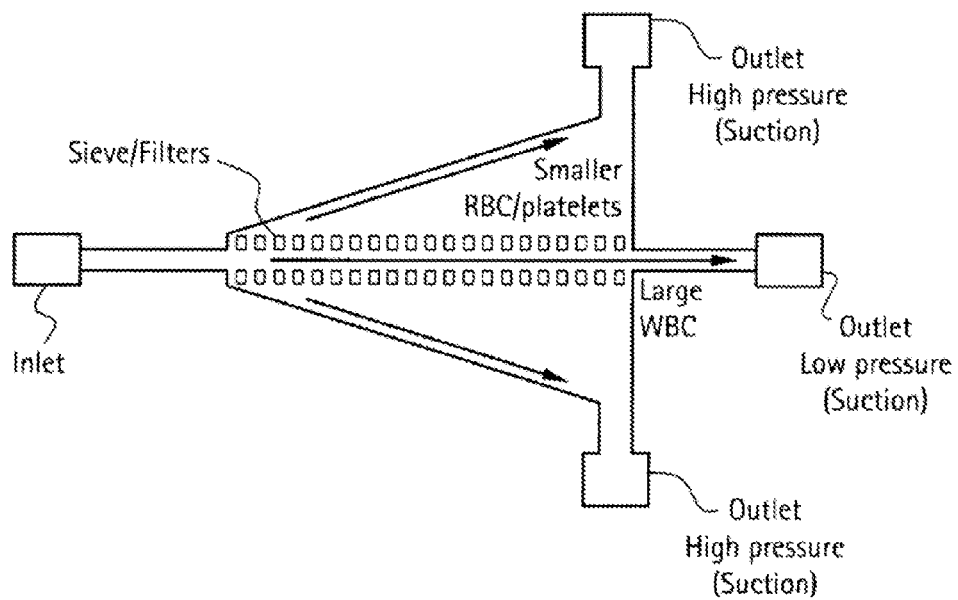
FIG. 13
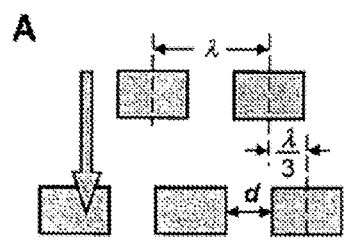
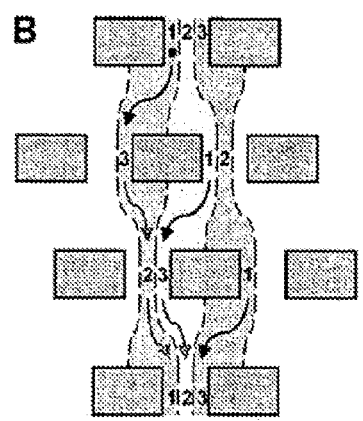
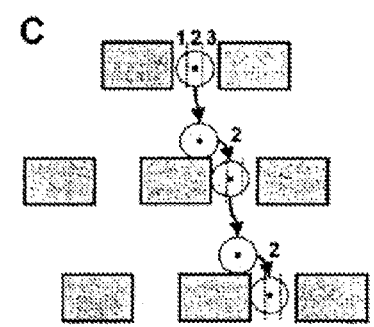
FIG. 14A     FIG. 14B     FIG. 14C

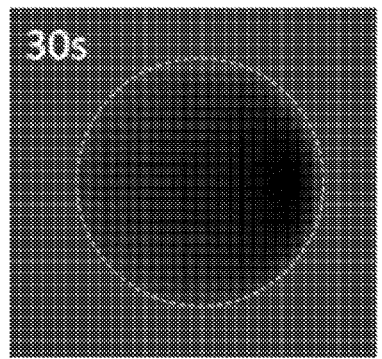
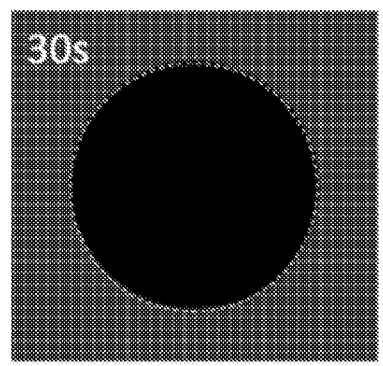
FIG. 28A  FIG. 28B
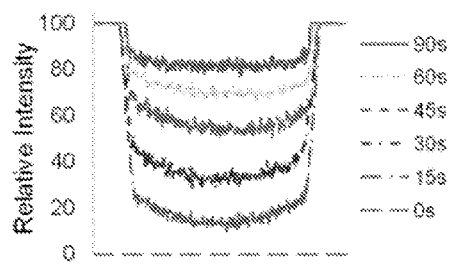
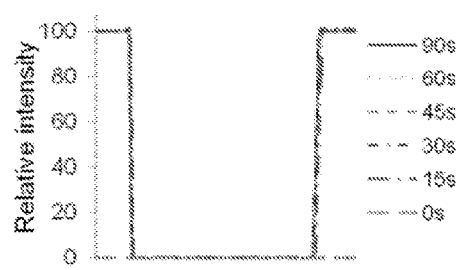
FIG. 29A  FIG. 29B
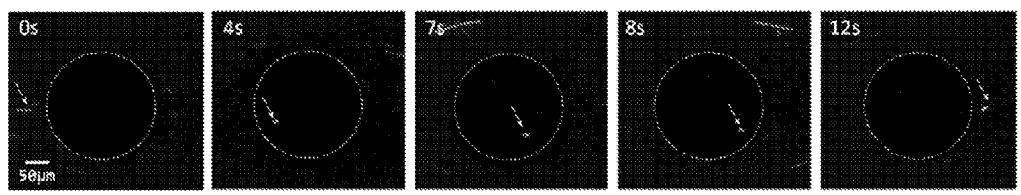
FIG. 30

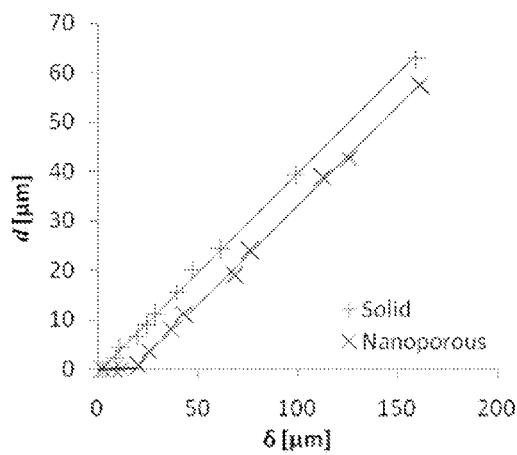
FIG. 35
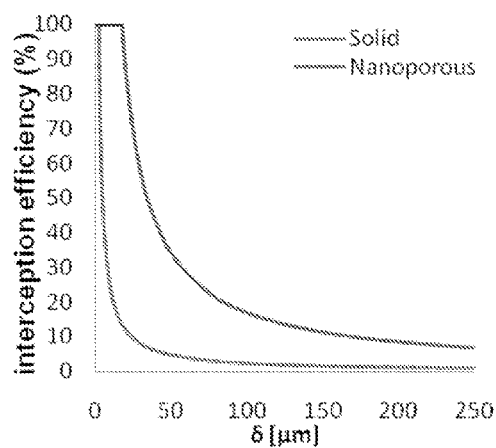
FIG. 36
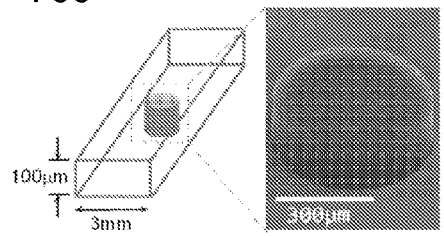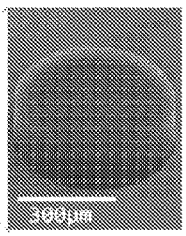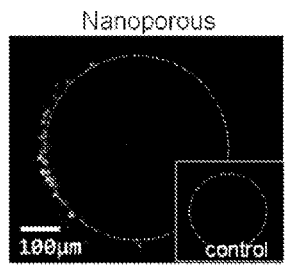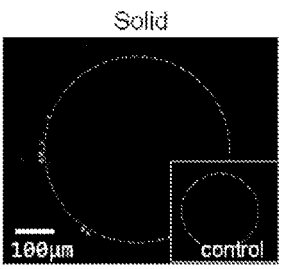
FIG. 37A  FIG. 37B  FIG. 37C  FIG. 37D
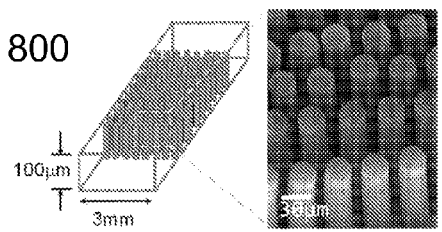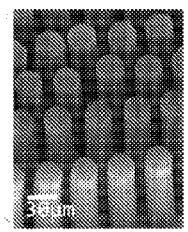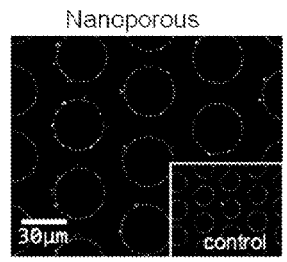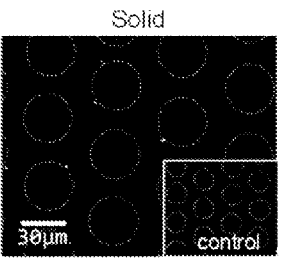
FIG. 38A  FIG. 38B  FIG. 38C  FIG. 38D

Definition of "Growth temperature" and "pre-treatment time" for CNT growth process Effect of preconditioning time on forest morphology Baseline +7min pre-treatment time

CNT walls

A

Asymmetrical airfoil

MICROSCALE AND NANOSCALE STRUCTURES FOR MANIPULATING PARTICLES

CLAIM OF PRIORITY

This application is a 35 U.S.C. §371 national phase application of International Application No. PCT/US2011/045880, filed on Jul. 29, 2011, which claims the benefit of U.S.Provisional Application Ser. No. 61/369,608, filed on Jul. 30, 2010, and U.S. Provisional Application Ser. No. 61/401,663, filed on Aug. 16, 2010, all of which are incorporated herein by reference in their entireties.

STATEMENT AS TO FEDERALLY SPONSORED RESEARCH

This invention was made with Government support under Grant Number EB002503 awarded by the National Institutes of Health. The Government has certain rights to this invention.

TECHNICAL FIELD

This invention relates to the manipulation of particles, e.g., biological particles, and more particularly to fluidic capture, separation, and concentration or enrichment of particles.

BACKGROUND

Most clinical diagnostics and basic research studies aimed at understanding the causes underlying disease require isolation of specific biomolecules or cells from complex samples such as blood, saliva, and cell culture supernatant. Sometimes such bioparticles of interest are present in the samples in very small quantities. This is the case, for example, of antigen-specific T-cells, circulating tumor cells, and HIV viral particles, which can be used, for example, for monitoring immune responses, cancer, and AIDS progression respectively.

Fluidic (macroscopic) and microfluidic devices can be used for detecting, capturing, separating, and enriching particles of many types that are suspended or dispersed in a fluid. In some cases, microfluidic devices include obstacles coated with binding moieties that selectively bind to specific bioparticles that contact surfaces of the obstacle. In some situations, the obstacles are formed from solid materials such as silicon, polymers, and glass. Such materials possess attributes including geometrical definability (e.g., using photolithography), and compatibility with both gas and liquid-phase chemical functionalization processes. Geometrical definability, e.g., in microfluidic applications, allows control of the fluid dynamics inside the channels. Selective functionalization of the structural features allows isolation and manipulation of specific particles. In addition, some of the materials, such as polydimethylsiloxane (PDMS), exhibit optical transparency, which allows on-line visual monitoring of the tests and simplifies bio-assay readout designs.

However, in such prior devices, fluid-boundary interactions at the surface of obstacles in the fluid path can have detrimental effects on the desired functions of these devices.

SUMMARY

The devices, systems, and methods described herein are based, at least in part, upon the discovery that particles, e.g., biological particles, of different cross-sectional dimensions can be manipulated, e.g., isolated, captured, enriched, by flowing the particles through a porous array of obstacles, where each obstacle is formed of multiple aligned nanostructures that render the obstacle substantially porous, e.g., nanoporous.

In some examples, the particles, e.g., biological particles, of different cross-sectional dimensions suspended in a fluid sample are flowed through the fluidic path formed in a device, e.g., a microfluidic device. The substantially porous obstacles, each of which is configured to manipulate the particles suspended in the fluid sample, are disposed as an array within the fluidic path. For example, the porous obstacles are arranged and fixed within the fluidic path formed in the device to capture, separate, concentrate, and enrich the particles.

Each obstacle can include multiple, generally aligned, e.g., vertically aligned, nanostructures, such as nanotubes or nanorods, e.g., carbon nanotubes or nanorods. The spacing between the multiple nanostructures renders each obstacle porous such that each obstacle has a high permeability. The array of obstacles can be disposed within the fluidic path (e.g., a microfluidic channel) in particular arrangements and configurations to mechanically manipulate the particles in the fluid sample. Alternatively, or in addition, the obstacles can be functionalized to chemically manipulate the particles. For example, the array of obstacles can isolate, enrich, capture, separate, and/or analyze the biological particles from other particles or from the fluid sample in which the biological particles are suspended or dispersed by either mechanically capturing the particles or chemically binding the particles or both.

In certain embodiments, the permeable nanotube and/or nanorod structures in each obstacle can be created using methods such as photolithography and chemical vapor deposition to produce a dense aggregation of carbon nanotubes in the form of a specific obstacle such as a post, column, or barrier wall. Multiple nanostructures can be provided such that their longitudinal axes are substantially aligned. For example, in some cases, the nanostructures can be fabricated by growing, e.g., uniformly growing, the nanostructures on the surface of the fluidic path defined in a substrate, such that the long axes lie in the fluidic path and are aligned and non-parallel, e.g., orthogonal, to the substrate surface. The nanostructures can be, in some instances, substantially perpendicular to the substrate surface. In one set of embodiments, a force or forces with a component or components normal to the long or longitudinal axes of the nanostructures is applied to the substantially aligned nanostructures. The application of a force can result in a material comprising a relatively high volume fraction or mass density of nanostructures, but still with a high level, e.g., anywhere from 10 or 12 percent up to 50, 75, 80, 90, 92, 95, 97, 98, or 99 percent or more, of total void space within a given obstacle. In some instances, the application of a force may result in a material comprising relatively closely-spaced (e.g., densely packed) nanostructures, with a correspondingly lower total void space.

In some embodiments, and as shown in figures described herein, each obstacle can be hollow, and the multiple aligned nanostructures in each obstacle can form the side, top, or side and top walls, or bottom walls, of the obstacles. Similarly, if the array of obstacles is in the form of one or more larger barriers, e.g., elongated barriers, then each obstacle in such barriers can also be hollow, and the nanostructures then form the side, top, or side and top (or bottom) walls of the barriers.

In particular, the obstacles have sufficient structural integrity to withstand the forces applied by the flowing fluid sample without collapsing. In many cases it is important that the obstacles maintain their overall defined shape (geometry, orientation, and nanostructured morphology) to properly affect and manipulate the fluid streamlines to advantageously manipulate particles. It has been observed that, unlike capillary-force induced collapse of nanostructured obstacles by fluids known in the literature, the obstacles described herein substantially maintain their overall shape and location. Without being bound to any theories, physical and geometric variables and also fluid flow direction and device processing all play a role in maintaining obstacle shape and location. For example, the bending stiffness of an obstacle is one characteristic that affects the obstacle's ability to maintain shape when wet by a fluid flow field. This property is affected by the height of the obstacle relative to its areal or cross-sectional dimensions. Another example is the role of the fluid being introduced generally perpendicular to the long axis of the nanostructures, such that the fluid enters the aligned nanostructures primarily diffusively rather than through strong capillary action in the case when the fluid is introduced into the ends of an aligned nanostructure obstacle.

Further, structural properties of the obstacles, for example, the diameter, height, average spacing between (or volume or mass density of) the nanotubes forming the obstacles, can be controlled and tailored to suit specific applications. In addition, the design and arrangement of the nanostructures causes an interaction between the fluid streamlines and the surface of each obstacle that allows advantageously manipulating particles, e.g., to enhance the number and likelihood of desired contacts or interactions between the particles and the obstacles in the fluid path, or conversely, to decrease the number and likelihood of undesired contacts or interactions between the particles and the obstacles in the fluid path.

The nanotube or nanorod obstacles can have very high permeability and excellent structural and other physical properties. Permeability of the nanostructure-containing obstacles can be manipulated by a variety of means, including mechanical means, modifying aspects of the carbon nanotube (CNT) synthesis and post-growth manipulating processes, conformal coatings, etc. The devices and systems that include these devices thus provide highly efficient manipulation, e.g., capture, isolation, separation, and/or concentration, of different types of particles across multiple, e.g., two, three, or four, orders of magnitude of sizes, from subnanometers to multiple micrometers or even centimeters.

Once the obstacles made of nanostructures, e.g., carbon nanotubes, are arranged inside the fluidic path, e.g., a microfluidic channel, the fluid sample can be introduced into the channel, e.g., by pressure driven flow. Various chemical and/or biological binding moieties can be used to functionalize the nanostructures to specifically bind to particular particles of interest, e.g., specific cells or biomolecules. In some embodiments, one or more detergents, proteins, or other agents are used to coat the nanotubes and/or the nanotube obstacles to inhibit non-specific binding of particles. The new devices can be easily adapted for highly efficient and specific isolation, enrichment, detection, capture, separation, and/or analysis of various types and sizes of particles.

In general, in one aspect the invention features methods of manipulating particles in fluid samples. The methods include (a) introducing a fluid sample containing particles of a first type into a fluidic device comprising: (i) a fluid path; and (ii) one or more obstacles, each obstacle comprising a plurality of aligned nanostructures and having an obstacle outer boundary that occupies a defined space in the fluid path; wherein the one or more obstacles are fixedly arranged within the fluid path such that some streamlines within the fluid path pass around the obstacle outer boundaries and some streamlines within the fluid path pass through the obstacle outer boundaries and into a network of spaces within the obstacle between the nanostructures, and wherein the nanostructures within the obstacles alter a flow field near the outer surface of the obstacles compared to obstacles of the same defined space made of a material through which fluid does not flow. In some embodiments, the fluid sample can be flowed through the fluid path such that a smaller or greater number of the particles contacts the obstacles, relative to the number that would contact the obstacles of the same defined space made of a material through which fluid does not flow. In some embodiments, the fluid sample can be flowed through the fluid path at a flow rate that (i) maintains a geometry of the one or more obstacles such that a space occupied by a substantial number, e.g., more than 50, 60, 70, 75, 80, 85, 90, 95, or 99 percent, of the obstacles after the fluid sample is flowed through the fluid path is substantially the same as the defined space occupied by the same obstacle before the sample is flowed through the fluid path, and/or (ii) enables the capture of at least some of the particles of the first type in the fluid sample or the selective separation or concentration of at least some of the particles of the first type from the fluid sample or from particles of a second type. In these methods, obstacle geometry can be measured as described herein, e.g., by taking a scanning electron microscope image and quantifying changes in features such as the outer space occupied by the obstacle. The nanostructure geometry can be measured using a transmission electron microscope image and measuring changes in features.

In some embodiments, the method comprises introducing a liquid sample into a fluidic device comprising a fluid path and one or more obstacles comprising a plurality of aligned nanostructures with an aspect ratio of at least about 100 and having an obstacle outer boundary, the obstacles occupying a defined space in the fluid path; and flowing the liquid sample through the fluid path in a direction substantially perpendicular to the longitudinal axes of the nanostructures within the obstacles such that a geometry of the one or more obstacles is maintained such that a space occupied by a substantial number of the obstacles after the liquid sample is flowed through the fluid path is substantially the same as the defined space occupied by the same obstacle before the liquid sample is flowed through the fluid path.

In these methods, flowing the fluid sample through the fluid path can include flowing the fluid sample in a direction generally perpendicular to an average longitudinal axis of the aligned nanostructures.

In certain embodiments, maintaining the geometry of the one or more obstacles to be substantially the same includes maintaining a similarity of the outer surface geometry of the obstacles of at least 90 percent before and after the fluid sample is flowed through the fluid path.

In some of the methods, the nanostructures within the obstacles can alter the flow field by reducing fluid boundary layer effects near the outer surface of the obstacles compared to obstacles of the same defined space made of a solid material to enable more streamlines to contact the outer surface of the obstacles as compared to obstacles of the same defined space made of a solid material.

When particles of the first type are captured, the capture efficiency in the fluidic device can be at least five-fold, e.g., six-fold or seven-fold greater than the capture efficiency of a fluidic device of the same geometry in which the one or more obstacles occupy the same defined space, but are composed of a solid material instead of nanostructures. In some embodiments, some or all of the one or more obstacles can comprise a total void space of less than or equal to about 99 percent.

In some embodiments, the fluidic devices can include an array of multiple obstacles defining a network of gaps between the obstacles. In these arrays, the average gap size between the obstacles in the array can be larger than an average hydrodynamic size of the first type of particle, e.g., the average gap size between the obstacles can be between 20 and 100 microns in size.

In these methods, an average space between the nanostructures within the obstacles can be smaller than an average hydrodynamic size of the first type of particle and larger than an average hydrodynamic size of the second type of particle.

In certain embodiments, the one or more obstacles can include at least on their outer surface first binding moieties that specifically bind to the first type of particles, and/or the nanostructures within the obstacles can include on their surfaces second binding moieties that bind specifically to particles of the second type.

In one embodiment, the one or more obstacles are in the form of two barriers including a gap between the two barriers that is larger than an average hydrodynamic size of the first type of particle, and wherein an average size of the void spaces between the nanostructures in the barriers is smaller than an average hydrodynamic size of the first type of particle and larger than an average hydrodynamic size of the second type of particle, such that the fluidic device enables separation of the second type of particles from the first type of particle.

In another embodiment, the fluidic device has a channel with opposing first and second barriers on either side of the fluid path, wherein the one or more obstacles comprise a third barrier that extends partially across the channel from the first barrier towards the second barrier of the channel, and wherein an average size of the void spaces between the nanostructures in the third barrier is smaller than an average hydrodynamic size of the first type of particle, and larger than an average hydrodynamic size of a second type of particle, such that the fluidic device enables concentration of the first type of particle from the fluid sample.

In the new methods, the first type of particles can be, for example, epithelial cells, cancer cells, bone marrow cells, fetal cells, progenitor cells, stem cells, foam cells, mesenchymal cells, immune system cells, endothelial cells, endometrial cells, connective tissue cells, trophoblasts, bacteria, fungi, platelets, or pathogens. The second type of particles can be, for example, viruses, viral particles, exosomes, microvesicles, nucleic acids, proteins, lipids, and synthetic nanoparticles.

In these methods, the first type of particles can have a hydrodynamic size of about 0.5 to 50 microns, and the second type of particles can have a hydrodynamic size of about 1 to 1000 nanometers.

In some embodiments, flowing a fluid sample through the network of gaps produces fluid forces that direct particles having a hydrodynamic size above the gap size in a first direction and particles having a hydrodynamic size below the gap size in a second direction different than the first direction. For example, the array of obstacles can be configured to direct particles having a hydrodynamic size greater than 12 microns (e.g., greater than 14 microns or greater than 16 microns) in the first direction.

In some embodiments, the fluidic device includes a channel with opposing first and second walls on either side of the fluid path and the obstacles of the array are arranged within the channel between the first wall and the second wall. In certain embodiments the obstacles can have a generally circular or ellipsoid cross-section and the size of the gaps between obstacles is at least 50% larger than a hydrodynamic size of particles of the first type.

In various embodiments, one or more of the obstacles are hollow, and the plurality of aligned nanostructures comprise side, top, or both side and top, walls of the obstacles.

In another aspect, the invention features fluidic devices for manipulating particles. These device include a substrate that defines a fluid path; and one or more obstacles, each obstacle comprising a plurality of aligned nanostructures and having an obstacle outer boundary that occupies a defined space in the fluid path. In some embodiments, the one or more obstacles are fixedly arranged within the fluid path such that some streamlines within the fluid path pass around the obstacle outer boundaries and some streamlines within the fluid path pass through the obstacle outer boundaries and into a network of spaces within the obstacle between the nanostructures, and wherein the nanostructures within the obstacles alter a flow field near the outer surface of the obstacles compared to obstacles of the same defined space made of a material through which fluid does not flow. In some embodiments, the fluidic device is configured such that, when flowing a fluid sample through the fluid path a geometry of the one or more obstacles is maintained such that a space occupied by a substantial number of the obstacles after the fluid sample is flowed through the fluid path is substantially the same as the defined space occupied by the same obstacle before the sample is flowed through the fluid path. In some embodiments, the device is configured such that it enables the capture of at least some of particles of a first type in the fluid sample or the selective separation or concentration of at least some of the particles of the first type from the fluid sample or from particles of a second type.

In some embodiments, the fluidic device comprises a substrate, an enclosed fluid path defined in the substrate, and a plurality of aligned nanostructures attached to two opposed boundaries of the enclosed fluid path configured such that fluid transported through the fluid path travels substantially perpendicularly to the longitudinal axes of the aligned nanostructures.

In these devices, the obstacles can form an array, e.g., of evenly spaced obstacles, defining a network of gaps between the obstacles. The fluidic devices can be designed to provide a particle capture efficiency that is at least five-fold greater than the capture efficiency of the same fluidic device in which the one or more obstacles are composed of a solid material instead of the nanostructures. The one or more obstacles can each have a total void space of less than or equal to about 99 percent, and an average spacing between the obstacles in the array can be larger than an average hydrodynamic size of the first type of particle, e.g., the average spacing between the obstacles can be between 20 and 100 microns in size. In certain embodiments an average space between the aligned nanostructures within the obstacles can be smaller than an average hydrodynamic size of the first type of particle and larger than an average hydrodynamic size of a second type of particle.

In certain embodiments of these devices, the one or more obstacles can include, at least on their outer surface, first binding moieties that specifically bind to the first type of particles. In addition, or in the alternative, the nanostructures within the obstacles can include, on their surfaces, second binding moieties that bind specifically to particles of a second type.

In these devices, maintaining the geometry of the one or more obstacles to be substantially the same can include maintaining a similarity of the outer surface geometry of each of the obstacles of at least 90 percent before and after the fluid sample is flowed through the fluid path.

In some embodiments of these devices, the one or more obstacles can be in the form of two barriers including a gap between the two barriers that is larger than an average hydrodynamic size of the first type of particle, and wherein an average size of the void spaces between the nanostructures in the barriers is smaller than an average hydrodynamic size of the first type of particle and larger than an average hydrodynamic size of the second type of particle, such that the fluidic device enables separation of the second type of particles from the first type of particle.

Other of these devices can include a channel with opposing first and second barriers on either side of the fluid path, wherein the one or more obstacles comprise a third barrier that extends partially across the channel from the first barrier towards the second barrier of the channel, and wherein an average size of the spaces between the nanostructures in the third barrier is smaller than an average hydrodynamic size of the first type of particle, and larger than an average hydrodynamic size of a second type of particle, such that the fluidic device enables concentration of the first type of particle from the fluid sample.

In any of these devices, one or more of the obstacles can be hollow, and the side, top, or both side and top walls of the hollow obstacles can comprise the plurality of aligned nanostructures.

In another aspect, the invention also features fluid manipulation systems that include one or more of the fluidic devices described herein and one or more other devices in fluid communication with a fluid path of the fluidic device. These other devices can be selected from, for example, a lysis device, an arraying device, and a detection device. For example, a lysis device can be configured to discharge to an input of the fluid path of the fluidic device. An arraying device can be configured to receive fluid discharged by the fluidic device. The detecting device can be, for example, a microscope, a particle counter, a magnet, a biocavity laser, a mass spectrometer, a polymerase chain reaction (PCR) device, a reverse transcriptase (RT)-PCR device, a microarray, or a hyperspectral imaging system.

In another aspect, the invention features methods of manufacturing the fluidic devices including selectively permeable obstacles as described herein.

The combination of patterned permeable nanostructure, e.g., carbon nanotube, obstacles and fluidic channels, and optionally specific binding moieties, provide significant advantages and benefits in methods of isolating, enriching, capturing, separating, detecting, and/or analyzing particles. The selective permeability of the nanostructure obstacles alters fluid streamlines and enhances, or reduces, particle-obstacle interactions across particle sizes ranging from sub-nanometers to centimeters. In one embodiment, this technology provides an extremely high degree of control of bioseparation processes to access bioparticles of interest, opening new pathways for both research and point-of-care diagnostics.

The new methods and devices provide efficient separation of specific bioparticles from multi-scale heterogeneous dispersions, which can facilitate bioassay development. In particular, the devices and systems can be implemented as a universal platform that can separate multiple particles having sizes (e.g., diameters) distributed across multiple size scales. Moreover, such a platform can be capable of high efficiency separation of bioparticles across multiple size scales. Further, the new devices can simplify the multiple and complex steps of current separation approaches.

The new devices and methods can also facilitate complete lab-on-a-chip assays for particle identification by providing the efficient capture of specific bioparticles, which is now the rate-limiting step for many such assays. These approaches can improve isolation yields by modifying streamlines at obstacle boundary-fluid interfaces, and altering the flow field comprised of the particles, which can counteract the tendency of even micro-scale systems to become diffusion limited. Taking advantage of the higher detection sensitivity and increased flexibility for further interrogation offered by solid-phase techniques for bioparticle isolation, the approaches described herein can enhance these techniques by consistently providing sufficient physical interaction between the bioparticles and surfaces to promote binding.

The devices can further include a detector module in fluid communication with the channel; the detector module can include one or more of a microscope, a cell counter, a magnet, a biocavity laser, a mass spectrometer, a polymerase chain reaction (PCR) device, a reverse transcriptase (RT)-PCR device, a microarray, or a hyperspectral imaging system, and it can be used to detect a certain feature of a given particle or type of particle, or detect a label or tag that selectively binds to the particles of interest, such as cells.

In some embodiments, the new devices can be adapted for implantation into a subject, e.g., in or near the circulatory system of a subject.

By "approximately equal" in the context of length, size, area, or other measurements is meant equal to within 10%.

By "biological particle" is meant any particle of biological origin that is insoluble in aqueous media. Examples include cells, particulate cell components, viruses, and complexes including proteins, lipids, nucleic acids, and carbohydrates. Cells include, for example, epithelial cells, cancer cells, bone marrow cells, fetal cells, progenitor cells, stem cells, foam cells, mesenchymal cells, immune system cells, endothelial cells, endometrial cells, connective tissue cells, trophoblasts, bacteria, fungi, or pathogens.

By "biological sample" is meant any sample of biological origin or containing, or potentially containing, biological particles. For example, biological samples can be cellular samples.

By "cellular sample" is meant a sample containing cells or components thereof. Such samples include naturally occurring fluids (e.g., blood, sweat, tears, ear flow, sputum, lymph, bone marrow suspension, urine, saliva, semen, vaginal flow, cerebrospinal fluid, cervical lavage, brain fluid, ascites, milk, secretions of the respiratory, intestinal or genitourinary tract, amniotic fluid, and water samples) and fluids into which cells have been introduced (e.g., culture media and liquefied tissue samples). The term also includes a lysate.

The cellular sample can be taken from a subject afflicted with a hematological condition, an inflammatory condition, an ischemic condition, a neoplastic condition, infection, trauma, endometriosis, or kidney failure. The neoplastic condition can be acute lymphoblastic leukemia, acute or chronic lymphocyctic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

By "blood component" is meant any component of whole blood, including host red blood cells, white blood cells, fetal white or red cells in maternal blood, platelets, epithelial cells, or tumor cells, e.g., circulating tumor cells (CTCs). Blood components also include the components of plasma, e.g., proteins, lipids, nucleic acids, and carbohydrates, and any other cells that can be present in blood, e.g., because of current or past pregnancy, organ transplant, infection, injury, or disease.

By "channel" is meant a passage through which fluid can flow. A channel can be a capillary, a conduit, or a strip of hydrophilic pattern on an otherwise hydrophobic surface wherein aqueous fluids are confined. A channel can also be created by air or fluid flow. A channel can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel can include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. In some cases where an open channel is used, the fluid may be held within the channel, for example, using surface tension (i.e., a concave or convex meniscus).

By "circulating tumor cell" (CTC) is meant a cancer cell that is exfoliated from a solid tumor of a subject and is found in the subject's circulating blood.

By "component" of a cell is meant any organelles (e.g., nuclei, perinuclear compartments, nuclear membranes, mitochondria, chloroplasts, or cell membranes), polymers or molecular complexes (e.g., lipids, polysaccharides, proteins (membrane, trans-membrane, or cytosolic), nucleic acids (native, therapeutic, or pathogenic), viral particles, or ribosomes), other molecules (e.g., hormones, ions, cofactors, or drugs), or components secreted from cells, including exosomes and microvesicles.

By "component" of a cellular sample is meant a subset of cells, or components thereof, contained within the sample.

By "density" in reference to an array of obstacles is meant the number of obstacles per unit of area. Array density is increased either by placing obstacles closer together or by increasing the size of obstacles relative to the gaps between obstacles.

"Areal density" of an array of obstacles refers to the cross-sectional area of obstacles per unit area.

"Areal density" of nanotubes within an obstacle refers to the cross-sectional area of nanotubes, as quantified by the outermost dimension (usually diameter) of the nanotubes, i.e., the nanotube is treated as a fiber, where the entire cross-sectional area of the nanotube is considered when calculating the cross-sectional area of the nanotubes within an obstacle divided by the cross-sectional area of the obstacle.

By "enriched sample" is meant a sample containing components that has been processed to increase the relative population of components of interest relative to other components typically present in a sample. For example, samples can be enriched by increasing the relative population of cells of interest by at least 10%, 25%, 50%, 75%, 100% or by a factor of at least 10, 100, 1,000, 10,000, 100,000, 1,000,000, 10,000,000, or even 100,000,000.

By "exchange buffer" in the context of a cellular sample is meant a medium distinct from the medium in which the cellular sample is originally suspended, and into which one or more components of the cellular sample are to be exchanged.

The term "fluid" generally refers to a substance that tends to flow and to conform to the outline of its container. Fluids include liquids and gases. Typically, fluids are materials that are unable to withstand a static shear stress, and when a shear stress is applied, the fluid experiences a continuing and permanent distortion. The fluid may have any suitable viscosity that permits flow.

By "gap" is meant an opening through which fluids or particles can flow. For example, a gap can be a space between two obstacles wherein fluids can flow, or a hydrophilic pattern on an otherwise hydrophobic surface wherein aqueous fluids are confined.

By "porosity" is meant a structural porosity of an obstacle that results from gaps within the obstacle. For example, the gaps between the plurality of nanostructures in an obstacle collectively represent the obstacles porosity.

An "average hydrodynamic size" of a given particle is the diameter of a sphere of the same composition that has the same drag coefficient as the average drag coefficient of a particle within a group of the given particles. The hydrodynamic size of a particle is affected by parameters including the physical dimensions, the shape, and the deformability of the particle.

The term "microfluidic" is used to characterize a system, device, or channel having at least one dimension of less than 1 mm.

By "obstacle" is meant an impediment to flow in a fluid path, e.g., a channel. Thus, obstacles can be protrusions from one surface. For example, an obstacle can refer to a post projecting from a base substrate, a hydrophobic barrier for aqueous fluids, or a wall or barrier that can extend partially or fully across a channel. In some embodiments, the obstacle can be permeable or selectively permeable to a particular material or a material of a particular size. For example, an obstacle can be a post made of nanostructures that includes a network of void spaces or openings that allow penetration of an aqueous component of a sample, or small particles relative to the average nanostructure spacing, but are too small for microscale particles in the fluid sample to enter. Obstacles can be filled from edge to edge with aligned nanostructures (and the corresponding network of void space), or can be hollow, in which case the nanostructures (and corresponding network of void space) make up one or more walls of the obstacle, e.g., one or more of the side, top, or bottom walls that make up the obstacle, while there are one or more larger airspaces (larger relative to the void space between nanostructures) within the obstacle, e.g., a single large airspace in the middle of the obstacle or many airspaces within a network of nanostructure walls within the obstacle. All of these features can be carefully tuned to provide precise permeability and control the capture efficiency for specific particles and the flow and direction of streamlines through the obstacles.

As used herein, the term "nanostructure" refers to elongated structures having a diameter on the order of nanometers and a length on the order of microns to millimeters or more, resulting in an aspect ratio greater than 10, e.g., greater than 100, 1000, 10,000, or greater. The terms "long axis" or "longitudinal axis" are used to refer to an imaginary line drawn parallel to the longest length of the nanostructure and intersecting the geometric center of the nanostructure. In some cases, the nanostructures may have an average maximum cross-sectional dimension of less than about 1 µm, less than about 500 nm, less than about 250 nm, less than about 100 nm, less than about 75 nm, less than about 50 nm, less than about 25 nm, less than about 10 nm, or, in some cases, less than about 1 nm. As used herein, the "maximum cross-sectional dimension" refers to the largest distance between two opposed boundaries of an individual structure that can be measured. In some instances, the nanostructure has a cylindrical or pseudo-cylindrical shape. The nanostructure may be, for example, a nanotube (e.g., a carbon nanotube), a nanowire, or a nanofiber, among others. In some embodiments, the nanostructures used in the devices, systems, and methods described herein can be grown on a growth substrate. In other embodiments, the nanostructures can be provided separately from their growth substrate, either attached to another substrate, or as a self-supporting structure detached from any substrate.

As used herein, a "carbon-based nanostructure" is a nanostructure that comprises at least about 30% carbon by mass. In some embodiments, the carbon-based nanostructures may comprise at least about 40%, at least about 50%, at least about 60%, at least about 70%, at least about 80%, at least about 90%, or at least about 95% of carbon by mass, or more. Examples of carbon-based nanostructures include carbon nanotubes, carbon nanowires, carbon nanofibers, and the like.

In some cases, a plurality of nanostructures can be interconnected, for instance, via bonds or mechanical entanglement. For example, the nanostructures can be interconnected via covalent bonds (e.g., carbon-carbon, or carbon-oxygen bonds), ionic bonds, hydrogen bonds, dative bonds, or the like. A plurality of nanostructures may also be interconnected via Van der Waals interactions in some cases. In some cases, a plurality of nanostructures may form a self-supporting structure.

As used herein, a "self-supporting structure" refers to a structure (e.g., solid, non-solid) having sufficient stability or rigidity to maintain its structural integrity (e.g., shape) without external support along surfaces of the structure. The terms "assembly" and "assembly of nanostructures" are used to refer to a plurality of self-supporting nanostructures. It should be understood that an assembly of nanostructures may form a self-supporting structure that may be manipulated, for example, as a film without the need for an additional support material, substrate, or any other material.

As used herein, the term "nanopermeable" with reference to an obstacle refers to an obstacle in which the spacing between nanostructures (e.g., carbon nanostructures) forming the obstacle (or walls of a hollow obstacle) ranges between less than about 1 and up to about 500 nanometers.

As used herein, a "selectively permeable" obstacle is one that permits the entry within its outer surface of certain sized particles, but excludes other particles that are too large to enter into the void spaces between the nanostructures that make up the obstacle.

As used herein, the term "nanotube" is given its ordinary meaning in the art and refers to a substantially cylindrical structure comprising a fused network of primarily six-membered aromatic rings. In some cases, nanotubes resemble a sheet of graphite formed into a seamless cylindrical structure. It should be understood that the nanotube may also comprise rings or lattice structures other than six-membered rings. Typically, at least one end of the nanotube may be capped, i.e., with a curved or nonplanar aromatic group. Nanotubes can have a diameter of the order of nanometers and a length on the order of millimeters or centimeters or greater, e.g., on the order of tenths of microns, resulting in an aspect ratio greater than 10, e.g., an aspect ratio greater than 100, 1000, 10,000, or greater. In some cases, the nanotube is a carbon nanotube.

The term "carbon nanotubes" refers to nanotubes comprising primarily carbon atoms and includes single-walled nanotubes (SWNTs), double-walled CNTs (DWNTs), multi-walled nanotubes (MWNTs) (e.g., concentric carbon nanotubes), inorganic derivatives thereof, and the like. In some cases, the carbon nanotube is a multi-walled carbon nanotube (e.g., a double-walled carbon nanotube). In some cases, the nanotube has a diameter less than 1 µm, less than 100 nm, 50 nm, less than 25 nm, less than 10 nm, or, in some cases, less than 1 nm. In one set of embodiments the nanotubes have an average diameter of 50 nm or less, and are arranged in groups to form the composite obstacles described herein. The inorganic materials include semiconductors such as silicon (Si), indium-gallium-arsenide (InGaAs), boron nitride (BN), silicon nitride ($Si_3N_4$), and silicon carbide (SiC), dichalcogenides such as WS2 and WSe2, oxides such as titanium dioxide ($TiO_2$) and molybdenum trioxide (MoO3), and boron-carbon-nitrogen compositions such as $BC_2N_2$ and $BC_4N$.

Substrates (e.g., growth substrates) suitable for use in the invention include prepregs, polymer resins, dry weaves and tows, inorganic materials such as carbon (e.g., graphite), metals, alloys, intermetallics, metal oxides, metal nitrides, ceramics, and the like. In some cases, the substrate may be a fiber, tow of fibers, a weave, and the like. The substrate may further comprise a conducting material, such as conductive fibers, weaves, or nanostructures.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DESCRIPTION OF DRAWINGS

FIG. 2A, FIG. 2B, and FIG. 2C are, respectively, scanning electron micrographs of nanopermeable posts at different scales. FIG. 2A shows multiple cylindrical post obstacles disposed within a fluidic path of a microfluidic device. FIG. 2B shows the overall cylindrical post obstacle including the external outer surface. FIG. 2C shows a close up view of a portion of the obstacle outer boundary of the obstacle to show individual carbon nanotubes that are substantially aligned at the tops and bottoms of the nanotubes, but that are not necessarily straight between the tops and bottoms.

FIG. 3A and FIG. 3B are, respectively, scanning electron micrographs of a solid post at different scales. FIG. 3A shows the overall post obstacle including the outer boundary (e.g., external surface). FIG. 3B shows a close up view of a portion of the outer boundary of the obstacle.

FIG. 4 is schematic of a chip with a single post including a grouping of carbon nanotubes disposed in a channel. The device is configured to bind particles that have been focused in a stream that is directed at the single post obstacle.

FIG. 5A shows a selectively permeable round post. FIG. 5B shows a hollow round post with a selectively permeable wall. FIG. 5C shows a selectively permeable chevron-shaped wall. FIG. 5D shows a hollow foil-shaped obstacle with a selectively permeable wall. Flow is left to right in the images.

FIG. 6 is an illustration of types of obstacles and different ways of configuring the obstacles.

FIG. 7A is a schematic representation of a square array of round obstacles. FIG. 7B is a schematic representation of an equilateral triangle array of cylindrical obstacles.

FIG. 13 is an illustration of a device for size based separation.

FIGS. 14A-14C are schematic depictions of an array that separates cells based on lateral displacement: FIG. 14A illustrates the lateral displacement of subsequent rows; FIG. 14B illustrates how fluid flowing through a gap is divided unequally around obstacles in subsequent rows; and FIG. 14C illustrates how a particle with a hydrodynamic size above the critical size is displaced laterally in the device.

FIG. 20A shows a device in which the obstacle 310 is not functionalized with a binding moiety and the small particles pass through the obstacle. FIG. 20B shows a device in which the obstacle is functionalized with a binding moiety and the small particles are captured inside the obstacle.

FIG. 28A and FIG. 28B are confocal micrographs of, respectively, a nanopermeable post and a solid post as a fluorescent dye solution is flowed through the micro-channel. The dye solution is shown penetrating the nanopermeable post but not the solid post.

FIG. 29A and FIG. 29B are graphs of the relative intensity plots of dye infiltration over time inside, respectively, a nanopermeable post and a solid post. The dye solution is shown penetrating the nanopermeable post but not the solid post.

FIG. 30 is a sequence of micrographs tracking fluorescent quantum dots flowing through a channel with a nanopermeable post. A dot that passes around the outside of post moves downstream faster than a dot that passes through the posts.

FIG. 31A is a schematic top view of a nanopermeable Y-barrier as well as micrographs showing the distribution of 10 μm polymer beads at the device inlet, the concentrator outlet, and the waste outlet. The concentration of beads is highest in the concentrator outlet and lowest in barrier outlet. FIG. 31B is a fluorescent micrograph showing red fluorescent BSA molecules that have passed through the nanopermeable barriers. FIG. 31C shows that 10 μm polymer beads cannot pass through the nanopermeable barrier sides, and are directed to the central channel. FIG. 31D shows streak images of a single 10 μm bead as it enters the constricted section of the barrier.

FIG. 35 is a graph that shows data points of individual bead positions when they are 200 μm in front of the posts and when they are at their closest to the posts. Beads approaching the nanopermeable post pass several microns closer to the post boundary than their counterparts approaching the solid post.

FIG. 36 is a graph of the interception efficiency of the two posts relative to different starting positions of the beads. The graph shows that the interception efficiency of the nanopermeable post is higher than the interception efficiency of the solid post.

FIG. 37A and FIG. 37B, respectively, present a schematic and a scanning electron micrograph of a single post cell capture device. FIGS. 37C and 37D are images showing the location of fluorescent captured cells on, respectively, devices with nanopermeable and devices with solid posts of identical geometry. The inset control boxes show capture on non-functionalized chips. The nanopermeable post demonstrated capture enhanced by 6-7 fold relative to solid posts of the same geometry. Non-specific binding was low.

FIG. 38A and FIG. 38B, respectively, present a schematic and a scanning electron micrograph of a cell capture device with an array of posts configured to capture *Escherichia coli* bacteria. FIG. 38C and FIG. 38D are images showing the location of fluorescent captured cells on, respectively, devices with nanopermeable and devices with solid posts of identical geometry. The inset control boxes show capture on non-functionalized chips. The nanopermeable posts demonstrated capture enhanced by 6-7 fold relative to solid posts of the same geometry. Non-specific binding was low.

FIG. 41A is a micrograph of the as-grown patterned CNT forests. FIG. 41B is a micrograph of same patterned forests inside microchannel after wet treatment. A comparison of the micrographs indicates that less than 1.3% change in post diameter was observed after wetting.

Like reference symbols in the various drawings indicate like elements.

DETAILED DESCRIPTION

Figure 1A:
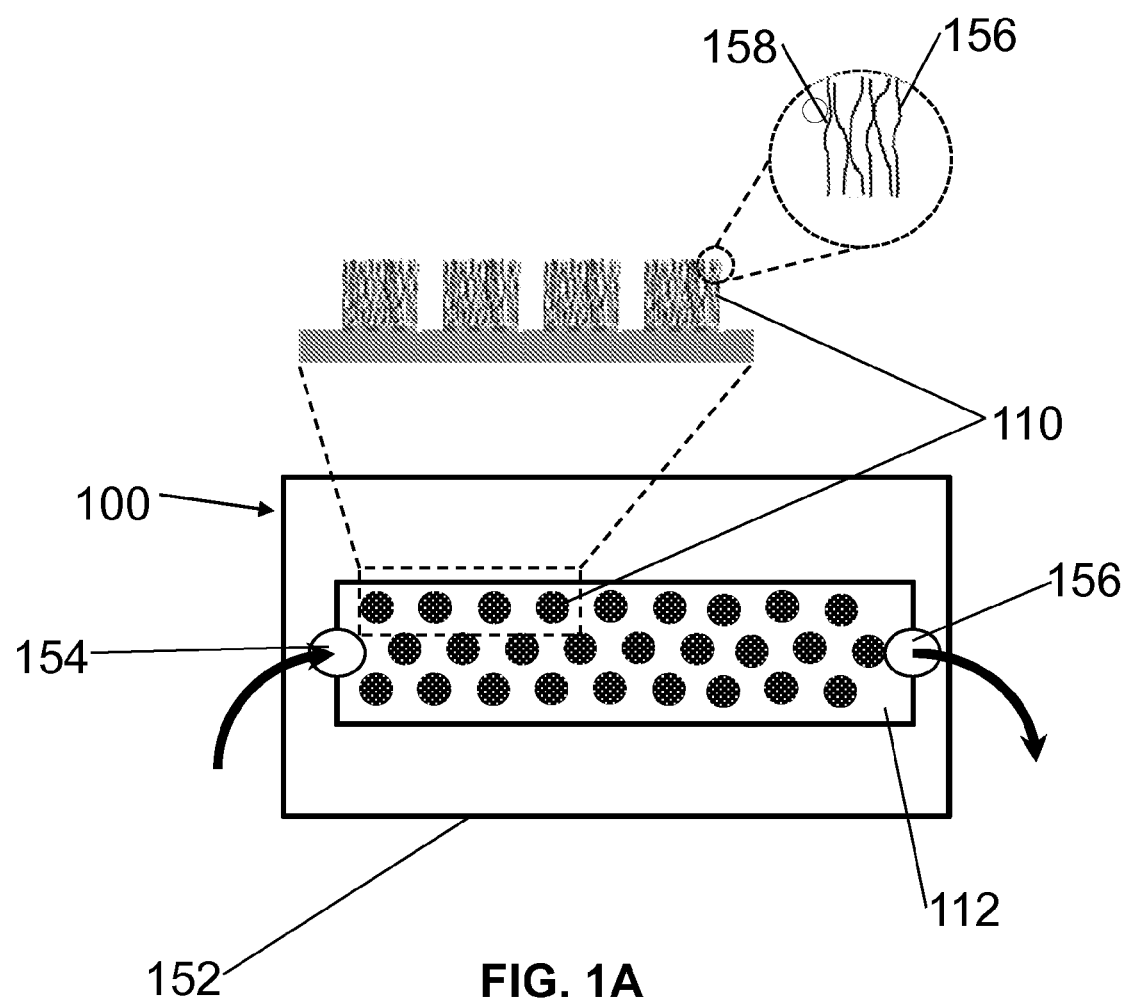
FIGS. 1A and 1B are schematic views of a device including a channel with an array of patterned obstacles, which, in this set of embodiments, are illustrated as posts (e.g., microposts). Each individual obstacle in the array is made from a selectively permeable material including carbon nanotubes. Fluid and particles that are small enough to fit within the void spaces between carbon nanotubes can pass through the outer boundaries of the obstacles and into the obstacles. Particles that are too large to enter the void spaces, and thus cannot pass through the outer boundaries (e.g., external surface) of the obstacles, must pass around them. Further, particles that are too large to enter the space between adjacent obstacles in the array cannot pass through the array of patterned obstacles and are thereby filtered.

Discribed herein are new devices and methods that include an array of selectively permeable obstacles (e.g., obstacles that include multiple aligned nanostructures, e.g., carbon nanotubes or nanorods, with spaces in between) arranged within a fluid path, e.g., a fluidic or microfluidic channel, which can be used to mechanically and/or chemically manipulate, e.g., isolate, separate, capture, detect, concentrate, enrich, and/or analyze, a wide variety of particles across many magnitudes of size ranges. The high permeability and excellent structural properties of the nanostructure obstacles described herein enable the design and production of devices adapted for highly efficient and specific manipulation, e.g., capture of various bioparticles.

Several devices described herein combine selectively permeable carbon nanotube obstacles with microfluidics to enable the mechanical and/or chemical manipulation of bioparticles of varying sizes. In contrast to previously described fluidic platforms for particle isolation, which are usually highly tailored to perform optimally for particles of a single size, the described permeable carbon nanotube obstacles provide a platform capable of high efficiency separation of particles, e.g., bioparticles, across multiple size scales, ranging from viruses to bacteria and cells. Furthermore, the devices described herein can be made using a fabrication process that is simple and low-cost, with a fast turnaround for prototyping. In addition to optimal design of the microstructured features via simple patterning, there is potential for additional versatility and utility by altering the spacing between individual nanotubes, i.e., changing the degree of nanoporosity, such as by modulating carbon nanotube growth conditions. Altering the spacing between individual nanostructures can allow particles of different sizes to penetrate into the permeable obstacles, as well as change the fluidic resistance for liquid passing through the obstacles and therefore their surrounding flow-field. The fabrication techniques described herein (including the ability to configure the positions of nanostructures) can enable one to create new families of devices for a very broad range of applications including lab-on-a-chip devices for blood analysis to monitor patients at the point-of-care, ultra-rapid cell sorters to detect rare cells in circulation for diagnostics (e.g., cancer, prenatal, infections), purification of stem cells from various bodily fluids, high-throughput barriers for pathogen depletion, and isolation of bacteria and viruses for diagnosing infectious diseases.

The use of permeable, e.g., nanopermeable, rather than solid, obstacles can greatly enhance particle-surface interactions by reducing boundary layer effects around the obstacles as well as increasing the particle-solid surface interaction area. In particular, obstacles made of groups of generally aligned, and optionally functionalized, e.g., chemically functionalized, nanostructures such as carbon nanotubes, can be made in the form of, e.g., posts, walls, and other forms of barriers, and can be incorporated into fluidic, e.g., microfluidic, devices to isolate particles with sizes spanning several orders of magnitude. Some of the systems and methods described herein take advantage of the physical mechanical properties, high nanoscale permeability and surface area, and/or ability to functionalize the surface of nanostructures such as carbon nanotubes for bioseparation.

The selectively permeable, e.g., nanopermeable, obstacles can be, for example, spaced apart posts or walls with the specific obstacle chosen based on the size and characteristics of the particles to be analyzed, separated, and/or captured. The permeable obstacles can be arranged in an array within, and in some cases can be sealed inside, a fluidic, e.g., microfluidic, channel and fluids can be introduced by pressure driven flow. Various chemical and biological binding moieties can be used to functionalize the nanotubes in one or more of the permeable obstacles to specifically bind to particular biomolecules. Each individual obstacle can have the same or different types of binding moieties as other obstacles in the same device. Furthermore, a single obstacle can include only one type of binding moiety or multiple different types of binding moieties, e.g., within different parts of the obstacle. In general, each nanopermeable obstacle within the device or array is made up of a plurality of nanostructures, e.g., carbon nanotubes, e.g., at least 1000, 5000, 10,000, 50,000, 100, 000, 500,000, 1,000,000 or more nanostructures in each obstacle, e.g., ~$10^8$ nanotubes per mm$^2$ of a dense network or grouping of nanotubes. The diameter of carbon nanotubes can range between about 0.2 nm to several hundreds of nanometers, and the spacing between individual nanotubes can vary.

In addition, each of the obstacles can be created by locating the plurality of nanostructures on a substrate in close proximity to each other, such that the vertically-aligned (substantially aligned) nanostructures are densely packed on the substrate. The nanostructures may be spaced about less than 1 nanometer to about 1 micron apart, e.g., 50 to 150 nm or 75 to 100 nm, and in some embodiments individual nanostructures may contact at least one adjacent nanostructure. The nanostructures extend away from their respective bottom ends on the substrate, and can be arranged generally in parallel, e.g., in general alignment at least over a portion of their length, or may follow statistical paths to form complex networks of nanotubes that defines a nanostructure, e.g., nanotube or nanorod, grouping. These groupings of nanostructures form the obstacles and establish the nanoscale inter-structure spacing that permits certain materials and/or particles to permeate into and/or through the network of void spaces within the permeable obstacles.

In some embodiments, the nanostructures that form the obstacles can be attached, e.g., adhered or chemically bonded (e.g., ionically or covalently bonded), to two opposed boundaries of an enclosed channel, and arranged such that fluid is transported substantially perpendicularly to the longitudinal axes of the aligned nanostructures. For example, in some embodiments, nanostructures can be attached to a growth substrate, and a second substrate comprising a channel formed within it can be positioned over the nanostructures such that the bottom of the channel contacts and is attached to the nanostructures. The nanostructures can be attached to the bottom of the channel, for example, buy applying an adhesive to the bottom of the channel and joining the bottom of the channel to the nanostructures. The nanostructures might also be attached to the bottom of the channel by exposing the bottom of the channel (e.g., a glass channel, a PDMS channel) to plasma, and forming a chemical bond between the plasma-exposed surface and the nanostructures. In such devices, at least a portion of the aligned nanostructures are attached to the floor and the ceiling of an enclosed channel defined by the first and second substrates.

The carbon nanotube growth conditions can be controlled to grow larger/smaller aligned carbon nanotubes with larger/smaller diameters, and with smaller/larger inter-CNT spacing. This allows the nanopermeability of the obstacles to be tuned for specific applications.

The spacing between carbon nanostructures can also be controlled by mechanical densification of carbon nanostructures after the nanostructures are formed. As discussed in more detail below, a plurality of nanostructures can be formed such that the long axes of the nanostructures are substantially aligned relative to each other. Each nanostructure is positioned relative to an adjacent nanostructure at a distance so as to together define an average distance between adjacent nanostructures. In some embodiments, the average distance between adjacent nanostructures is roughly equal for each nanostructure. In other embodiments, the distances between adjacent nanostructures may vary.

A first force with a component normal to the long axes of the nanostructures may be applied to the plurality of nanostructures. The application of the first force may result in the reduction of the average distance between the nanostructures. The force described herein may be applied using any method known in the art. In some embodiments, a mechanical tool is used to apply the force to the plurality of nanostructures. In some embodiments, a second force may be applied to the nanostructures. The second force may include a second component that is normal to the long axes of the nanostructures and orthogonal to the first component of the first force. The application of the second force may lead to a further reduction of the average distance between adjacent nanostructures. The application of a first and/or second force may reduce the average distance between adjacent nanostructures by varying amounts. In some cases, the average distance between adjacent nanostructures is reduced by at least about 10%. In some instances, the average distance between adjacent nanostructures is reduced by at least about 10%, 20%, 30%, 40%, 50%, at least about 70%, at least about 80%, at least about 90%, at least about 95%, at least about 99%, or more. In some embodiments, the average distance between adjacent nanostructures may be reduced to less than about 500 nm, less than about 60 nm, less than about 40 nm, less than about 30 nm, less than about 20 nm, less than about 10 nm, less than about 5 nm, or less.

As discussed in more detail below, the spacing between carbon nanostructures can also be controlled by coating the carbon nanostructures (e.g., using chemical vapor deposition). For example, polymer CVD can be used to put a 10 nm coating conformally around carbon nanotubes with 80 nm average spacing between nanotubes to generate an average 60 nm spacing between nanotubes.

The devices and methods described herein can be used for separating a desired target particle, such as a specific type of cell, from a mixture, or enriching the population of a desired particle, e.g., specific cell, in a sample including a mixture of different types of particles. For example, the devices can be used to separate particles of different sizes suspended in a fluid sample that is flowed in the fluid path past the array of obstacles. In particular, particles of a first type can be captured on an outer surface of the array of obstacles, particles of a second type can be captured within the array (e.g., in the spaces between obstacles in the array), and particles of a third type can be captured within the pores of one or more obstacles.

The methods are generally based on sequential processing steps, each of which reduces the number of undesired cells in the mixture, but one processing step may suffice in some embodiments. Devices for carrying out various processing steps can be separate or integrated into one microfluidic system. The devices include devices for cell binding, devices for cell lysis, devices for arraying cells, and devices for separation, e.g., based on size, shape, and/or deformability or other criteria. In certain embodiments, processing steps are used to reduce the number of cells prior to arraying. The methods described herein retain at least 75%, 80%, 90%, 95%, 98%, or 99% of the desired cells compared to the initial sample mixture, while potentially enriching the population of desired cells by a factor of at least 100, 1000, 10,000, 100,000, or even 1,000,000 relative to one or more non-desired cell types. For example, the methods described herein can be used to separate or enrich cells in blood (Table 1).

TABLE 1

Types, concentrations, and sizes of blood cells.

| Cell Type | Concentration (cells/μl) | Size (μm) |
|---|---|---|
| Red blood cells (RBC) | $4.2$-$6.1 \times 10^6$ | 4-6 |
| Segmented Neutrophils (WBC) | 3600 | >10 |
| Band Neutrophils (WBC) | 120 | >10 |
| Lymphocytes (WBC) | 1500 | >10 |
| Monocytes (WBC) | 480 | >10 |
| Eosinophils (WBC) | 180 | >10 |
| Basophils (WBC) | 120 | >10 |
| Platelets | $500 \times 10^3$ | 1-2 |
| Fetal Nucleated Red Blood Cells | $2$-$50 \times 10^3$ | 8-12 |

The permeable obstacles can be configured, in some embodiments, such that streamlines of fluid that flow past the permeable obstacle are modified, relative to the streamlines that would be observed were the permeable obstacle replaced with an obstacle of the same defined space and made of a material through which fluid does not flow (e.g., a solid, non-porous article), but under otherwise essentially identical conditions (e.g., flow rate, fluid composition and viscosity, temperature, pressure, etc.). In some embodiments, the obstacles can be configured to alter the streamlines such that a smaller number of the particles contacts the obstacles, relative to the number that would contact obstacles of the same defined space and made of a material through which fluid does not flow (e.g., a solid, non-porous article). Such arrangements can be useful, for example, in situations in which one desires to transport a relatively large number of relatively small particles completely through the array of obstacles, for example, so that they may be collected at a downstream location. In some embodiments, the obstacles can be configured to alter the streamlines such that a larger number of the particles contacts the obstacles, relative to the number that would contact obstacles of the same defined space and made of a material through which fluid does not flow (e.g., a solid, non-porous article). Such arrangements can be useful, for example, in situations where one desires to enhance the amount of interaction between the particles within a fluid stream and the obstacles within the array.

In some embodiments, an obstacle (or a plurality of obstacles) can be configured such that, after a fluid has been transported through the obstacle, its cross-sectional shape remains substantially similar to its cross-sectional shape prior to fluid being transported through the article. In some cases, obstacles comprising relatively long nanostructures (e.g., nanostructures with aspect ratios of at least about 100, at least about 1000, at least about 10,000, or greater) can maintain their cross-sectional shapes after fluid is transported through them. In addition, obstacles can be configured such that their cross-sectional shapes are maintained after a liquid has been transported through them. In some embodiments, the ability to maintain the cross-sectional shape of an obstacle can be enhanced by employing controlled flow rates of liquids or other fluids through the obstacles and/or by attaching the nanostructures within the obstacles to opposed boundaries within a flow channel.

Microfluidic Devices that Include Permeable Obstacles

Devices with Selectively Permeable Obstacles in the Form of Posts

Figure 1B:
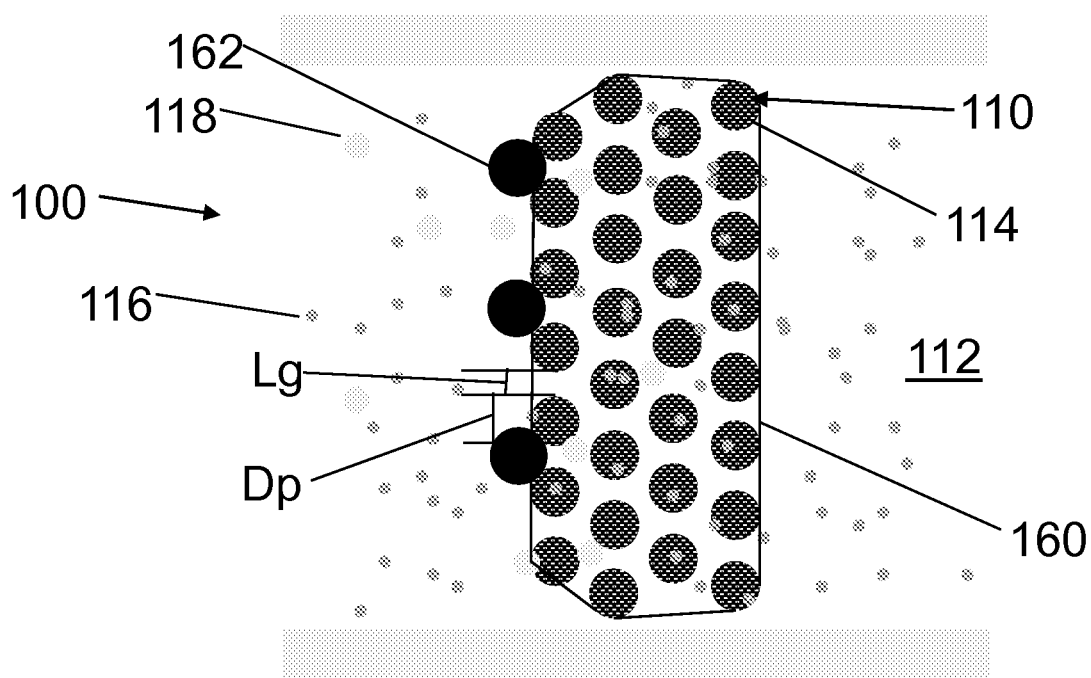

FIGS. 1A and 1B show schematic diagrams of a microfluidic device 100 configured for capturing bioparticles contained in a fluid sample. The microfluidic device 100 includes a substrate 152 in which a microfluidic channel 112 (e.g., a microfluidic path) is formed. The microfluidic channel 112 includes an inlet 154 and an outlet 156 to flow fluid (e.g., a fluid sample including suspended particles) through the microfluidic channel 112. The microfluidic device 100 includes an array of obstacles 110 disposed in the microfluidic channel 112. In some embodiments, each obstacle 110 in the array is a selectively permeable post comprising a plurality of nanostructures including a first nanostructure 156, a second nanostructure 158, (e.g., nanotubes) defining multiple interconnected spaces or voids. In some embodiments, microfluidic channel 112 can be capped such that the channel is at least partially enclosed (with the exception of inlet 154 and outlet 156). The nanostructures within obstacles 110 can be configured, in some embodiments, such that they are attached (e.g., adhered, bonded) to two opposed boundaries of the enclosed channel formed by substrate 154 and the cap. In the device illustrated in FIG. 1A, the nanostructures are arranged such that fluid flow through channel 112 is substantially perpendicular to the longitudinal axes of the nanostructures within obstacles 110.

As shown in FIG. 1B, the illustrated obstacles 110 are round posts with a diameter $D_p$ arranged in a hexagonal packing pattern. The diameter of the posts can range upwards from about 1 micron to about a practical upper size of about 1 centimeter (e.g., about 5 microns, 10 microns, 50 microns, 100 microns, 250 microns, 500 microns, 1 millimeter, or 5 millimeters). The pattern defines gaps with a length $L_g$ between posts. The posts can have varied cross-sectional shapes, such as substantially circular shapes, substantially triangular shapes, substantially rectangular shapes, substantially square shapes, and other more complex shapes. In some cases, the gaps between obstacles are between about 1 to 100 microns (e.g., 20 to 75 microns, 25 to 60 microns, or 30 to 55 microns).

The array of obstacles 110 defines an array outer surface or boundary 160. Each obstacle 110 in the array of obstacles is formed to define a respective outer boundary 114. Fluid and particles 116, 118 that are small enough to fit within spaces between the obstacles 110 in the array can pass through an outer boundary defined by the array, whereas particles 162 that are too large to pass into the array are captured at the array outer boundary 160. Further, fluid and particles (not shown) that are small enough to fit within the voids of each obstacle 110 can pass through the respective external surface or outer boundary 114 of each obstacle and into the plurality of nanostructures in each obstacle 110. Particles 118 that are larger than the voids cannot pass through the outer boundaries 114 of the obstacles 110.

Referring to FIG. 2A, 2B, and FIG. 2C, the obstacles 110 in an array can be formed from nanostructures, such as carbon nanotubes such that multiple carbon nanotubes 120 together form a dense group of nanotubes in the shape of a single obstacle 110 with internal surfaces and interconnecting voids within the single obstacle 110. The outer boundary 114 of an obstacle 110 includes the outer face(s) of the obstacle 110 and generally corresponds to the outer surface(s) of a solid obstacle of a corresponding shape (see, for example, FIG. 3A and FIG. 3B). The surfaces of individual carbon nanotubes included in particular obstacle 110 form internal surfaces within the particular obstacle 110. The multiple obstacles 110, each including a respective dense group of nanotubes, then form the array of obstacles. Each obstacle 110 can be disposed within the array at respective and pre-defined positions to define an inter-obstacle space for the array.

In some embodiments, the inter-obstacle space defined for such an array of obstacles can be formed by a network of gaps, which can include, for example, a staggered two-dimensional array of obstacles, e.g., in which each successive row is offset by less than half of the period of the previous row. The device can also include a second staggered two-dimensional array of obstacles, which is optionally oriented in a different direction than the first array. In this case, the first array can be situated upstream of the second array, and the second array can have a higher density of obstacles than the first array. Multiple arrays can be configured in this manner, such that each additional array has an equal or higher density than any array upstream of the additional array. A comparison of FIG. 2B and FIG. 2C, which are scanning electron micrographs of a permeable carbon nanotube post, and FIG. 3A and FIG. 3B, which show a solid polydimethylsiloxane (PDMS) post, highlights the porosity of a circular post made from a permeable carbon nanotube forest in comparison to a non-permeable (solid) post made from PDMS using soft lithography.

The carbon nanotube obstacles, e.g., having an average carbon nanotube diameter of 8 nm, can be grown, for example, with a $Fe/Al_2O_3$ catalyst using atmospheric-pressure thermal chemical vapor deposition (CVD) as described, e.g., in detail in E. J. Garcia, A. J. Hart, B. L. Wardle, and A. H. Slocum, Nanotechnology, 18(16), 165602 (2007); A. J. Hart, A. H. Slocum, J. Phys. Chem. B110, 8250 (April, 2006); and B. L. Wardle et al., Adv. Mater. 20, 2707 (July, 2008); U.S. Pat. Pub. No. 2008/0075954; and U.S. Pat. Pub. No. 2009/0311166. In some embodiments, the carbon nanotube obstacles can be patterned on silicon by using photolithography to control the area of catalyst coverage on the wafer as described in detail in E. J. Garcia, A. J. Hart, B. L. Wardle, A. H. Slocum, Nanotechnology 18, 2151-2156 (2007).

In some embodiments, standard photolithography is used to pattern plain <100> 152 mm (6") diameter silicon wafers, followed by electron beam deposition of a 10 nm $Al_2O_3$ layer and a 1 nm Fe layer. Catalyst areas are then defined by photoresist lift-off, soaking the wafer in acetone for 8 minutes with mild sonication. Carbon nanotube (CNT) growth is performed in a 102 mm (4") quartz tube CVD furnace at atmospheric pressure using reactant gases of $C_2H_4$, $H_2$, and He (400/400/1900 sccm). Catalyst annealing is carried out in a reducing $He/H_2$ environment at 680° C., leading to the formation of Fe catalyst nanoparticles of approximately 10 nm diameter. $C_2H_4$ is then introduced into the furnace to initiate CNT growth, occurring at a rate of approximately 100 μm/min until the flow of $C_2H_4$ is discontinued. The technique results in groups of multi-walled substantially vertically-aligned carbon nanotubes (3-4 concentric walls) with an average tube diameter of 8 nm and an average inter-CNT spacing of approximately 80 nm, thus yielding a 1% volume fraction of carbon nanotubes.

Incorporation of the patterned carbon nanotube structures into devices is achieved using, for example, standard soft lithography techniques. PDMS channels (2 cm long, 3 mm wide, 100 μm tall) are fabricated from SU-8 photoresist negative molds, and bonded to the silicon wafers containing the carbon nanotube features after oxygen plasma treatment. In some embodiments, a chemical bond can be formed between the nanostructures within the channels and a surface of the PDMS channel, resulting in nanostructures that are bonded to two opposed boundaries of the enclosed channel. Not wishing to be bound by any particular theory, it is believed that, by plasma treating the PDMS, the surface of the PDMS can be activated such that it is capable of forming chemical bonds with the nanostructures when they are placed in contact with each other. In some embodiments, a channel can be formed in a channel substrate formed of plastic, metal, or some other material, and an adhesive can be applied to the channel substrate and/or the growth substrate on which the nanostructures are arranged. The channel substrate and the growth substrate can then be adhered to form an enclosed channel. In some embodiments, the nanostructures can adhere to at least a portion of the channel surface in the channel substrate to which adhesive has been applied, resulting in nanostructures that are attached to two opposed boundaries (e.g., the surface of the growth substrate and the bottom surface of the channel in the channel substrate) of the enclosed channel.

The carbon nanotubes can be grown as a generally aligned, densely packed morphology up to several millimeters in height, and with an average spacing of, e.g., 80 nm, which results in an overall void space of 99% (1% volume fraction carbon nanotubes). The average spacing between carbon nanotubes can be found by measuring the average carbon nanotube maximum external diameter and the mass of carbon nanotubes in an obstacle. By combining the mass of the nanotubes and the diameter measured by SAXS or TEM one can infer the inter-CNT spacing. See also J. Phys. Chem. C 2009, 113, 20576-20582.

As such, the obstacles 110 can be disposed in an array and used to mechanically capture subpopulations of cells based on the sizes of the subpopulation using techniques similar to those described above. Additionally, the obstacles 110 can have functionalized surfaces provided with binding moieties, e.g., antibodies or ligands for cell surface receptors that bind to a particular subpopulation of cells, which capture specific bioparticles that come in contact with the obstacles. In this manner, the obstacles 110 can capture bioparticles mechanically or chemically (or both) on the outer boundaries of the obstacles 110 or on surfaces of internal structures within the obstacles 110 (or both). The extent of particle-surface interactions can significantly impact the bioparticle capture rate. As described herein, the flow of fluid through the selectively permeable obstacles 110 can modify streamlines near the obstacles and can advantageously increase the likelihood of contact between particles 116, 118, 162, and obstacles 110, or likewise advantageously decrease the likelihood of contact and capture.

The depletion of whole cells from a mixture by binding the cells to the surfaces of the device can employ positive selection, i.e., the desired cells are bound to the device, or it can employ negative selection, i.e., the desired cells pass through the device. In either case, the population of cells containing the desired cells is collected for analysis or further processing.

The device can be a microfluidic flow system containing an array of obstacles of various shapes that are capable of binding a population of cells, e.g., those expressing a specific surface molecule, in a mixture. The bound cells can be directly analyzed on the device or be removed from the device, e.g., for further analysis or processing. Alternatively, cells not bound to the obstacles can be collected, e.g., for further processing or analysis.

The microfluidic device 100 can provide high throughput processing of fluid samples. The obstacles 110 can be sized and positioned in the channel such that the gaps between obstacles are much larger (e.g., 1.5, 2, 4, or 10 times larger) than the largest particles anticipated to be present in samples to be processed. This configuration can reduce the likelihood that the device will clog.

Referring to FIG. 4, a device 200 includes a single obstacle 110 disposed in the center of a channel. The diameter $D_p$ of the single post can range between about 1 micron and about 1 centimeter (e.g., 2 microns, 5 microns, 10 microns, 100 microns, 1 millimeter). The gap $L_g$ between the single post 110 and the walls of the channel 112 can range between about 1 to 10 nanometers and about 1 centimeter (e.g., 10 nm, 25 nm, 50, nm, 80 nm, 100 nm, 1 micron, 10 microns, 100 microns, 1 millimeter, or even greater than 1 cm). The device 200 is configured to bind particles that have been focused in a stream that is directed at the single obstacle 110. Particles can be focused, for example, using the devices and methods described in detail in U.S. Pat. Pub. No. 2009/014360 "Systems and Methods for Particle Focusing in Microchannels."

The dimensions and geometry of the obstacles can vary significantly. For example, the obstacles can have substantially cylindrical or substantially square cross sections. Because the permeability of the array of obstacles affects the flow of a fluid sample through the array, the distance between obstacles can be selected according to the analytical model described below to maximize a permeability of the array of obstacles. To model the permeability of the array, the array is considered to be a porous medium. The flow resistance in such media can be expressed as the sum of a viscous friction (Darcy drag) and a pressure drag (Forchheimer drag). The sum of these friction components (i.e. the total friction) is referred to as Darcy-Forchheimer friction.

$$\frac{dP}{dx}\frac{D}{\rho \bar{u}^2}Re = -\frac{D^2}{\kappa} - bDRe \quad (1)$$

In Equation (1) above, the first term on the right hand side represents Darcy drag, which is a function of obstacle cross-sectional dimension (D) and permeability of the porous media (κ). At low Reynolds number, which is typical in flow through microfluidic devices, Darcy drag dominates Forchheimer drag, and the latter can be ignored. In such situations, flow resistance through porous media in microfluidic devices (e.g., the array of obstacles disposed in the fluid path) can be minimized by minimizing Darcy drag, which, in turn, can be achieved by either decreasing the obstacle cross-sectional dimension (D) or the permeability (κ). Because flow resistance is proportional to a square of the cross-sectional dimension ($D^2$), nanoscale structures offer attractive solutions to decrease the resistance in porous media.

Among others, Sabri Ergun (1952) studied the flow through porous materials by modeling their internal structures including regular beds of aligned pillars (equivalent diameter, D; height >>D) that lay perpendicular to the flow direction and that are spaced apart by a distance S. In his work, Ergun derived a semi-empirical expression (Equation 2) that relates feature size (D [m]), structural porosity (Φ), and fluid permeability (κ [m$^2$]). S. Ergun. Fluid flow through packed columns. Chemical Engineering Progress, 48(2):89-94, 1952.

$$\kappa_{Ergun} = \frac{1}{c}\frac{\phi^3}{(1-\phi)^2}D^2 \quad (2)$$

In Equation (2), c is a constant dependent on both the pillars' geometry (e.g., squares v/s cylinders) and the feature's size scale (e.g., macroscopic v/s microscopic). In Ergun's meso-scale experiments (average pillar diameter between 0.5 and 0.8 mm), the constant c was quantified as 150. The same constant was used in this work, but can be varied depending upon obstacle arrangement in the array.

Further, in this work, the structural porosity was defined in terms of the obstacle size (e.g., cross-sectional diameter, D), inner edge-to-inner edge distance between two adjacently formed obstacles in the array (p), and the center-to-center distance between the two adjacently formed obstacles, as shown in Equations (3a and 3b).

$$\phi = 1 - \frac{\pi}{4}\frac{D^2}{(S+D)^2} \quad (3a)$$

$$= 1 - \frac{\pi}{4}\frac{D^2}{(p+2D)^2} \quad (3b)$$

The parameter p is independent of the obstacle size, D, and, as shown in Equation 4, is useful to derive a formula for permeability (κ) that is dependent on the obstacle size, D.

$$\kappa = \frac{(p^2 + 2pD)^3}{150(p+D)^2 D^2} \quad (4)$$

Once the spacing between particles (i.e., p) has been set, then permeability (κ) of the porous media is affected only by the obstacle size, D. In other words, permeability becomes inversely proportional to obstacle size. Therefore, miniaturization (i.e., D gets smaller) contributes to higher permeability. Given two filters with the same mesh size (p), the most permeable one will be the one characterized by the smaller feature size (or intra-pore spacing). Substituting the relationship between permeability ($\kappa$) and obstacle size (D) in the representation of Darcy's drag reveals that Darcy's drag is proportional to the cube of the obstacle size, D. Therefore, decreasing the size of obstacles that form a porous medium significantly decreases Darcy's drag through the medium.

In addition to the size, the distance between obstacles can also vary and can be different in the flow direction compared to the direction orthogonal to the flow. In some embodiments, the distance between the edges of the obstacles is slightly larger than the size of the largest cell in the mixture. This arrangement enables flow of cells without the cells being mechanically squeezed between the obstacles and thus damaged during the flow process, and also maximizes the numbers of collisions between cells and the obstacles in order to increase the probability of binding. The flow direction with respect to the orientation of the obstacles can also be altered to enhance interaction of cells with obstacles.

Configurations of Posts

Figure 5A:
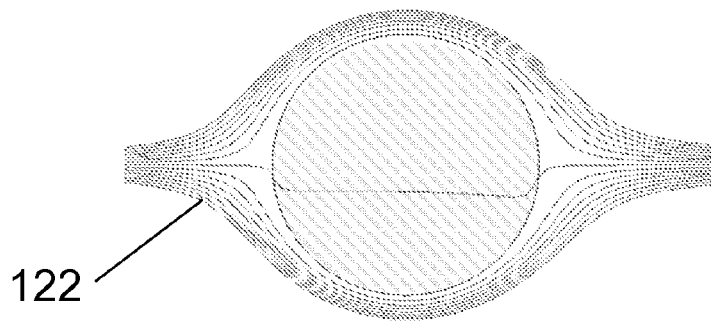
FIGS. 5A-5D show simulated streamlines around different shape obstacles.
Figure 5B:
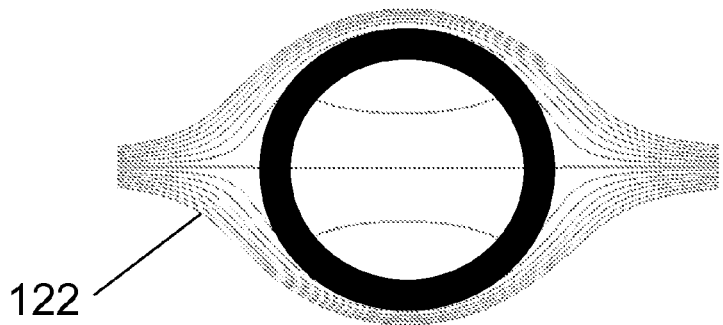
Figure 5C:
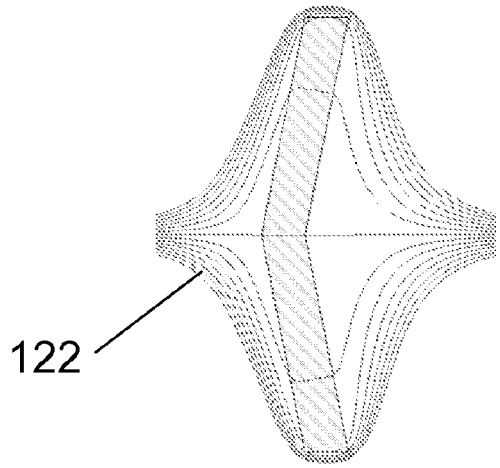
Figure 5D:
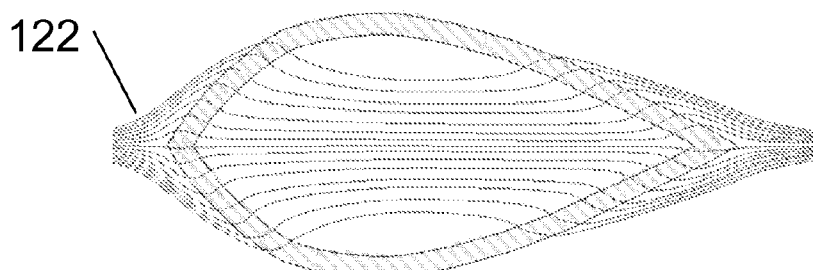
Figure 45A:
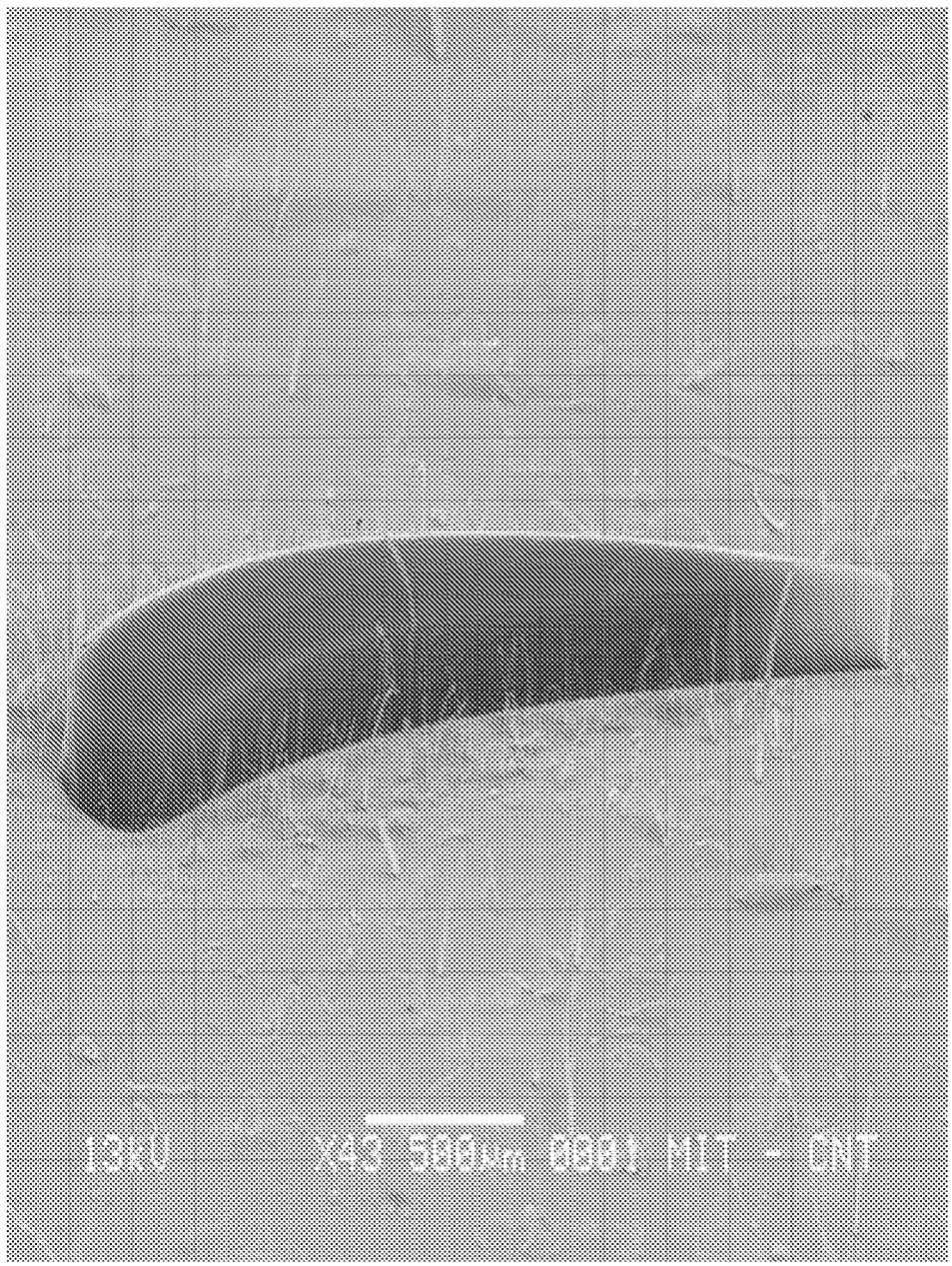
FIGS. 45A and 45B are micrographs of obstacles shaped as an asymmetric airfoil and as a hollow cylindrical post.
Figure 45B:
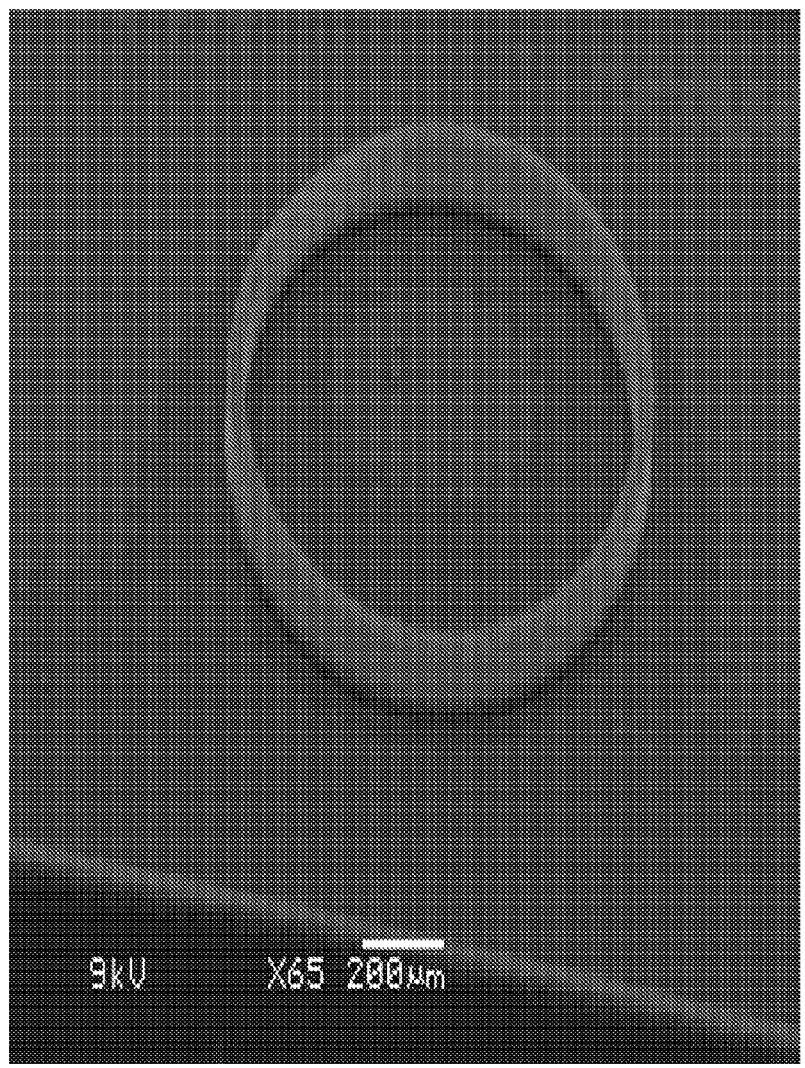

As noted elsewhere, the obstacles described herein can have a variety of cross-sectional shapes. FIG. 5A-FIG. 5D show streamlines 122 of flow around and through four types of obstacles 110. FIG. 5A shows a selectively permeable round post. FIG. 5B shows a hollow round post with a selectively permeable wall. FIG. 5C shows a chevron-shaped wall. FIG. 5D shows a hollow airfoil-shaped obstacle with a selectively permeable wall. FIG. 45A is an SEM (scanning electron micrograph) of an asymmetrical airfoil-shaped obstacle, and FIG. 45B is an SEM of a hollow cylindrical obstacle. Each of the obstacles in FIGS. 45A and 45B comprises a plurality of substantially aligned carbon nanotubes.

The streamlines in FIGS. 5A-5D were simulated using COMSOL. In each of the simulations in FIGS. 5A-5D, the streamlines extend from common starting points. Porous media flow was simulated using Darcy's law and the interface between porous and free media flow was calculated using Brinkman's equations. In these simulations, the obstacles were assigned permeability values of $2 \times 10^{-13}$ m$^2$. As illustrated in FIGS. 5A-5D, geometrical alterations to obstacles can increase or decrease the amount of interaction between the obstacles and incoming particles.

Arrays of Obstacles

FIG. 6 shows obstacles with other shapes (e.g., triangular arrays of obstacles with circular cross-sections, with triangular cross-sections having a point oriented upstream, with D-shaped cross-sections with their flat faces oriented downstream, with trapezoidal cross-sections; with rectangular cross-sections; with airfoil cross-sections. Any of the shapes can be used both singularly and in the form of arrays for particle capture. It is expected that compared to solid obstacle arrays of the same geometry, the selectively permeable obstacle arrays will achieve higher efficiency of capture. As a result, smaller arrays of selectively permeable obstacles can be used to achieve the same capture efficiency as a solid obstacle array. FIGS. 38A-D and 39A-D and Example 4 demonstrate this. This advantage in the reduction of array size has the benefits of smaller device area, higher concentration of captured particles, and faster detection time should downstream detection follow.

Impact of Obstacle Arrangement on Capture Efficiency

Figure 8A:
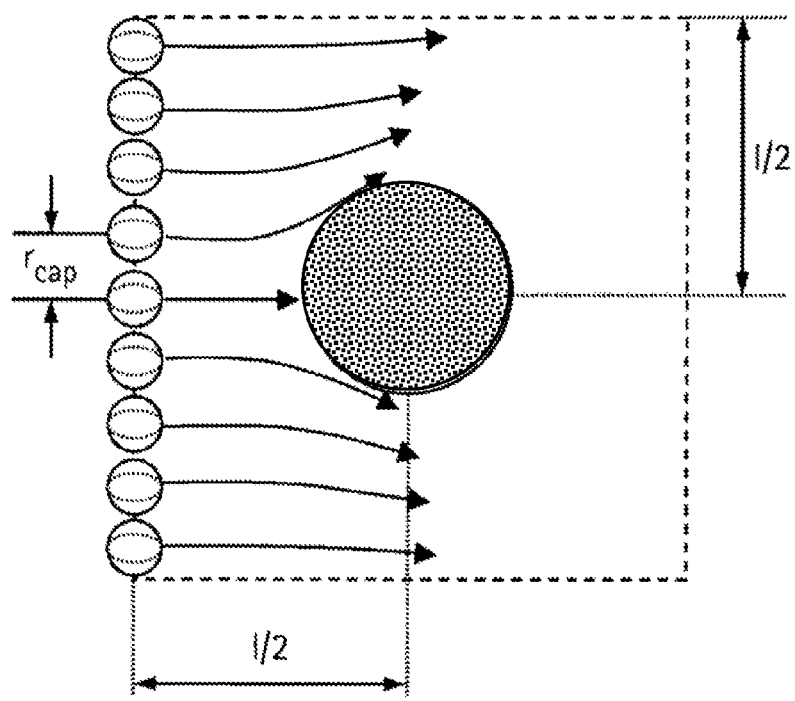
FIG. 8A is a schematic representation of the flow around a solid obstacle in a square array.
Figure 8B:
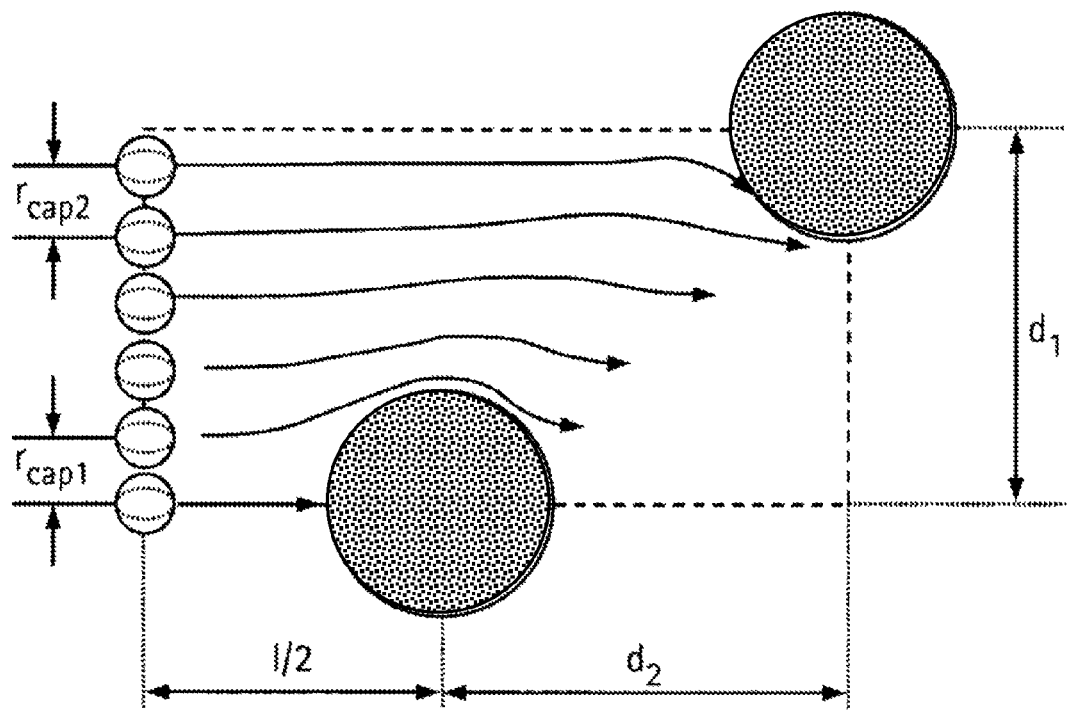
FIG. 8B is a schematic representation of the flow around two solid obstacles in a diagonal array.

FIG. 7A and FIG. 7B show exemplary arrangements of obstacles. The capture efficiency of such arrangements of obstacles can be calculated by computing the hydrodynamic efficiency ($\eta$) and the probability of adhesion. The hydrodynamic efficiency can be determined as the ratio of the capture radius to the half-distance between the cylinders (FIG. 8A and FIG. 8B). For the square array, $\eta=(2r_{cap}/1)*100\%$, and for other arrays, $\eta=((r_{cap1}+r_{cap2})/d_1)*100\%$, where $d_1=d_2=1/\sqrt{2}$ for a diagonal square array, and $d_1=1$ sqrt(3)/2, $d_2=\frac{1}{2}$ for a triangular array. The probability of adhesion represents the fraction of cells that can resist the applied force on the cell assuming an average of 1.5 bonds per cell and 75 pN per bond.

The capture efficiency for a square array (FIG. 7A) and a triangular array (FIG. 7B) was previously calculated for solid posts and are summarized below. A more detailed discussion and presentation of results can be found in U.S. Pat. Pub. No. 2006/0134599. The use of selectively permeable obstacles as described herein will increase the capture radius of individual posts (see the Examples described herein) but, qualitatively, the relative effects of obstacle arrangement on capture efficiency is anticipated to be similar for both permeable and solid posts in certain flow regimes, whereas in other flow regimes, it is anticipated to be quite different, e.g., turbulence, vorticity, etc.

For the triangular array, more cells adhered to the second column of obstacles than the first set. The efficiency declines as the spacing between obstacles increases. As the spacing between solid obstacles increases, there is a larger region outside the capture radius and the cells never contact the obstacles. Further, for the flow rates examined for solid posts (0.25-1 mL/h), the overall probability of adhesion is high because the force per cell is less than the force to break the bonds.

Figure 9:
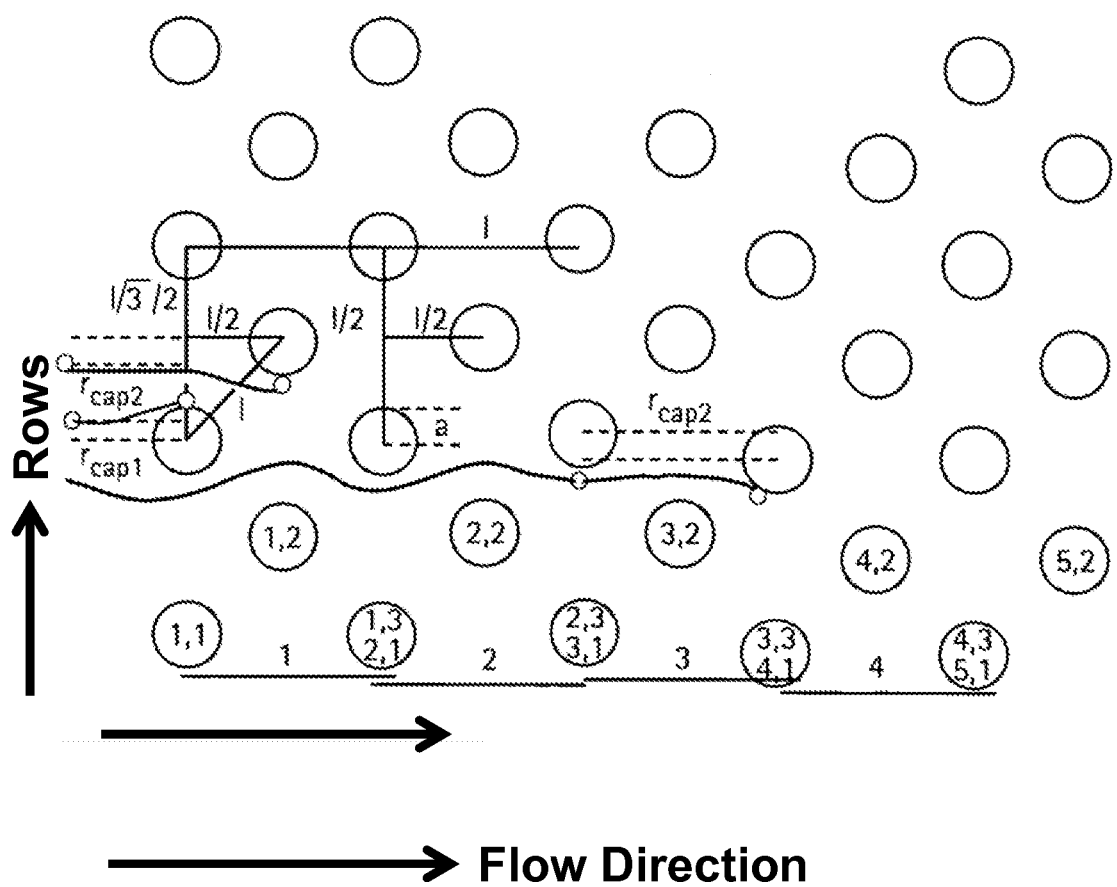
FIG. 9 is a schematic illustration of a so-called triangular array of round posts. Within this array, the posts are arranged in evenly spaced rows and columns, and there is a downward shift of the rows starting in the seventh column from the left.

A repeating triangular array of solid obstacles provides limited capture of target cells, because most of the capture occurs in the first few rows. The reason for this is that the flow field becomes established in these rows and repeats. The first capture radius does not produce much capture whereas most of the capture is within the second capture radius (FIG. 9). Once cells within the capture radii are captured, the only way in which capture could occur is through cell-cell collisions to shift cells off their streamlines or secondary capture. With reference to FIG. 9, to enhance capture with a solid post array, after the flow field is established, the rows can be shifted in the vertical direction (normal to flow) by a distance equal to $r_{cap2}=0.339$ 1. The first six columns form two regular regions of equilateral triangles. This allows the flow to be established and be consistent with the solution for an equilateral triangular array. To promote capture of cells that fall outside $r_{cap2}$, the seventh column is shifted downward by a distance $r_{cap2}$. All columns are separated by a distance equal to ½. A cell which falls outside $r_{cap2}$ is shown being captured by the first obstacle in the fourth triangle (seventh column).

The obstacles can also be arranged in different patterns. Examples of possible obstacle shapes and patterns are discussed in more detail in WO 2004/029221. The obstacles can also be arranged to provide other functionalities. For example, the obstacles can be arranged to provide different preferential flow directions for particles of different sizes.

Figure 10A:
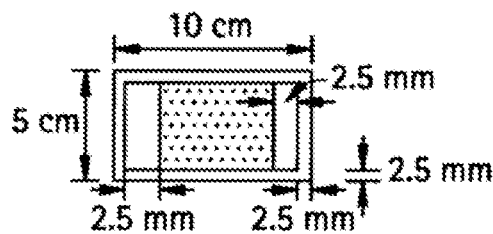
FIGS. 10A-C are a series of related illustrations of an array of obstacles in the form of microposts in which the columns of microposts are offset from each other in adjacent rows.
Figure 10B:
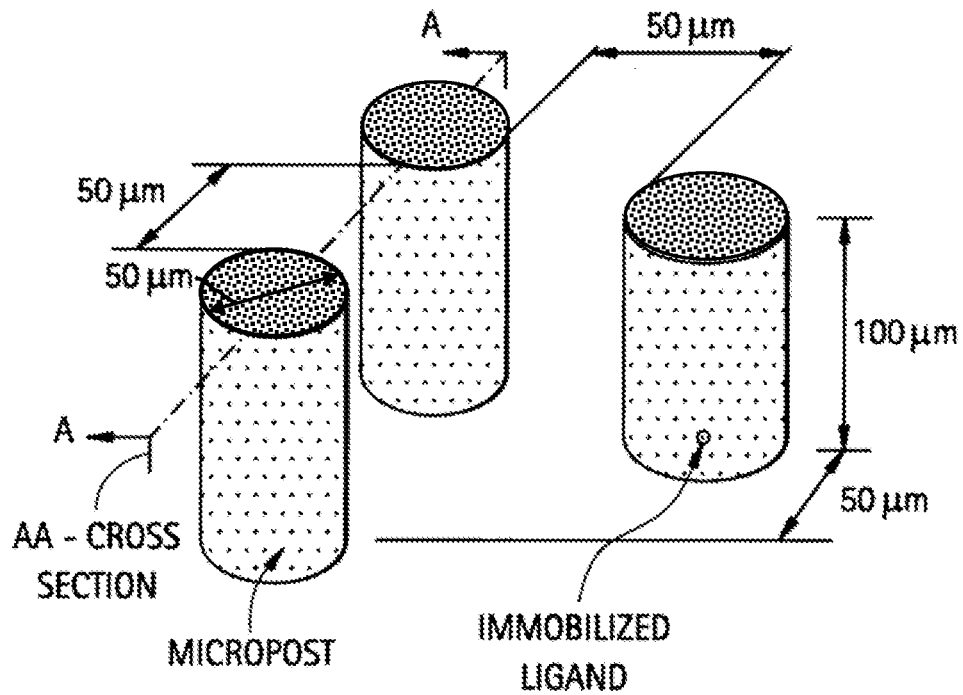
Figure 10C:
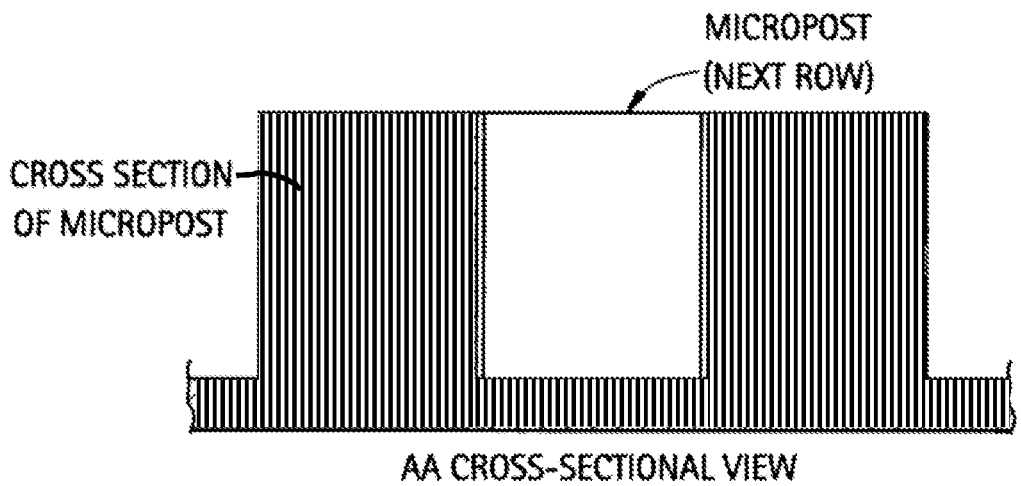

FIG. 10 shows some possible geometries of obstacles. In one example, obstacles are etched on a surface area of 2 cm×7 cm on a substrate with overall dimensions of 2.5 cm×7.5 cm. A rim of 2 mm is left around the substrate for bonding to the top surface to create a closed chamber. In one embodiment, obstacle diameter is 50 µm with a height of 100 µm. Obstacles can be arranged in a two-dimensional array of rows with a 100 µm distance from center-to-center. This arrangement provides 50 µm openings for cells to flow between the obstacles without being mechanically squeezed or damaged. The obstacles in one row are desirably shifted, e.g., 50 μm with respect to the adjacent rows. This alternating pattern can be repeated throughout the design to ensure increased collision frequency between cells and obstacles. The diameter, width, or length of the obstacles can be at least 5, 10, 25, 50, 75, 100, or 250 μm and at most 500, 250, 100, 75, 50, 25, or 10 μm. The gap size between obstacles can be at least 10, 25, 50, 75, 100, 250, 500, or 750 μm and at most 1000, 750, 500, 250, 100, 75, 50, or 25 μm. In some embodiments, the gap size can be just a few nanometers or even no gap, and the obstacles can be elongate and be several hundred microns long, e.g., as wide as a channel. Table 2 lists exemplary spacings based on the diameter of the obstacles.

TABLE 2

Exemplary Spacing for Obstacles

| Obstacle diameter (μm) | Spacing between obstacles (μm) |
|---|---|
| 100 | 50 |
| 100 | 25 |
| 50 | 50 |
| 50 | 25 |
| 10 | 25 |
| 10 | 50 |
| 10 | 15 |

Exemplary Capture Device with Posts

Figure 11:
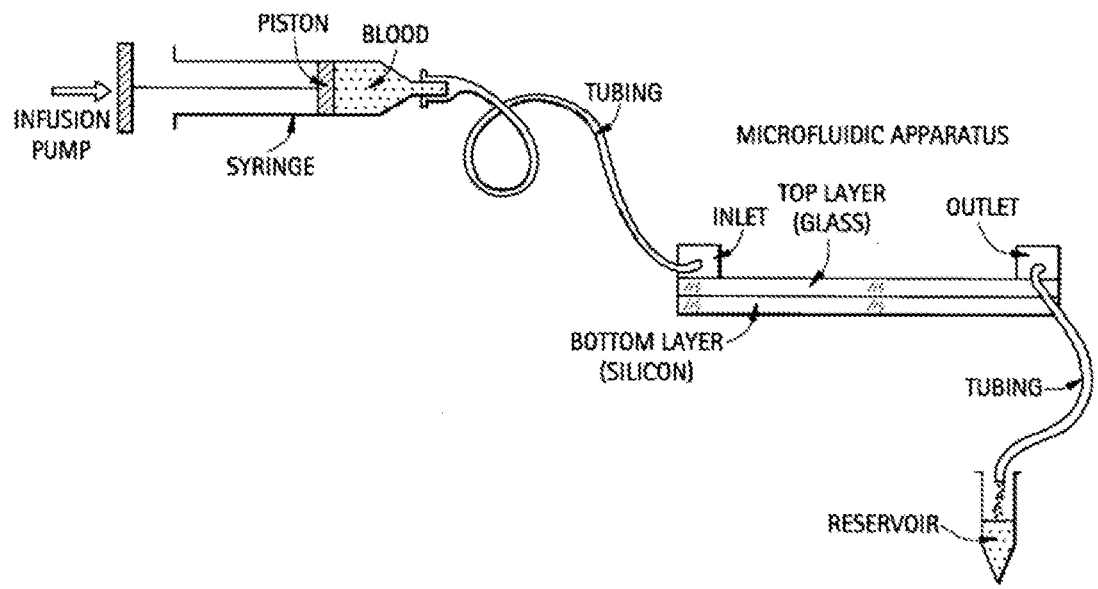
FIG. 11 is a schematic diagram of a cell binding device.
Figure 12:
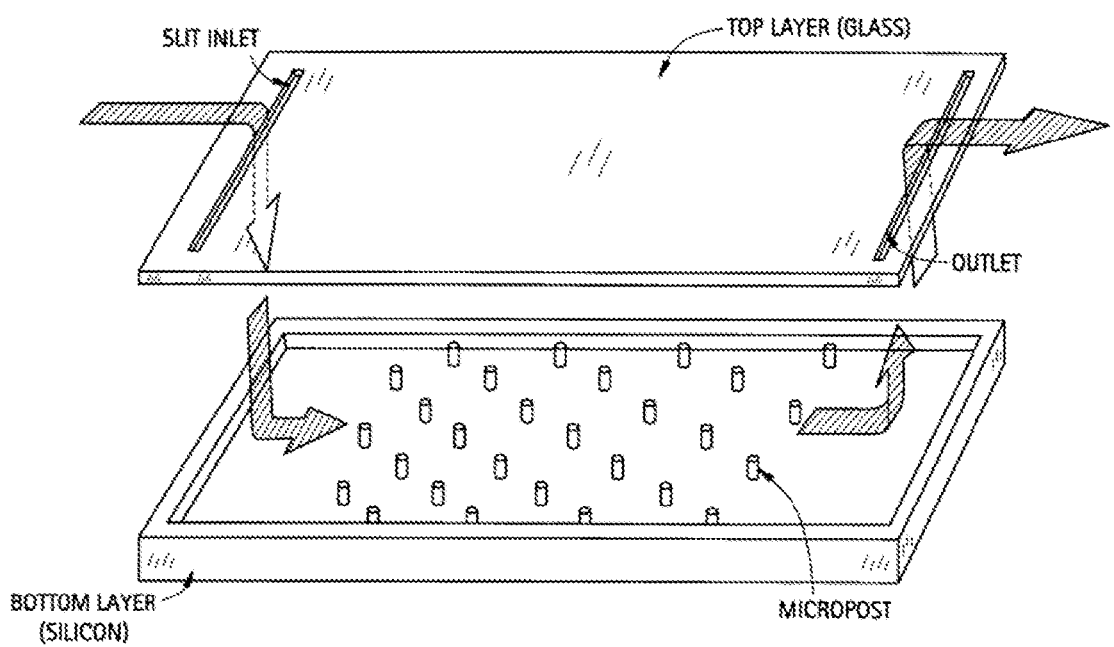
FIG. 12 is an exploded view of a cell binding device of FIG. 11.

An exemplary device is a flow apparatus having a flat-plate channel through which cells flow; such a device is described in U.S. Pat. No. 5,837,115. FIG. 11 shows an exemplary system including an infusion pump to perfuse a mixture of cells, e.g., blood, through the microfluidic device. Other pumping methods, as described herein, can be employed. The device can be optically transparent, or have transparent windows, for visualization of cells during flow through the device. The device contains obstacles distributed, e.g., in an ordered array or randomly, throughout the flow chamber. The top and bottom surfaces of the device are desirably parallel to each other. This concept is depicted in FIG. 12.

The overall size of an exemplary device is shown in FIG. 10 (top inset). The length is 10 cm and the width is 5 cm. The area that is covered with obstacles is 9 cm×4.5 cm. The design is flexible enough to accommodate larger or smaller sizes for different applications.

The overall size of the device can be smaller or larger, depending on the flow throughput and the number of cells to be depleted (or captured). A larger device could include a greater number of obstacles and a larger surface area for cell capture. Such a device can be necessary if the amount of sample, e.g., blood, to be processed is large.

The obstacles can be either part of the bottom or the top surface and desirably define the height of the flow channel. It is also possible for a fraction of the obstacles to be positioned on the bottom surface, and the remainder on the top surface. The obstacles can contact both the top and bottom of the chamber, or there can be a gap between an obstacle and one surface. The obstacles can be coated with a binding moiety, e.g., an antibody, a charged polymer, a molecule that binds to a cell surface receptor, an oligo- or polypeptide, a viral or bacterial protein, a nucleic acid, or a carbohydrate, that binds a population of cells, e.g., those expressing a specific surface molecule, in a mixture. Other binding moieties that are specific for a particular type of cell are known in the art. In an alternative embodiment, the obstacles are fabricated from a material to which a specific type of cell binds. Examples of such materials include organic polymers (charged or uncharged) and carbohydrates. Once a binding moiety is coupled to the obstacles, a coating, as described herein, can also be applied to any exposed surface of the obstacles to prevent non-specific adhesion of cells to the obstacles.

The top layer can be made of, for example, glass, and has two slits drilled ultrasonically for inlet and outlet flows. The slit inlet/outlet dimensions are, for example, 2 cm long and 0.5 mm wide. A manifold can then be incorporated onto the inlet/outlet slits. The inlet manifold accepts blood cells from an infusion syringe pump or any other delivery vehicle, for example, through a flexible, biocompatible tubing. Similarly the outlet manifold is connected to a reservoir to collect the solution and cells exiting the device.

The inlet and outlet configuration and geometry can be designed in various ways. For example, circular inlets and outlets can be used. An entrance region devoid of obstacles is then incorporated into the design to ensure that blood cells are uniformly distributed when they reach the region where the obstacles are located. Similarly, the outlet is designed with an exit region devoid of obstacles to collect the exiting cells uniformly without damage.

Size-Based Separation

Other devices for the separation of particles rely on sized-based separation with or without simultaneous cell binding. Some size-based separation devices use sieves that selectively allow passage of particles based on their size, shape, or deformability. Other size-based separation devices include one or more arrays of obstacles that cause lateral displacement of CTCs and other components of fluids, thereby offering mechanisms of enriching or otherwise processing such components. The array(s) of obstacles for separating particles according to size typically define a network of gaps, wherein a fluid passing through a gap is divided unequally into subsequent gaps. Both sieve and array sized-based separation devices can incorporate the selectively permeable obstacles as described above with respect to cell-binding devices.

Sieve-Based Size Separation

Some size-based separation devices use sieves that selectively allow passage of particles based on their size, shape, or deformability. The size, shape, or deformability of the pores in the sieve determines the types of cells that can pass through the sieve. Two or more sieves can be arranged in series or parallel, e.g., to remove cells of increasing size successively.

FIG. 13 shows the schematic of a low shear stress filtration device that includes selectively permeable obstacles to form the sieve obstacles. The obstacles are functionalized with binding moieties specific for bioparticles that are smaller than the average size of the void spaces between nanostructures forming the nanopermeable obstacle, for example, viruses, exosomes, plasma proteins, and cell-free DNA. The device has one inlet channel which leads into a diffuser, which is a widened portion of the channel. Typically, the channel widens in a V-shaped pattern. The diffuser contains two sieves having pores shaped to separate, for example, smaller RBCs and platelets from blood, while enriching the population of WBCs and fetal RBCs. The diffuser geometry widens the laminar flow streamlines forcing more cells to come in contact with the sieves while moving through the device. The device contains 3 outlets, two outlets collect cells that pass through the sieves, e.g., the RBCs and platelets, and one outlet collects the enriched WBCs and fetal RBCs.

The diffuser device typically does not ensure 100% depletion of RBCs and platelets. Initial RBC:WBC ratios of 600:1 can, however, be improved to ratios around 1:1. Advantages of this device are that the flow rates are low enough that shear stress on the cells does not affect the phenotype or viability of the cells and that the barriers ensure that all the large cells (i.e., those unable to pass through the sieves) are retained such that the loss of large cells is minimized or eliminated. This property also ensures that the population of cells that pass through sieve do not contain large cells, even though some smaller cells can be lost. Widening the diffuser angle will result in a larger enrichment factor. Greater enrichment can also be obtained by the serial arrangement of more than one diffuser where the outlet from one diffuser feeds into the inlet of a second diffuser. Widening the gaps between the obstacles might expedite the depletion process at the risk of losing large cells through the larger pores in the sieves. For separating maternal red blood cells from fetal nucleated red blood cells, an exemplary spacing is 2-4 µm.

The device as described herein is a continuous flow cell sorter, e.g., that separates larger WBCs and fetal RBCs from blood. The location of the sieves in the device is chosen to ensure that the maximum number of particles come into contact with the sieves, while at the same time avoiding clogging and allowing for retrieval of the particles after separation. In general, particles are moved across their laminar flow lines which are maintained because of extremely low Reynolds number in the channels in the device, which are typically micrometer sized.

A variety of obstacle sizes, geometries, and arrangements can be used in devices as described herein. Different shapes of obstacles, e.g., those with circular, square, rectangular, oval, or triangular cross sections, can be used in a sieve. The gap size between the obstacles and the shape of the obstacles can be optimized to ensure fast and efficient filtration. For example, the size range of the RBCs is on the order of 5-8 µm, and the size range of platelets is on the order of 1-3 µm. The size of all WBCs is greater than 10 µm. Large gaps between obstacles increase the rate at which the RBCs and the platelets pass through the sieve, but increased gap size also increases the risk of losing WBCs. Smaller gap sizes ensure more efficient capture of WBCs, but also a slower rate of passage for the RBCs and platelets. Depending on the type of application different geometries can be used.

One problem associated with devices as described herein is clogging of the sieves. This problem can be reduced by appropriate sieve shapes and designs and also by treating the sieves with non-stick coatings such as bovine serum albumin (BSA) or polyethylene glycol (PEG), as described herein. One method of preventing clogging is to minimize the area of contact between the sieve and the particles.

Array-Based Size Separation

Examples of array-based size separation are discussed in detail in U.S. Pat. Pub. No. 2007/0026413. In general, the devices include one or more arrays of selectively permeable obstacles that cause lateral displacement of large particles such as, for example, CTCs and other components suspended in fluid samples, thereby offering mechanisms of enriching or otherwise processing such components, while also offering the possibility of selectively binding other, smaller particles that can penetrate into the voids in the dense matrices of nanotubes that make up the obstacles. Other devices that employ such selectively permeable obstacles for this purpose are described, e.g., in Huang et al., Science 304, 987-990 (2004) and U.S. Publication No. 20040144651. The devices for separating particles according to size typically employ an array of obstacles that define a network of gaps, wherein a fluid passing through a gap is divided unequally into subsequent gaps. The array includes a network of gaps arranged such that fluid passing through a gap is divided unequally, even though the gaps can be identical in dimensions. It is anticipated that fluid flow through the permeable obstacles of such an array is sufficiently smaller than fluid flow through the obstacles that the lateral movement of particles too large to enter the permeable obstacles approximates that observed for arrays with solid obstacles.

Figure 15:
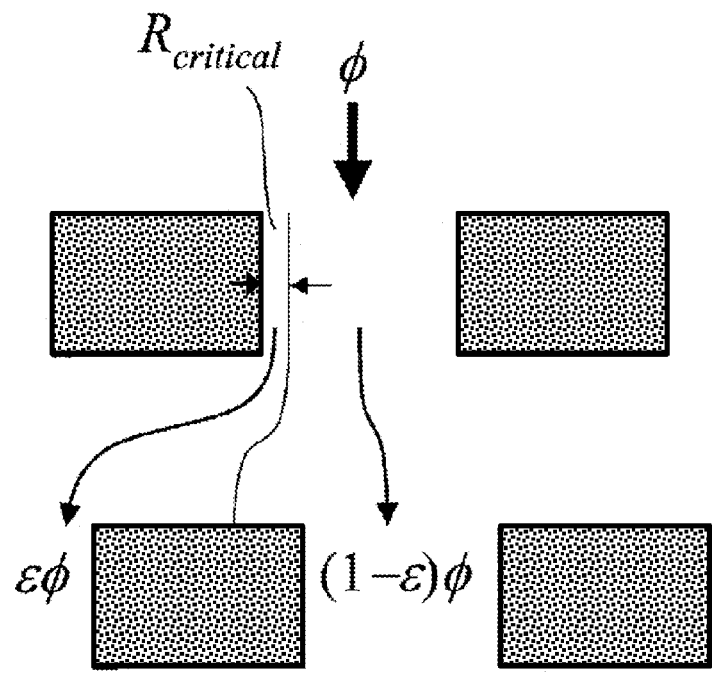
FIG. 15 is a schematic illustration showing the unequal division of the flow of a fluid sample through a gap around obstacles in subsequent rows.

The methods use a flow that carries cells to be separated through the array of gaps. The flow is aligned at a small angle (flow angle) with respect to a line-of-sight of the array. Cells having a hydrodynamic size larger than a critical size migrate along the line-of-sight, i.e., laterally, through the array, whereas those having a hydrodynamic size smaller than the critical size follow the average flow direction. Flow in the device occurs under laminar flow conditions. Devices are optionally configured as continuous-flow devices. The critical size is a function of several design parameters. With reference to the obstacle array in FIG. 14A-FIG. 14C, each row of selectively permeable obstacles is shifted horizontally with respect to the previous row by $\Delta\lambda$, where $\lambda$ is the center-to-center distance between the obstacles (FIG. 14A). The parameter $\Delta\lambda/\lambda$ (the "bifurcation ratio," $\epsilon$) determines the ratio of flow bifurcated to the left of the next obstacle. In FIG. 14A-FIG. 14C, $\epsilon$ is ⅓, for the convenience of illustration. In general, if the flux through a gap between two obstacles is $\phi$, the minor flux is $\epsilon\phi$, and the major flux is $(1-\epsilon)\phi$ (FIG. 15). In this example, the flux through a gap is divided essentially into thirds (FIG. 14B). While each of the three fluxes through a gap weaves around the array of obstacles, the average direction of each flux is in the overall direction of flow. FIG. 14C illustrates the movement of particles sized above the critical size through the array. Such particles move with the major flux, being transferred sequentially to the major flux passing through each gap.

Figure 16:
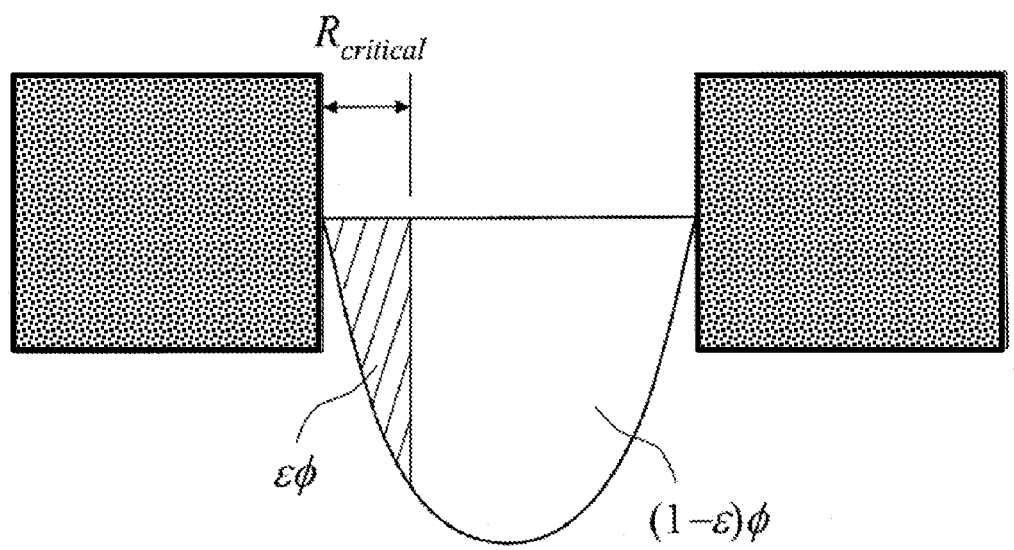
FIG. 16 is a schematic depiction of how the size of the radius of a particle relates to the flow profile, which is parabolic in this example.

Referring to FIG. 15, for solid obstacles, the critical size is approximately $2R_{critical}$, where $R_{critical}$ is the distance between the stagnant flow line and the obstacle. If the center of mass of a particle, e.g., a cell, falls within $R_{critical}$, the particle would follow the major flux and move laterally through the array. $R_{critical}$ can be determined if the flow profile across the gap is known (FIG. 16); it is the thickness of the layer of fluids that would make up the minor flux. For a given gap size, d, $R_{critical}$ can be tailored based on the bifurcation ratio, $\epsilon$. In general, the smaller $\epsilon$, the smaller $R_{critical}$.

Figure 17:
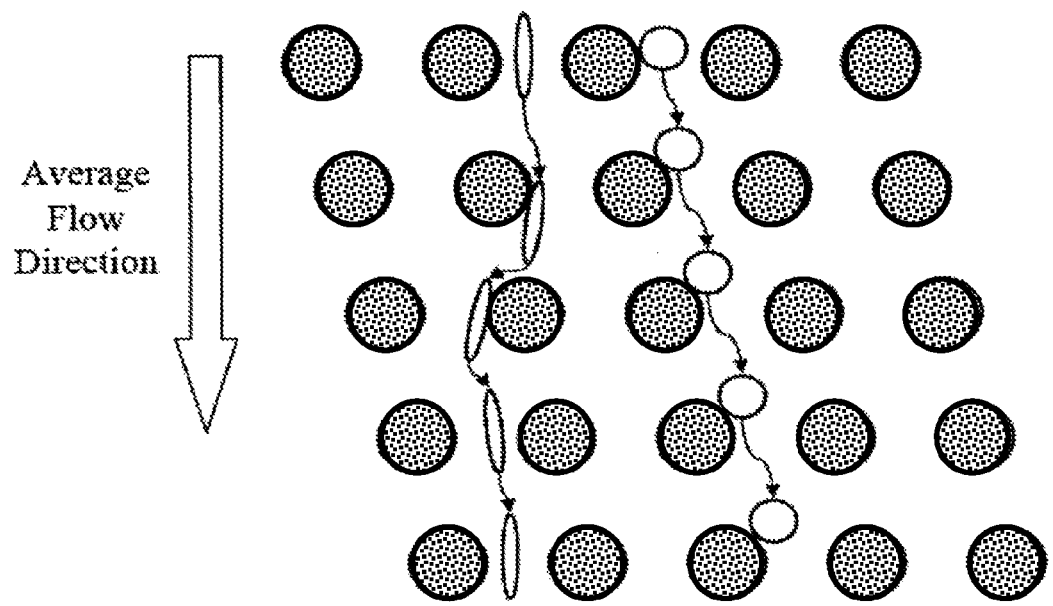
FIG. 17 is an illustration of how shape of a particle (e.g., elongate vs. round) affects the movement of particles through a device.
Figure 18:
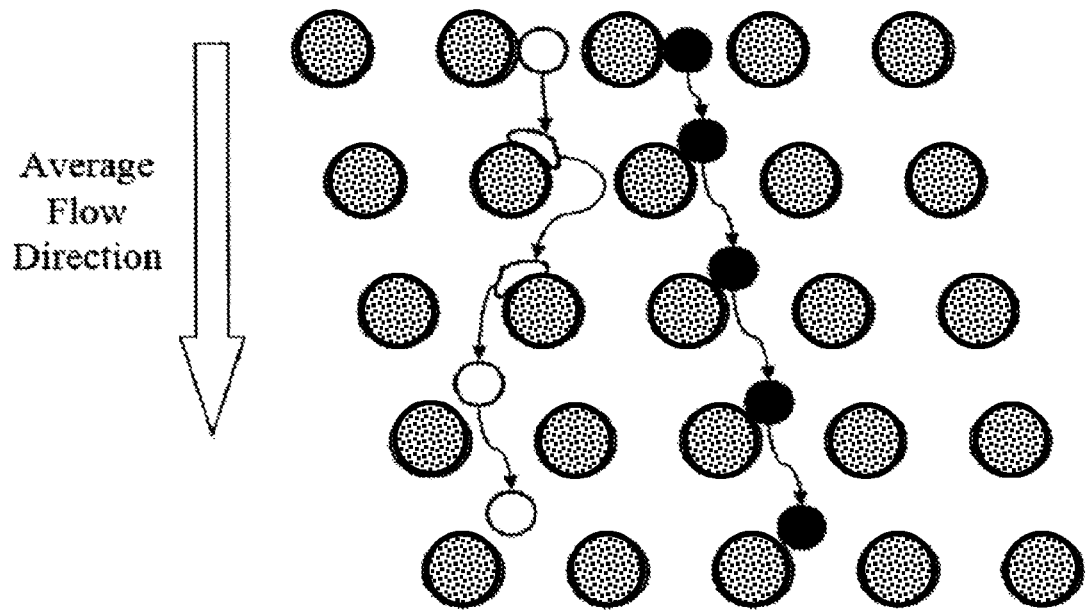
FIG. 18 is an illustration of how the level of deformability of a particle affects the movement of particles through a device.

In an array for lateral displacement, particles of different shapes behave as if they have different sizes (FIG. 17). For example, lymphocytes are spheres of ~5 µm diameter, and erythrocytes are biconcave disks of ~7 µm diameter, and ~1.5 µm thick. The long axis of erythrocytes (diameter) is larger than that of the lymphocytes, but the short axis (thickness) is smaller. If erythrocytes align their long axes to a flow when driven through an array of obstacles by the flow, their hydrodynamic size is effectively their thickness (~1.5 µm), which is smaller than the diameter of the lymphocytes. When an erythrocyte is driven through an array of obstacles by a hydrodynamic flow, it tends to align its long axis to the flow and behave like a ~1.5 µm-wide particle, which is effectively "smaller" than lymphocytes. The method and device can therefore separate cells according to their shapes, although the volumes of the cells could be the same. In addition, particles having different deformability behave as if they have different sizes (FIG. 18). For example, two particles having the same un-deformed shape can be separated by lateral displacement, as the cell with the greater deformability can deform when it comes into contact with an obstacle in the array and change shape. Thus, separation in the device can be achieved based on any parameter that affects hydrodynamic size including the physical dimensions, the shape, and the deformability of the particle.

Figure 19:
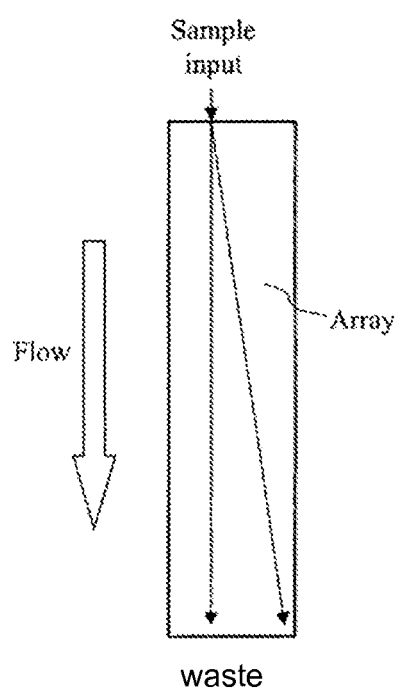
FIG. 19 is a schematic depiction of lateral displacement. Particles having a hydrodynamic size above the size of gaps between obstacles follow the diagonal arrow and move to the edge of the array, while particles having a hydrodynamic size below the gap size between obstacles follow the vertical arrow downwards and pass through the device without lateral displacement.

Referring to FIG. 19, feeding a mixture of particles, e.g., cells, of different hydrodynamic sizes from the top of the array and collecting the particles at the bottom, as shown schematically, produces two outputs, the product containing cells larger than the critical size, $2R_{critical}$, and waste containing cells smaller than the critical size. Although labeled "waste" in FIG. 19, particles below the critical size can be either collected or discarded, while the particles above the critical size can be similarly discarded or collected. In other embodiments, both types of outputs can also be desirably collected, e.g., when fractionating a sample into two or more sub-samples. Cells larger than the gap size will get trapped inside the array. Therefore, an array has a working size range. Cells have to be larger than a cut-off size ($2R_{critical}$) and smaller than a maximum pass-through size (array gap size) to be directed into the major flux. The "size range" of an array is defined as the ratio of maximum pass-through size to cut-off size.

In some cases, the gaps between obstacles are more than 15 microns, more than 20 microns, or less than 60 microns in size. In other cases, the gaps are between 20 and 100 microns in size.

In certain embodiments, a device as described herein can contain selectively permeable obstacles that include binding moieties, e.g., monoclonal anti-EpCAM antibodies or fragments thereof, that selectively bind to particular cell types, e.g., cells of epithelial origin, e.g., tumor cells. All of the obstacles of the device can include these binding moieties; alternatively, only a subset of the obstacles include them. Devices can also include additional modules that are fluidically coupled, e.g., a cell counting module or a detection module. For example, the detection module can be configured to visualize an output sample of the device. In addition, devices as described herein can be configured to direct cells in a selected size range in one direction, and other cells in a second direction. For example, the device can be configured to enrich cells having a hydrodynamic size greater than 12 microns, 14 microns, 16 microns, 18 microns, or even 20 microns from smaller cells in the sample. Alternatively, the device can enrich cells having a hydrodynamic size greater than or equal to 6 microns and less than or equal to 12 microns, e.g., cells having a hydrodynamic size greater than or equal to 8 microns and less than or equal to 10 microns, from other cells. The devices can also enrich cells having a hydrodynamic size greater than or equal to 5 microns and less than or equal to 10 microns from cells having a hydrodynamic size greater than 10 microns; alternatively, it can enrich cells having a hydrodynamic size greater than or equal to 4 microns and less than or equal to 8 microns from cells having a hydrodynamic size greater than 8 microns. In general, the device can be configured to separate two groups of cells, where the first group has a larger average hydrodynamic size than the second group.

In some embodiments, devices as described herein can process more than 20 mL of fluid per hour, or even 50 mL of fluid per hour.

As described above, a device as described herein typically contains an array of obstacles that form a network of gaps. For example, such a device can include a staggered two-dimensional array of obstacles, e.g., such that each successive row is offset by less than half of the period of the previous row. The device can also include a second staggered two-dimensional array of obstacles, which is optionally oriented in a different direction than the first array. In this case, the first array can be situated upstream of the second array, and the second array can have a higher density than the first array. Multiple arrays can be configured in this manner, such that each additional array has an equal or higher density of obstacles than any array upstream of the additional array.

Devices with Other Selectively Permeable Obstacles
Block Barriers

Figure 20A:
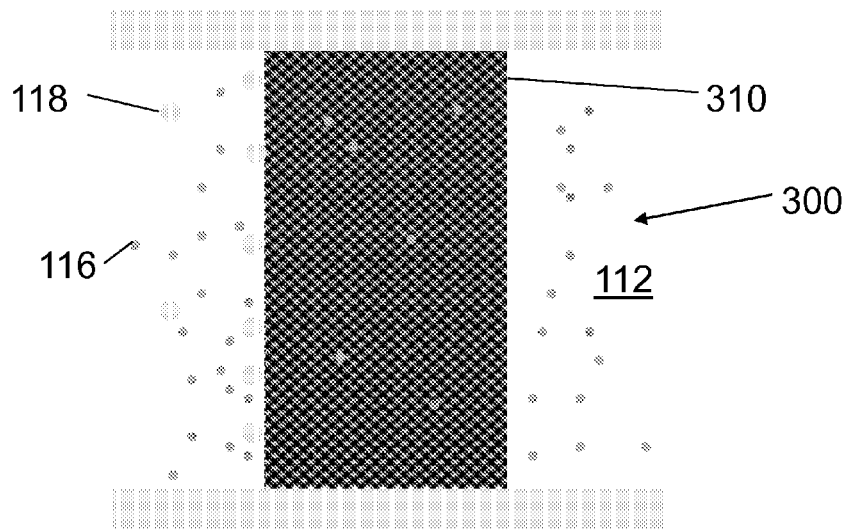
FIG. 20A and FIG. 20B are schematics of a device with a permeable obstacle that extends completely across a channel to mechanically block particles 118 that are larger than the voids in the obstacle while allowing particles that are smaller than voids to enter the obstacle.
Figure 20B:
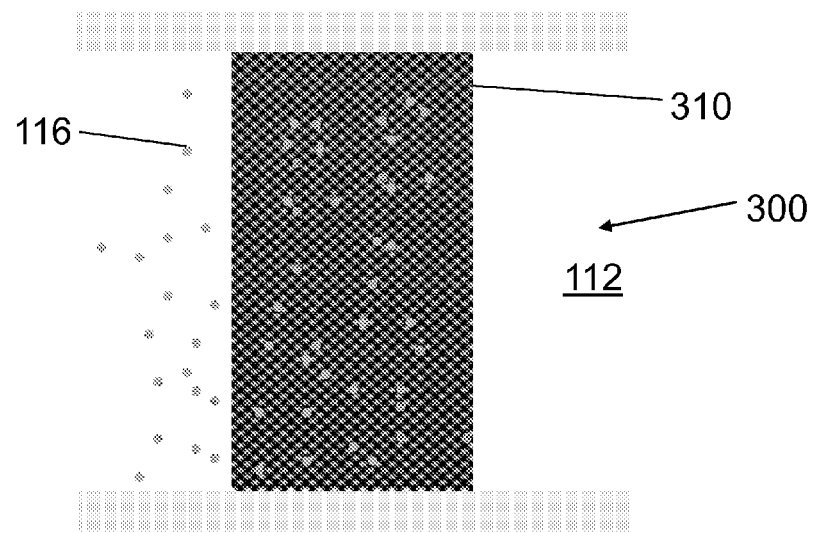

Referring to FIG. 20A and FIG. 20B, a device 300 can use a selectively permeable obstacle 310 that extends completely across a channel 112 to mechanically separate particles 118 that are larger than the voids in the obstacle (e.g., the spacing between individual nanotubes in the dense grouping), while allowing particles that are smaller than the voids to enter the obstacle. In some cases, the obstacle 310 is not functionalized and the particles 116 pass through the obstacle 310 (see FIG. 20A). In some cases, the obstacle 310 is functionalized and particles 116 can be captured inside the obstacle 310.

For example, a device 300 can be formed that combines the mechanical filtration with surface chemistry to efficiently capture small particles such as, for example, viruses, exosomes, lipid particles, DNA fragments, and proteins. The obstacle 310 can be formed with 100 nm spacing between individual nanotubes in the obstacle and functionalized, for example, with HCV E1 antibody to bind hepatitis C virus. The obstacle mechanically excludes 1 μm size particles (e.g., cells and bacteria), which are larger than the 80 nm spacing between individual nanotubes. The hepatitis C virus particles are typically about 50-100 nm in size and can flow into the obstacle 310. Since there are about $10^8$ individual carbon nanotubes per $mm^2$ of the dense grouping within the obstacle, creating a 400× increase in surface area inside a 100 μm height channel, particles traveling between the network of nanotubes will encounter a high degree of contact with the functionalized carbon nanotube sidewalls.

Buffer Exchange Barriers

Figure 21:
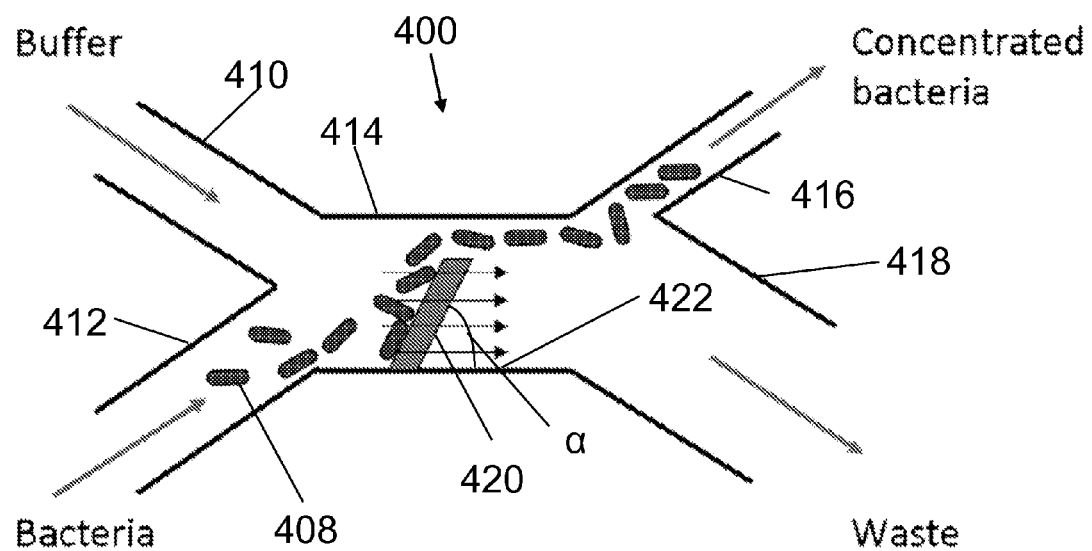
FIG. 21 is a schematic top view of a device incorporating a selectively permeable wall that causes lateral movement of particles from an original media to a buffer fluid. The selectively permeable wall extends outward from a side wall of the main channel at an angle α and is configured such that fluid flows through the wall, but the particles are deflected laterally. The wall is created extend far enough outward from the sidewall that the lateral movement of particles transfers the particles from the original media into the buffer fluid.

Referring to FIG. 21, a device 400 incorporating a selectively permeable barrier wall can be used to transfer particles 408, such as bacteria or cells, from a fluid such as, for example, a plasma or cell culture media to a clean buffer. The device 400 includes a buffer inlet 410 and a separate inlet 412 for the particles in their original media. The buffer and the original media flow into a main channel 414. Laminar flow conditions may be maintained such that the buffer and the original media stay substantially separate as the two fluids flow through the main channel 414 and out collection channel 416 and waste channel 418. The waste channel 418 is larger than the collection channel 416 such that buffer fluid from near the original media that can have experienced diffusive mixing with the original media is routed to the waste channel 418. A selectively permeable wall 420 extends outward from a side wall 422 of the main channel 414 at an angle α that can range between about 45 degrees and about 85 degrees (e.g., 50, 60, 70, 80 degrees, or greater). The wall 420 is configured such that fluid flows through the wall 420, but the particles 408 are deflected laterally. The wall 420 extends far enough outward from the sidewall 422 that the lateral movement of particles 408 transfers the particles 408 from the original media into the buffer fluid. The concentrated particles 408 in buffer fluid then flow out of main channel 414 into collection channel 416.

Continuous Flow Concentrators

Figure 22:
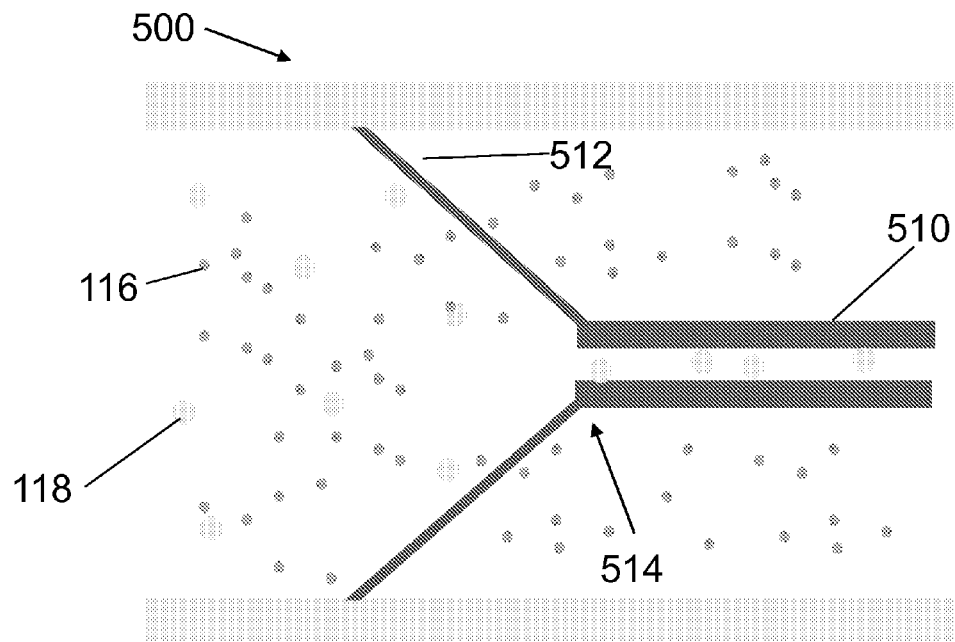
FIG. 22 is a schematic of a device with a micro-patterned Y-shaped nanopermeable funnel barrier for continuous separation and concentration of particles through mechanical separation. Large particles, which cannot pass through the barrier, are guided into a narrow neck of the barrier, whereas fluid and smaller particles efficiently pass through the barrier, ultimately resulting in a separation and concentration of the larger particles in the sample.

Referring to FIG. 22, a device 500 can include a micropatterned Y-shaped barrier 510 for continuous separation and concentration of particles through mechanical separating. In this configuration, large particles 118, which cannot pass through the selectively permeable barriers 510 and 512, are guided by a selectively permeable barrier 512 into a narrow neck 514 of the barrier 510, whereas fluid and smaller particles efficiently pass through the barrier, ultimately resulting in a concentration of the larger particles in the sample. The barrier 510 can be blocked against non-specific binding using, for example, with 0.5% Tween-20 in distilled water.

Concentration factors can be achieved by adjusting the ratio of the width of the passage formed by the selectively permeable barriers to the width of the overall channel, or by cascading several barriers.

For example, the device 500 can be configured to enrich cells having a hydrodynamic size greater than 12 microns, 14 microns, 16 microns, 18 microns, or even 20 microns from smaller cells in the sample. In some embodiments, much larger particles up to many tens or hundreds of microns or larger can be enriched. Alternatively, the device can enrich cells having a hydrodynamic size greater than or equal to 6 microns and less than or equal to 12 microns, e.g., cells having a hydrodynamic size greater than or equal to 8 microns and less than or equal to 10 microns, from other cells. The device can also enrich cells having a hydrodynamic size greater than or equal to 5 microns and less than or equal to 10 microns from cells having a hydrodynamic size greater than 10 microns; alternatively, it can enrich cells having a hydrodynamic size greater than or equal to 4 microns and less than or equal to 8 microns from cells having a hydrodynamic size greater than 8 microns. In general, the device can be configured to separate two groups of cells, where the first group has a larger average hydrodynamic size than the second group.

Microfluidic Devices that Include Multiple Modules

Multiple modules based on selectively permeable obstacles can be combined in multi-purpose/integrated devices for capture of multiple particle types. Such multi-purpose devices can be combinations of any of the previously mentioned obstacles arranged in parallel and/or in series.

In certain embodiments, a device can include an array of multiple posts arranged in a hexagonal packing pattern upstream of a block barrier. The posts and the block barrier can be functionalized with different binding moieties. In cancer monitoring applications, for example, the posts can be functionalized with anti-EPCAM antibody to capture circulating tumor cells (CTC) while block barrier 612 can be functionalized with anti-AChE to capture exosomes and DNA. In viral monitoring, for example, the posts can be functionalized with anti-CD3 to capture T cells, while block barrier can be functionalized with antibodies against viral particle surfaces to capture viruses.

In certain embodiments, a device can contain obstacles that include binding moieties, e.g., monoclonal anti-EpCAM antibodies or fragments thereof, that selectively bind to particular cell types, e.g., cells of epithelial origin, e.g., tumor cells. All of the obstacles of the device can include these binding moieties; alternatively, only a subset of the obstacles include them. Devices can also include additional modules, e.g., a cell counting module or a detection module, which are in fluid communication with the microfluidic channel device. For example, the detection module can be configured to visualize an output sample of the device. In addition, devices can be configured to direct cells in a selected size range in one direction, and other cells in a second direction.

The obstacles/modules can also be arranged in parallel to provide higher throughput. In some embodiments, devices can process more than 20 mL of fluid per hour, or even 50 mL of fluid per hour.

Methods of Manufacture of Devices with Selectively Permeable Obstacles

Figure 23:
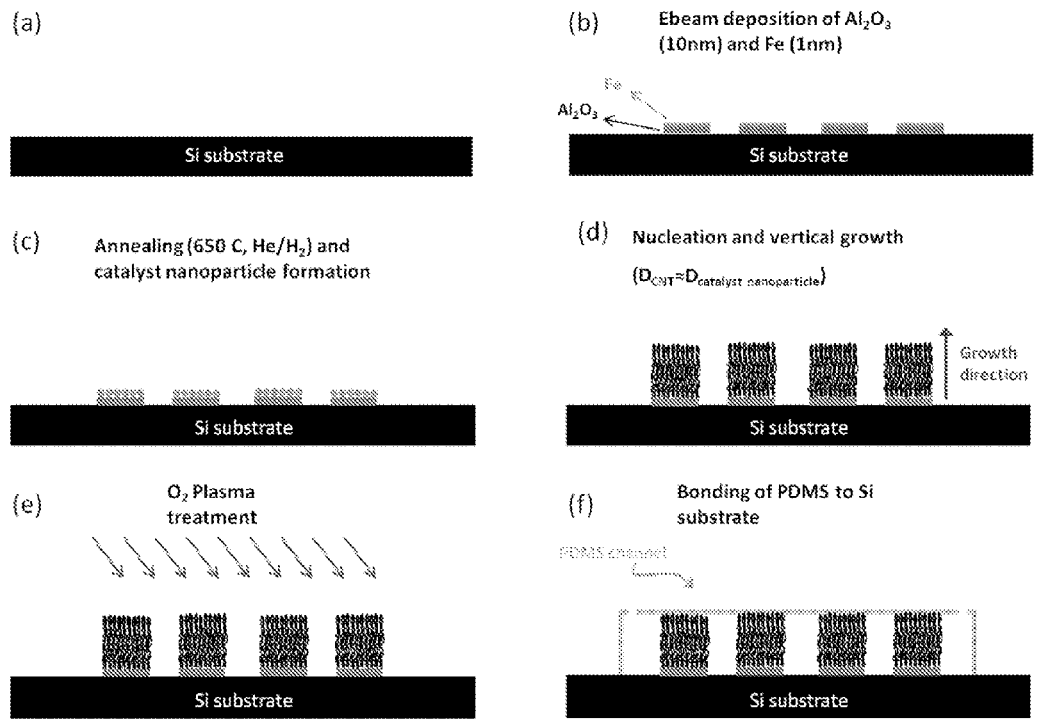
FIGS. 23a to 23f are a series of schematic side views illustrating an exemplary fabrication process for patterned nanopermeable carbon nanotube obstacles in microfluidic channels.

FIG. 23a to FIG. 23f show a schematic of an exemplary fabrication process, e.g., a process that can be used in the Examples described below. Similar to the example of a fabrication process described above, a substrate, such as a silicon wafer, e.g., a plain silicon wafer, e.g., a <100> 152 mm (6") silicon wafer (p-type, 1-10 Ω-cm, Silicon Quest International), is cleaned using standard techniques, such as with a "piranha" (3:1 $H_2SO_4$:$H_2O_2$) solution. The cleaned substrate is then patterned, e.g., by photolithography of a photoresist mask, for example, by using a 1.25 μm layer of image-reversal photoresist (AZ-5214E) (see FIG. 23a). A catalyst film, e.g., a 1/10 nm Fe/$Al_2O_3$ film, is then deposited by electron beam evaporation, e.g., in a single pump-down cycle using a Temescal® VES-2550® with a FDC-8000® Film Deposition Controller (FIG. 23b). Film thickness can be monitored during deposition, for example, by using a quartz crystal monitor. Catalyst areas for patterning are then removed by photoresist lift-off, by soaking the wafer in acetone for 10 minutes, e.g., with mild sonification (see FIG. 23c). Other catalysts selected for carbon nanotube growth can include Nickel, Gold, Ni/Co, copper, metal oxides such as Zirconia and any carbon nanotube growth catalyst or nano-positor or both.

Next, the catalyst film is annealed to form nanoparticles (FIG. 23c) and the carbon nanotubes are nucleated and grown vertically from this patterned catalyst (see FIG. 23d). For example, carbon nanotube growth can be performed in a 102 mm (4") ID quartz tube chemical vapor deposition (CVD) furnace (G. Finkenbeiner, Inc.) at atmospheric pressure using reactant gases of $C_2H_4$, $H_2$ and He (Airgas, 400, 1040, 1900 sccm, respectively). Catalyst annealing can be carried out in a reducing He/$H_2$ environment at 650° C., leading to the formation of catalyst nanoparticles about 10 nm in diameter (see FIG. 23c). $C_2H_4$ can then be introduced into the furnace to initiate carbon nanotube growth. In some instances, carbon nanotube growth can occur at a rate of approximately 100 μm/min until the flow of $C_2H_4$ is terminated (see FIG. 23d). The nanotubes grown using this method can be multi-walled (2-3 concentric walls), with a diameter of about 8 nm. In some instances, the carbon nanotubes can be spaced by approximately 80 nm with their morphology characterized by very good vertical alignment. Additional details regarding the formation of carbon nanotube obstacles are available in U.S. Pat. Pub. No. 2008/0075954.

The average distance between carbon nanotubes can be controlled, for example, using mechanical densification. It is also possible to control inter-CNT spacing by modifying materials (e.g., catalyst thickness), growth parameters (e.g., growth time, $H_2$ pre-treatment time), and or by coating the nanostructures so as to reduce the average inter-CNT spacing.

For example, FIG. 38A-FIG. 38C include a schematic illustration of one method of reducing the average distance between adjacent nanostructures. A plurality of nanostructures 710 are provided such that the long axes of the nanostructures, indicated by dashed lines 712, are substantially aligned relative to each other. Each nanostructure is positioned relative to an adjacent nanostructure at a distance so as to together define an average distance between adjacent nanostructures. In the embodiment illustrated in FIG. 38A, the average distance between adjacent nanostructures is roughly equal for each nanostructure. In other embodiments, the distances between adjacent nanostructures may vary. In addition, in some embodiments, the originally provided plurality of nanostructures extends a distance at least 10 times greater than the average distance between adjacent nanostructures in each of two orthogonal directions, each direction perpendicular to the long axes. In some cases, the plurality of nanostructures extends, in two orthogonal directions each perpendicular to the long axes, a distance at least 100 times greater, at least 1000 times greater, at least 10,000 times greater or longer than the average distance between adjacent nanostructures.

Figure 40A:
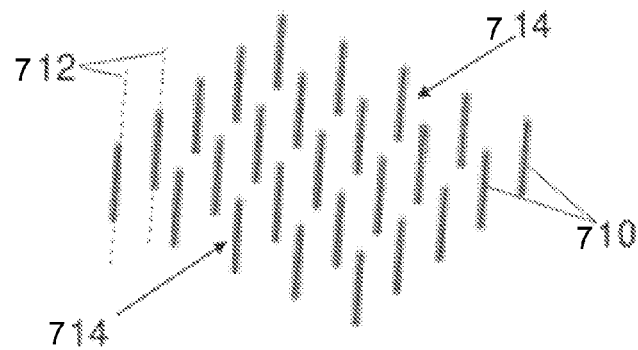
FIG. 40A-FIG. 40C are schematic diagrams illustrating the densification of nanostructures.
Figure 40B:
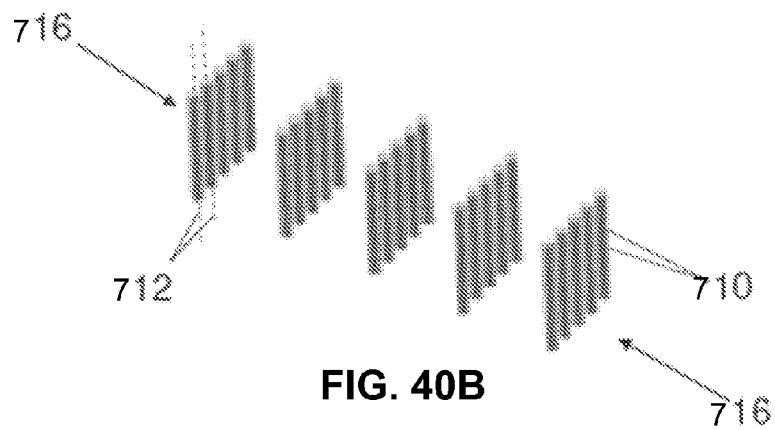

A first force with a component normal to the long axes of the nanostructures may be applied to the plurality of nanostructures. In the set of embodiments illustrated in FIG. 40A, the first force is applied as a compressive force in the direction of arrows 714. The application of the first force may result in the reduction of the average distance between the nanostructures. For example, FIG. 40B shows the resulting reduction of the average distance after the application of a first force in the direction of arrows 714.

The force described herein may be applied using any method known in the art. In some embodiments, a mechanical tool is used to apply the force to the plurality of nanostructures. For example, an operator may apply a flat surface of a tool (e.g., a plastic plunger) against the side of a plurality of nanostructures, and compress the nanostructures by hand. In some embodiments, the force may be applied using compression springs. For example, the plurality of nanostructures may be situated in an enclosed or semi-enclosed containment structure with one or more compression springs situated between the side of the plurality of nanostructures and an adjacent wall of the containment structure. Forces may be applied using other elements including, but not limited to, weights, machine screws, and/or pneumatic devices, among others. For example, in one set of embodiments, a plurality of nanostructures is arranged between two plates. A device (e.g., a machine screw, a spring, etc.) may be used to apply pressure against the sides of the nanostructures via the plates. In the case of a machine screw, for example, the nanostructures may be compressed between the plates upon rotating the screw. In still other embodiments, a liquid may be applied to the plurality of nanostructures and dried; upon drying, capillary forces may pull the nanostructures together, resulting in a reduction of the average distance between nanostructures. Other methods of applying forces to the plurality of nanostructures can be envisioned by one of ordinary skill in the art.

Figure 40C:
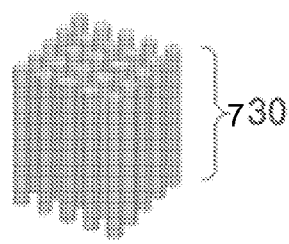

In some embodiments, a second force may be applied to the nanostructures. The second force may include a second component that is normal to the long axes of the nanostructures and orthogonal to the first component of the first force. As an example, in FIG. 40B, the second force may comprise a compressive force applied in the direction of arrows 716. The application of the second force may lead to a further reduction of the average distance between adjacent nanostructures. For example, FIG. 40C shows the resulting reduction of the average distance between adjacent nanostructures after the application of a second force in the direction of arrows 716.

The application of a first and/or second force may reduce the average distance between adjacent nanostructures by varying amounts. In some cases, the average distance between adjacent nanostructures is reduced by at least about 25%. In some instances, the average distance between adjacent nanostructures is reduced by at least about 50%, at least about 70%, at least about 80%, at least about 90%, at least about 95%, at least about 99%, or more. In some embodiments, the average distance between adjacent nanostructures may be reduced to less than about 80 nm, less than about 60 nm, less than about 40 nm, less than about 30 nm, less than about 20 nm, less than about 10 nm, less than about 5 nm, or less.

The permeability of the obstacles, e.g., in an array, can be tailored through manipulation of both material (e.g., catalyst thickness) and CNT growth process parameters (e.g., temperature ramp-up time, growth temperature). As described above, the permeability of porous materials is a function of both the obstacle size (D) of and the center-to-center distance (S) between each obstacle. Material and CNT growth process parameters can be controlled to manipulate both D and S, thus also modifying the structure's porosity and permeability.

In some embodiments, permeability manipulation can be performed by fine tuning the growth process conditions to increase the size and spacing between catalyst islands prior to CNT growth. This method consists of varying the $H_2$ pre-treatment time (PTT) to modify the Fe catalyst surface structure. In particular, the $H_2$ pre-treatment time was increased by 8 minutes compared to baseline growth, yielding larger intra-CNT spacing (~93 nm vs. 80 nm for baseline structures) and a 70% increase in fluid permeability ($\kappa=9.3*10^{-14}$ $m^2$ vs. $\kappa=5.4*10^{-14}$ $m^2$).

In some embodiments, the permeability can be controlled by controlling catalyst thickness to yield an obstacle with larger intra-CNT spacing. In particular, doubling the catalyst thickness (from 1 nm to 2 nm) resulted in an obstacle characterized by an average 98 nm intra-CNT spacing, and a 103% increase in forest permeability ($\kappa=1.1*10-13$ m2) compared to baseline devices.

In some embodiments, the methods described herein may be used to produce materials with high volume fractions of nanostructures. As used herein, the volume fraction of nanostructures within a material (e.g., a plurality of nanostructures, a nanocomposite, etc.) is calculated by dividing the sum of the volumes defined by the nanostructures by the total volume defined by the material. It should be noted that the volume defined by a nanostructure may contain some void space. For example, in the case of a hollow nanotube, the volume defined by the nanotube would include the interior void space within the tube. Forces may be applied to a plurality of nanostructures until the volume fraction of the nanostructures within the material is at least about 5%. In some instances, the forces are applied until the volume fraction of the nanostructures within the material is at least about 10%, at least about 20%, at least about 40%, at least about 60%, at least about 70%, at least about 75%, at least about 78%, or more. In some embodiments, the plurality of nanostructures may be provided as a self-supporting material. In other cases, the nanostructures may be attached to a substrate (e.g., a growth substrate). In some embodiments, the long axes of the nanostructures are substantially aligned and non-parallel to the substrate surface, having a thickness defined by the long axes of the nanostructures. The plurality of nanostructures may comprise any desirable aspect ratio. In some cases, a plurality of nanostructures may provided such that the plurality extends, in at least one dimension (e.g., in one dimension, in two orthogonal dimensions, etc.) substantially perpendicular to the long axes, a distance at least about 1.5 times greater, at least about 2 times greater, at least about 5 times greater, at least about 10 times greater, at least about 25 times greater, at least about 100 times greater, or more than a dimension substantially parallel to the long axes of the nanostructures. As a specific example, the plurality of nanostructures may constitute a thin-film such that the long axes of the nanostructures are substantially perpendicular to the largest surface of the film. A plurality of nanostructures may be provided, in some instances, such that the plurality extends, in at least one dimension substantially parallel to the long axes, a distance at least about 1.5 times greater, at least about 2 times greater, at least about 5 times greater, at least about 10 times greater, at least about 25 times greater, at least about 100 times greater, or more than a dimension substantially perpendicular to the long axes of the nano structures.

In some cases, at least 10%, at least about 20%, at least about 30%, at least about 40%, at least about 50%, at least about 60%, at least about 70%, or more of the nanostructures extend substantially through thickness of the plurality of nanostructures (e.g., wherein the thickness is defined as a dimension substantially parallel to the long axes of the nanostructures, such as dimension 730 in FIG. 40C).

In some cases, the nanostructures may be grown on a substrate. The nanostructures may be grown in the substrate using either a batch process or a continuous process. In one set of examples, the nanostructures may be synthesized by contacting a nanostructure precursor material with a catalyst material, for example, positioned on the surface of the growth substrate. In some embodiments, the nanostructure precursor material may be a nanotube precursor material and may comprise one or more fluids, such as a hydrocarbon gas, hydrogen, argon, nitrogen, combinations thereof, and the like. Those of ordinary skill in the art would be able to select the appropriate combination of nanotube precursor material, catalyst material, and set of conditions for the growth of a particular nanostructure. For example, carbon nanotubes may be synthesized by reaction of a $C_2H_4/H_2$ mixture with a catalyst material, such as nanoparticles of Fe arranged on an $Al_2O_3$ support. Examples of suitable nanostructure fabrication techniques are discussed in more detail in International Patent Application Serial No. PCT/US2007/011914, filed May 18, 2007, entitled "Continuous Process for the Production of Nanostructures Including Nanotubes," published as WO 2007/136755 on Nov. 29, 2007; International Patent Application Serial No. PCT/US2009/006352, filed Dec. 3, 2009, entitled "Multifunctional Composites Based on Coated Nanostructures," published as WO 2010/120273 on Oct. 21, 2010; and International Patent Application Serial No. PCT/US2010/002135, filed Jul. 30, 2010, entitled "Systems and Methods Related to the Formation of Carbon-Based Nanostructures," published as WO 2011/014258 on Feb. 3, 2011 which are incorporated herein by reference in its entirety.

In some embodiments in which the nanostructures are grown on a substrate, the set of substantially aligned nanostructures may be oriented such that the long axes of the nanostructures are substantially non-planar with respect to the surface of the growth substrate. In some cases, the long axes of the nanostructures are oriented in a substantially perpendicular direction with respect to the surface of the growth substrate, forming a nanostructure grouping or "forest." As described more fully below, an advantageous feature of some embodiments of the invention may be that the alignment of nanostructures in the nanostructure "forest" may be substantially maintained, even upon subsequent processing (e.g., application of a force to the forest, transfer of the forest to other surfaces, and/or combining the forests with secondary materials such as polymers, metals, ceramics, piezoelectric materials, piezomagnetic materials, carbon, and/or fluids, among other materials).

In some cases, providing a plurality of nanostructures comprises catalytically forming nanostructures on the surface of substrates. In other cases, the nanostructures may be provided as a self-supporting structure free of a growth substrate and/or any other material. In some cases, the precursor support material may be applied to a plurality of nanostructures that form a self-supporting structure, or the precursor support material may be applied to a plurality of nanostructures that are attached to a substrate. In addition, nanostructures may be solidified while attached to or apart from a growth substrate and/or any other support material.

The nanostructures may be fabricated, for example, by growing the nanostructures on the surface of a substrate, such that their long axes are aligned and non-parallel (e.g., substantially perpendicular) to the substrate surface, followed by formation of a conformal coating on the nanostructures. In some cases, the conformal coating may include a conducting polymer. The materials may be further processed to incorporate additional components, including thermoset or thermoplastic polymers.

Conformal coatings can be formed on materials (e.g., nanostructures) with little or substantially no change in the alignment, morphology and/or other characteristics of the underlying material. As used herein, a "conformal" coating refers to a coating formed on and attached or adhered to a material, wherein the coating physically matches the exterior contour of the surface area of the underlying material and the coating does not substantially change the morphology of the underlying material. That is, the coated material has a morphology that is essentially the same as the morphology of an essentially identical material lacking the polymer coating, under essentially identical conditions. It should be understood that the conformal coating may uniformly increase one or more dimensions (e.g., thickness) of the material, however, the overall morphology of the material remains essentially unchanged. For example, a conformal coating on a cylindrical carbon nanotube may form a cylindrically-shaped coating around the nanotube. Such properties may be advantageous, for example, when preservation of directionally dependent properties of a material (e.g., nanostructures) is desired and known coating techniques may produce undesired irregularities and morphological changes (e.g., due to agglomeration of nanostructures) that may adversely affect the anisotropy of the material. See, e.g., B. L. Wardle, H. Cebeci, S. Vaddiraju, and K. K. Gleason, "Multifunctional Composites Based on Conformally Coating CNT Arrays with Polymers," U.S. Provisional Patent Application No. 61/119,673, which is incorporated herein by reference in its entirety.

In some cases, conformal coatings may be formed on materials having a high aspect ratio (e.g., nanostructures). Additionally, the conformal coating may form a stable structure and may not delaminate from the surface of the nanostructures. In some cases, conformal coatings described herein may be formed on nanostructure assemblies having high density, wherein individual nanostructures are coated conformally over a substantial portion of the surface area of the nanostructures. In some cases, the conformal coating may have a substantially uniform thickness. A material having a "substantially uniform" thickness may refer to a material having a thickness which deviates less than 200%, less than 100%, less than 50%, less than 10%, less than 5%, or, in some cases, less than 1%, from an average thickness of the material, over a majority of the surface area of the nanostructure assembly. In some cases, the conformal coating may be substantially free of defects and/or voids, and may uniformly encapsulate the underlying material, or portion thereof.

The presence of a conformal coating attached to nanostructures can provide many advantageous properties to articles described herein. As used herein, the terms "attached" or "adhered" refer to attachment or adhesion via covalent bonds, non-covalent bonds (e.g., ionic bonds, van der Waals forces, etc.), and the like. In some cases, the conformal coating may enhance the mechanical stability and/or strength of the underlying material. In some cases, the conformal coating may be used to impart a desired property onto the underlying nanostructures in a manner that does not substantially disturb the alignment, spacing, morphology, or other desired characteristic of the nanostructures. For example, the article may exhibit a different property (e.g., thermal and/or electrical conductivity, heat transfer, hydrophobicity, hydrophilicity, etc.) when compared to an essentially identical article lacking the conformal coating, under essentially identical conditions. In an illustrative embodiment, a plurality of essentially non-conductive nanostructures may be provided, and, upon formation of a conformal coating comprising a conducting polymer, the nanostructures may exhibit enhanced electrical conductivity. In some cases, conductive nanostructures can be conformally coated with an essentially non-conductive material (e.g., an insulating polymer).

Formation of a conformal coating on a plurality of nanostructures may also effectively alter the surface energy of the nanostructures. In some cases, the conformal coating may increase the surface energy, relative to the uncoated, underlying material. In some cases, the conformal coating may decrease the surface energy, relative to the uncoated, underlying material. For example, the conformal coating may render the surface of the material, or portion thereof, hydrophobic or hydrophilic, as determined by contact angle measurements.

The conformal coating may be formed using various methods, including chemical vapor deposition, and from any suitable material. In some embodiments, the material may be polymeric. The conformal coating may be conductive, non-conductive, semiconductive, or the like. In some embodiments, the conformal coating may comprise a conducting polymer, including polyarylenes, polyarylene vinylenes, polyarylene ethynylenes, and the like. Examples of such polymers include polythiophenes, polypyrroles, polyacetylenes, polyphenylenes, substituted derivatives thereof, and copolymers thereof. In some embodiments, the polymer may include polypyrrole (PPY), poly(3,4-ethylenedioxythiophene) (PEDOT), poly(thiophene-3-acetic acid) (PTAA), or copolymers thereof. In some embodiments, the polymer comprises an insulating polymer (i.e., non-conductive), such as polyesters, polyethylenes (e.g., polytetrafluoroethylene (PTFE)), polyacrylates, polypropylenes, epoxy, polyamides, polyimides, polybenzoxazoles, poly(amino acids), and the like. For example, the polymer may be TEFLON, poly(glycidyl methacrylate) (PGMA), poly(maleic anhydride-alt-styrene) (p(MA-alt-St)), poly[maleic anhydride-co-dimethyl acrylamide¬ co-di(ethylene glycol) divinyl ether] (poly(MaDmDe)), poly(furfuryl methacrylate) (PFMA), poly(vinyl pyrrolidone) (PVP), poly(para-xylylene) or its derivatives, poly(dimethylaminomethyl styrene) (PDMAMS)), poly(propargyl methacrylate) (PPMA), poly(methacrylic acid-co-ethyl acrylate) (PMAA-co-EA), poly(perfluoroalkyl ethyl methacrylate), poly(perfluorodecyl acrylate) (PPFA), poly(trivinyltrimethoxycyclotrisiloxane), poly(furfuryl methacrylate), poly(cyclohexyl methacryateco-ethylene glycol dimethacrylate), poly(cyclohexyl methacrylate) (PCHMA), poly(pentafluorophenyl methacrylate) (PPFM), poly(pentafluorophenyl methacrylate co-ethylene glycol diacrylate), poly(methacrylic acid-co-ethylene glycol dimethacrylate), poly(methyl methacrylate) (PMMA), or poly(3,4¬ ethylenedioxythiophene. Those of ordinary skill in the art would be able to identify additional insulating polymers suitable for use in this process.

Devices can be fabricated using techniques well known in the art. The choice of fabrication technique will depend on the material used for the device and the size of the array. Exemplary materials for fabricating the devices include glass, silicon, steel, nickel, polymers, e.g., poly(methylmethacrylate) (PMMA), polycarbonate, polystyrene, polyethylene, polyolefins, silicones (e.g., poly(dimethylsiloxane, PDMS)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) is used to fabricate silicon-based devices with small gaps, small obstacles, and large aspect ratios (ratio of obstacle height to lateral dimension). Thermoforming (embossing, injection molding) of plastic devices can also be used, e.g., when the smallest lateral feature is about 20 microns and the aspect ratio of these features is about 10 microns. Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser micromachining can be adopted for plastic materials with high photon absorption efficiency. This technique is suitable for lower throughput fabrication because of the serial nature of the process.

For mass-produced plastic devices, thermoplastic injection molding, and compression molding can be suitable. Conventional thermoplastic injection molding used for mass-fabrication of compact discs (which preserves fidelity of features in sub-microns) can also be employed to fabricate the devices. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding can be chosen as the method of manufacture. Compression molding (also called hot embossing or relief imprinting) has the advantages of being compatible with high molecular weight polymers, which are excellent for small obstacles and can replicate high aspect ratio obstacles but has longer cycle times. Injection molding works well for low aspect ratio obstacles and is most suitable for low molecular weight polymers.

A device can be fabricated in one or more pieces that are then assembled. Layers of a device can be bonded together by clamps, adhesives, heat, anodic bonding, or reactions between surface groups (e.g., wafer bonding). Alternatively, a device with channels in more than one plane can be fabricated as a single piece, e.g., using stereolithography or other three-dimensional fabrication techniques.

To reduce non-specific adsorption of cells or compounds released by lysed cells onto the channel walls, one or more channel walls can be chemically modified to be non-adherent or repulsive. The walls can be coated with a thin film coating (e.g., a monolayer) of commercial non-stick reagents, such as those used to form hydrogels. Additional examples of chemical species that can be used to modify the channel walls include oligoethylene glycols, fluorinated polymers, organosilanes, thiols, poly-ethylene glycol, hyaluronic acid, bovine serum albumin, poly-vinyl alcohol, mucin, poly-HEMA, methacrylated PEG, and agarose. Charged polymers can also be employed to repel oppositely charged species. The type of chemical species used for repulsion and the method of attachment to the channel walls will depend on the nature of the species being repelled and the nature of the walls and the species being attached. Such surface modification techniques are well known in the art. The walls can be functionalized before or after the device is assembled. The channel walls can also be coated to capture materials in the sample, e.g., membrane fragments or proteins.

To couple a binding moiety to the surfaces of the substrate, the substrate can be, for example, exposed to an oxygen plasma prior to surface modification to create a silicon dioxide layer, to which binding moieties can be attached. The substrate can then be rinsed, e.g., twice in distilled, deionized water and allowed to air dry. Silane immobilization onto exposed glass is performed by immersing samples for 30 seconds in freshly prepared, 2% v/v solution of 3-[(2-aminoethyl)amino]propyltrimethoxysilane in water followed by further washing in distilled, deionized water. The substrate is then dried in nitrogen gas and baked. Next, the substrate is immersed in 2.5% v/v solution of glutaraldehyde in phosphate buffered saline for 1 hour at ambient temperature. The substrate is then rinsed again, and immersed in a solution of 0.5 mg/mL binding moiety, e.g., anti-CD71, anti-CD36, anti-GPA, or anti-CD45, in distilled, deionized water for 15 minutes at ambient temperature to couple the binding agent to the obstacles. The substrate is then rinsed twice in distilled, deionized water, and soaked overnight in 70% ethanol for sterilization.

To couple a binding moiety to the surfaces of the nanostructures, the nanostructures can be noncovalently functionalized with 1,1-carbonyldiimidazole (CDI)-activated Tween. Tween-20 is reacted with CDI under DMSO for 2 hours at 40° C. then dried using a Rotovap. Devices were treated with 1% CDI-activated Tween for 30 minutes then flushed with DI water. Various binding moieties, e.g. biotin, avidin, antibodies, can then be attached to the CDI-activated Tween depending on the applications. This is performed by injecting the binding moiety in solution and incubating for 30-60 minutes at room temperature, followed by rinsing with phosphate buffered saline (PBS).

There are multiple techniques other than the methods described above by which binding moieties can be immobilized onto (and into) the obstacles and the surfaces of the device. Simple physio-absorption onto the surface can be the choice for simplicity and cost. Another approach can use self-assembled monolayers (e.g., thiols on gold) that are functionalized with various binding moieties. Additional methods can be used depending on the binding moieties being bound and the material used to fabricate the device. Surface modification methods are known in the art. In addition, certain cells can preferentially bind to the unaltered surface of a material. For example, some cells can bind preferentially to positively charged, negatively charged, or hydrophobic surfaces or to chemical groups present in certain polymers.

The cell binding device can be made out of different materials. Depending on the choice of the material different fabrication techniques can also be used. The device can be made out of plastic, such as polystyrene, using a hot embossing technique. The obstacles and the necessary other obstacles are embossed into the plastic to create the bottom surface. A top layer can then be bonded to the bottom layer. Injection molding is another approach that can be used to create such a device. Soft lithography can also be utilized to create either a whole chamber made out of poly(dimethylsiloxane) (PDMS), or only the obstacles can be created in PDMS and then bonded to a glass substrate to create the closed chamber. Yet another approach involves the use of epoxy casting techniques to create the obstacles through the use of UV or temperature curable epoxy on a master that has the negative replica of the intended obstacle. Laser or other types of micromachining approaches can also be utilized to create the flow chamber. Other suitable polymers that can be used in the fabrication of the device are polycarbonate, polyethylene, and poly(methyl methacrylate). In addition, metals like steel and nickel can also be used to fabricate the device as described herein, e.g., by traditional metal machining. Three-dimensional fabrication techniques (e.g., stereolithography) can be employed to fabricate a device in one piece. Other methods for fabrication are known in the art.

Additional Components

Systems that include the new devices described herein can also include additional components or modules, e.g., for isolation, enrichment, collection, manipulation, or detection, e.g., of CTCs. Such components are known in the art. For example, devices can include one or more inlets for sample or buffer input, and one or more outlets for sample output. Arrays can also be employed on a device having components for other types of enrichment or other manipulation, including affinity, magnetic, electrophoretic, centrifugal, and dielectrophoretic enrichment. Devices can also be employed with a component for two-dimensional imaging of the output from the device, e.g., an array of wells or a planar surface.

In one example, a detection module can be in fluid communication with a separation or enrichment device. The detection module can operate using any method of detection disclosed herein, or other methods known in the art. For example, the detection module includes a microscope, a cell counter, a magnet, a biocavity laser (see, e.g., Gourley et al., J. Phys. D: Appl. Phys., 36: R228-R239 (2003)), a mass spectrometer, a PCR device, an RT-PCR device, a microarray, or a hyperspectral imaging system (see, e.g., Vo-Dinh et al., IEEE Eng. Med. Biol. Mag., 23:40-49 (2004)). In some embodiments, a computer terminal can be connected to the detection module. For instance, the detection module can detect a label that selectively binds to cells of interest.

Additionally, a cell counting module, e.g., a Coulter counter, can be fluidically coupled to a separation or enrichment device. Other modules, e.g., a programmable heating unit, can alternatively be fluidically coupled.

The methods can be employed in connection with any enrichment or analytical device, either on the same device or in different devices. Examples include affinity columns, particle sorters, e.g., fluorescent activated cell sorters, capillary electrophoresis, microscopes, spectrophotometers, sample storage devices, and sample preparation devices. Microfluidic devices are of particular interest in connection with the systems described herein.

Exemplary analytical devices include devices useful for size, shape, or deformability based enrichment of particles, including filters, sieves, and enrichment or separation devices, e.g., those described in International Publication Nos. 2004/029221 and 2004/113877, Huang et al. Science 304:987-990 (2004), U.S. Publication No. 2004/0144651, U.S. Pat. Nos. 5,837,115 and 6,692,952, and U.S. Application Nos. 60/703,833, 60/704,067, and 11/227,904; devices useful for affinity capture, e.g., those described in International Publication No. 2004/029221 and U.S. application Ser. No. 11/071,679; devices useful for preferential lysis of cells in a sample, e.g., those described in International Publication No. 2004/029221, U.S. Pat. No. 5,641,628, and U.S. Application No. 60/668,415; devices useful for arraying cells, e.g., those described in International Publication No. 2004/029221, U.S. Pat. No. 6,692,952, and U.S. application Ser. Nos. 10/778,831 and 11/146,581; and devices useful for fluid delivery, e.g., those described in U.S. application Ser. Nos. 11/071,270 and 11/227,469. Two or more devices can be combined in series, e.g., as described in International Publication No. 2004/029221.

Devices can also employ sample mobilization devices such as, for example, a mechanical rocker or a sonicator. Alternatively, the device can be adapted to provide centrifugal force to the receptacle and lid. A centrifugal sample mobilizer can be used to mobilize sample components, e.g., cells, within a fluid sample, e.g., a fluid sample having a free surface. A centrifugal sample mobilizer can also be used to drive cell rolling along the lid surface. In one example, a centrifugal sample mobilizer can include an axle that rotates the receptacle; in some embodiments, the centrifugal force generated by operating the device is capable of driving the lid into a non-orthogonal angle with respect to the axle.

Devices can also employ fluidic resistors to define and stabilize flows within an array and to also define the flows collected from the array. For example, in one device, a sample, e.g., blood containing CTCs, inlet channel, a buffer inlet channel, a waste outlet channel, and a product outlet channel are each connected to an array. The inlets and outlets act as flow resistors.

Combinations of Devices

Figure 24:
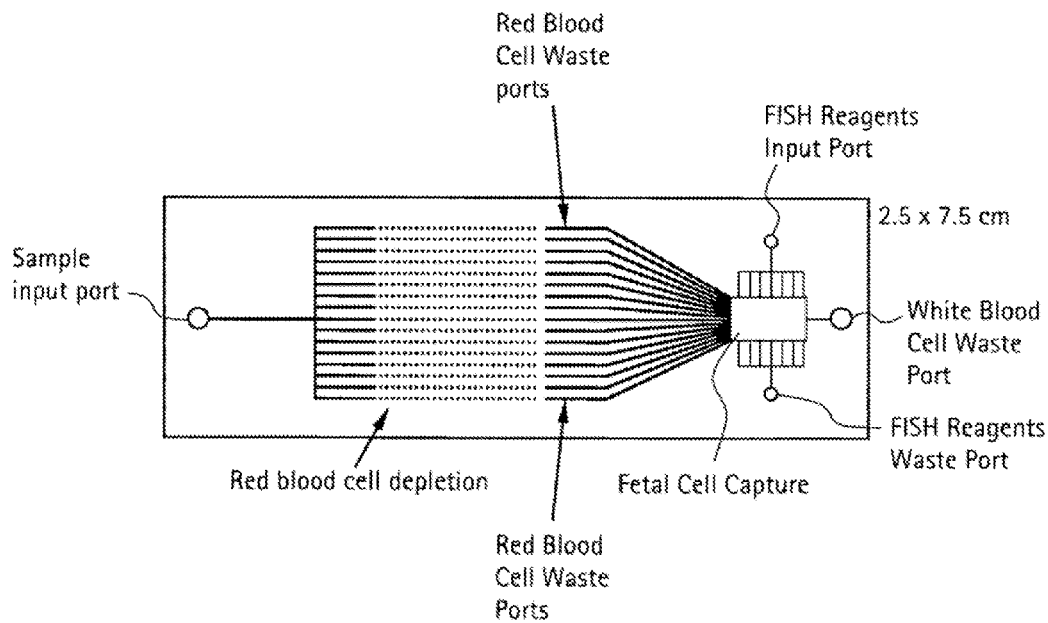
FIG. 24 is a schematic representation of an exemplary device for isolating and analyzing fetal red blood cells.

The devices as described herein can be used alone or in any combination. In addition, the steps of the methods described herein can be employed in any order, unless otherwise specified. A schematic representation of a combination device for detecting and isolating fetal red blood cells is shown in FIG. 24. In one example, a sample can be processed using a cell lysis step, and then desired cells can be trapped in a cell binding device. If the cells trapped are sufficiently pure, no further processing step is needed. Alternatively, only one of the lysis or binding steps can be employed prior to arraying. In another example, a mixture of cells can be subjected to lysis, size based separation, binding using an array of permeable obstacles, and arraying. The methods as described herein can be carried out on one integrated device containing regions for cell lysis, cell binding, arraying, and size based separation. Alternatively, the devices can be separate, and the populations of cells obtained from each step can be collected and manually transferred to devices for subsequent processing steps.

Positive or negative pressure pumping can be used to transport cells through the microfluidic devices as described herein.

Fluidic Channels with Selectively Permeable Walls

Figure 44A:
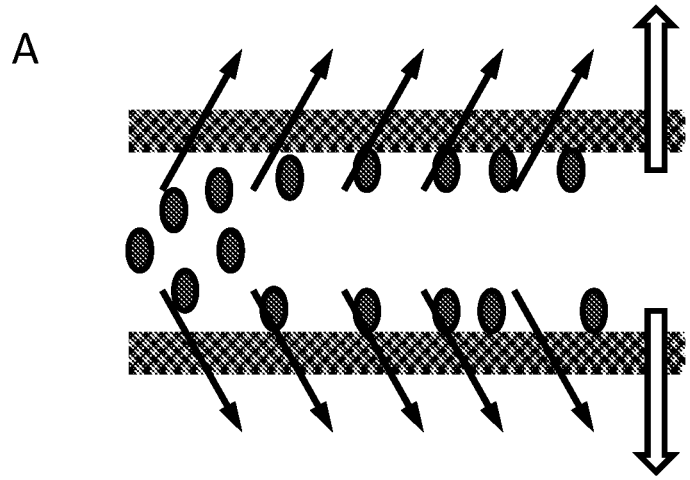
FIGS. 44A and 44B are schematics of devices in which channel walls are fabricated from the aligned nanostructures, allowing the entire channel to be selectively permeable. Fluid may be retained outside the selectively permeable channel by another non-permeable channel or chamber.

One or more of the fluidic channel walls can be fabricated entirely or in part from the aligned nanostructures, allowing the entire channel (or part thereof) to be selectively permeable. Fluid can be retained outside the selectively permeable channel by another channel, e.g., a non-permeable, channel or chamber. This allows for the creation of different conditions inside and outside of the channel. One embodiment shown in FIG. 44A has a higher pressure inside the channel than outside. This will cause some fluid and particles smaller than the void spaces between the nanostructures to be forced out of the channel, resulting in a higher concentration of larger particles (larger than the void spaces between nanostructures) inside the channel.

Figure 44B:
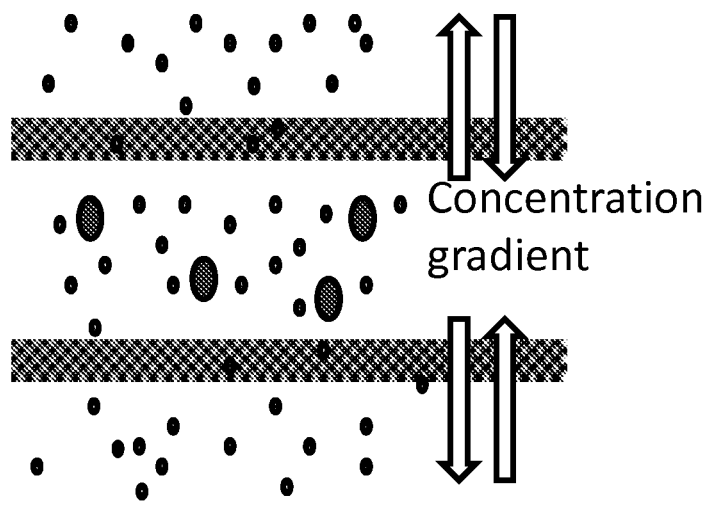

The larger particles will also be forced towards the channel walls by the fluid pressure so that interaction between the walls and the particles are enhanced. The walls may be functionalized with a binding moiety so that specific particles may be captured. Alternatively there could be higher pressure outside the channel than inside, allowing fluid, ions, biomolecules and nanoparticles, particles from the outside to enter the channel and mix with the sample inside. Another embodiment is shown in FIG. 44B, where there are concentration gradients across the selectively permeable channel wall so that molecules from outside the channel can diffuse inside and vice versa. This can be used to alter the sample composition inside the channel by adding or depleting specific molecules. Examples of molecules include ions, nutrients, cell signaling molecules, dye molecules, proteins, and enzymes.

Methods of Use of Microfluidic Devices

The methods described herein can involve contacting a sample including a mixture of particles, e.g., cells, with the surfaces of a microfluidic device. A population of cells in a complex mixture of cells such as blood then binds to the surfaces of the device, e.g., to surfaces of the selectively permeable obstacles, and sufficiently small particles can bind to surfaces of the internal nanotubes that can also be functionalized. Desirably, at least 60%, 70%, 80%, 90%, 95%, 98%, or 99% of cells that are capable of binding to the surfaces of the device are removed from the mixture. The surface coating is desirably designed to minimize nonspecific binding of cells. For example, at least 99%, 98%, 95%, 90%, 80%, or 70% of cells not capable of binding to the binding moiety are not bound to the surfaces of the device. The selective binding in the device results in the separation of a specific living cell population from a mixture of cells.

Obstacles are present in the device to increase surface area for cells to interact with while in the chamber containing the obstacles so that the likelihood of binding is increased. The flow conditions are such that the cells are very gently handled in the device without the need to deform mechanically in order to go in between the obstacles. Positive pressure or negative pressure pumping or flow from a column of fluid can be employed to transport cells into and out of the microfluidic devices as described herein. In an alternative embodiment, cells are separated from non-cellular matter, such as non-biological matter (e.g., beads), non-viable cellular debris (e.g., membrane fragments), or molecules (e.g., proteins, nucleic acids, or cell lysates).

Figure 25:
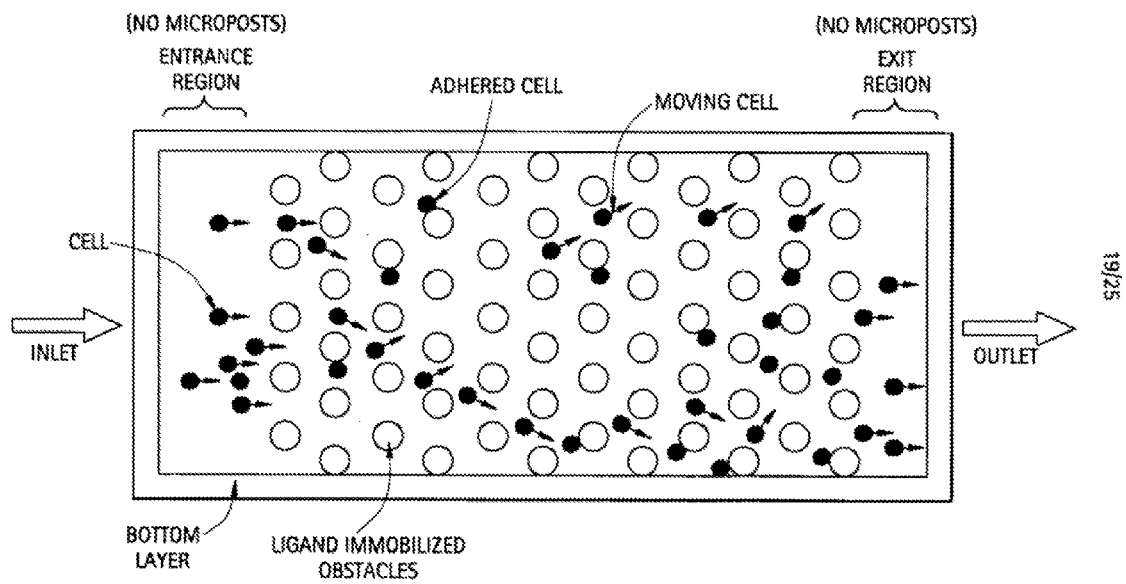
FIG. 25 is an illustration of a mixture of cells flowing through a cell binding device.

FIG. 25 shows cells expressing a specific surface antigen binding to a binding moiety coated onto obstacles, while other cells flow through the device (small arrow on cells depict the directionality of cells that are not bound to the surface). The top and bottom surfaces of the flow apparatus can also be coated with the same binding moiety, or a different binding moiety, to promote cell binding.

Exemplary cell types that can be separated using the methods and devices described herein include adult red blood cells, fetal red blood cells, trophoblasts, fetal fibroblasts, white blood cells (such as T cells, B cells, and helper T cells), infected white blood cells, stem cells (e.g., CD34 positive hematopoeitic stem cells), epithelial cells, tumor cells, and infectious organisms (e.g., bacteria, protozoa, and fungi).

Figure 26A:
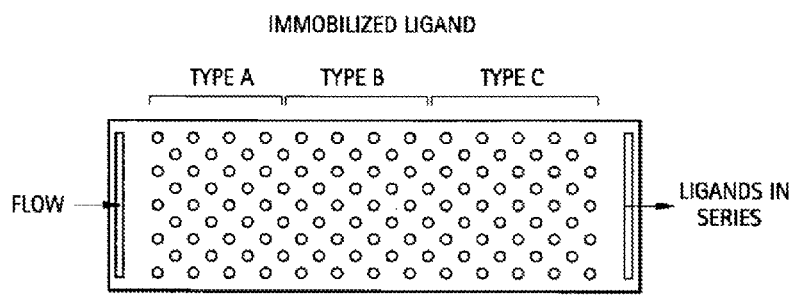
FIG. 26A is an illustration of a cell binding device for trapping different types of cells in series.
Figure 26B:
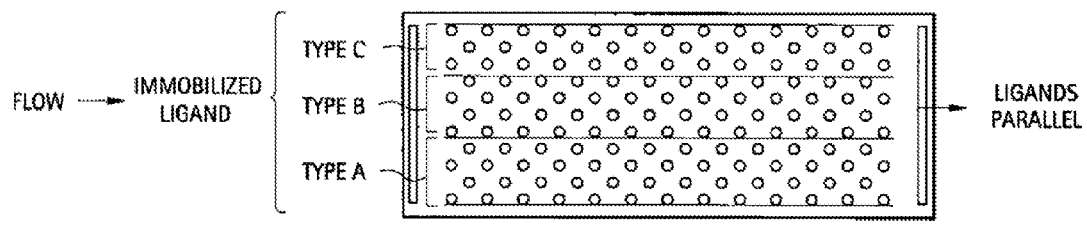
FIG. 26B is an illustration of a cell binding device for trapping different types of cells in parallel.

Samples can be fractionated into multiple homogeneous components using the methods and devices described herein. Multiple similar devices containing different binding moieties specific for a population of cells can be connected in series or in parallel. Serial separation can be employed when one seeks to isolate rare cells. On the other hand, parallel separation can be employed when one desires to obtain differential distribution of various populations in blood. FIGS. 26A-26B show parallel and serial systems for the separation of multiple populations of cells from blood. For parallel devices, two or more sets of obstacles that bind different types of cells can be located in distinct regions or they can be interspersed among each other, e.g., in a checkerboard pattern or in alternating rows. In addition, a set of obstacles can be attached to the top of the device and another set can be attached to the bottom of the device. Each set can then be derivatized to bind different populations of cells. Once a sample has passed through the device, the top and bottom can be separated to provide isolated samples of two different types of cells.

Figure 27:
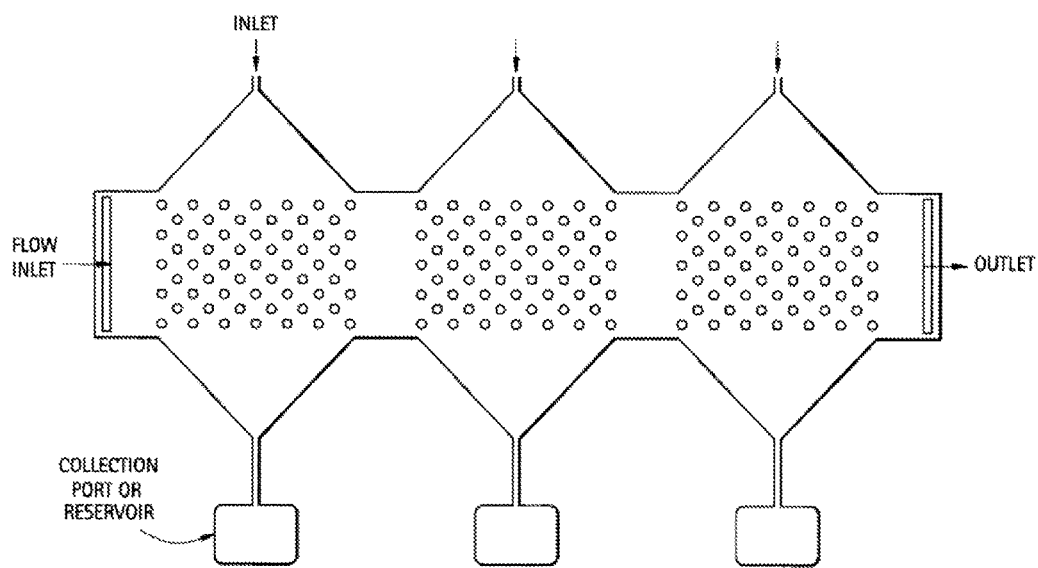
FIG. 27 is an illustration of a cell binding device that enables recovery of bound cells.

The cell binding devices can be used to deplete the outlet flow of a certain population of cells, or to capture a specific population of cells expressing a certain surface molecule for further analysis. The cells bound to obstacles can be removed from the chamber for further analysis of the homogeneous population of cells (FIG. 27). This removal can be achieved by incorporating one or more additional inlets and exits orthogonal to the flow direction. Cells can be removed from the chamber by purging the chamber at an increased flow rate that is sufficient to overcome the binding force between the cells and the obstacles. Other approaches can involve coupling binding moieties with reversible binding properties, e.g., that are actuated by pH, temperature, or electrical field. The binding moiety, or the molecule bound on the surface of the cells, can also be cleaved by enzymatic or other chemical means.

In fetal red blood cell isolation, a sample having passed through a lysis device can be passed through a cell binding device whose surfaces are coated with CD45. The permeable obstacles can provide increased capture efficiency relative to solid obstacles by decreasing the fluid boundary layer around the obstacles. White blood cells expressing CD45 present in the mixture bind to the walls of the device, and the cells that pass through the device are enriched in fetal red blood cells. Alternatively, the obstacles and device surfaces are coated with anti-CD71 in order to bind fetal nucleated red blood cells (which express the CD71 cell surface protein) from a whole maternal blood sample. One percent of adult white blood cells also express CD71. A sample of maternal blood is passed through the device and both populations of cells that express CD71 bind to the device. This results in the depletion of fetal red blood cells from the blood sample. The fetal cells are then collected and analyzed. For example, cells are collected on a planar substrate for fluorescence in situ hybridization (FISH), followed by fixing of the cells and imaging.

The ultra-high void volume of the nanotube obstacles modifies fluid flow and enhances particle-obstacle interactions across particle sizes ranging from nanometers to tens of microns or more. This technology provides an extremely high degree of control of bioseparation processes to access bioparticles of interest, opening new pathways for both research and point-of-care diagnostics. In particular, the devices and methods described herein can be used for the capture particles such as cells in fluids. In cancer monitoring applications, for example, the devices can be configured to capture circulating tumor cells as well as exosomes and DNA. In viral monitoring, for example, the devices can be configured to capture T cells and viruses. The devices can be also be used to effect various manipulations on particles in a sample. Such manipulations include enrichment or concentration of a particle, including size based fractionation, or alteration of the particle itself or the fluid carrying the particle.

After being enriched by one or more of the devices as described herein, cells can be collected and analyzed by various methods, e.g., nucleic acid analysis. The sample can also be further processed prior to analysis. In one example, cells can be collected on a planar substrate for fluorescence in situ hybridization (FISH), followed by fixing of the cells and imaging. Such analysis can be used to detect fetal abnormalities such as Down syndrome, Edwards' syndrome, Patau's syndrome, Klinefelter syndrome, Turner syndrome, sickle cell anemia, Duchenne muscular dystrophy, and cystic fibrosis. The analysis can also be performed to determine a particular trait of a fetus, e.g., sex.

EXAMPLES

Example 1

Selectively Permeable Obstacle of Carbon Nanotube Obstacles

To test the permeable obstacles under fluid flow, microfabricated PDMS channels were sealed to the silicon surface around the carbon nanotubes using oxygen plasma bonding. The microfluidic channels were generated using standard soft lithography (3). SU-8 photoresist (Microchem) was patterned on a silicon wafer by photolithography to form a negative mold. A 10:1 mixture of polydimethylsiloxane (PDMS) prepolymer and curing agent (Sylgard 184, Dow Corning) was poured onto the mold and baked at 75° C. until cured. The PDMS channels were then bonded to the silicon wafers containing the carbon nanotube obstacles after oxygen plasma treatment. The surfaces of carbon nanotubes, which are hydrophobic, can be made hydrophilic by the addition of Tween-20, to facilitate infiltration of fluid inside the nanostructure obstacles. Fluid was injected by pressure-driven flow using a syringe pump.

For the 'solid' devices used as controls, PDMS channels with cylindrical posts were fabricated using soft lithography and bonded to 1"×3" glass microscope slides after oxygen plasma treatment.

The devices were used in a fluorescent dye and quantum dot infiltration experiments described in further detail below. The specific devices had single posts 200 lam in diameter and 100 μm in height, sealed inside a 3 mm×20 mm×100 μm PDMS channel. 0.5% Tween-20 in DI water was used to treat the devices after fabrication to make surfaces hydrophilic, and to block non-specific binding. Rhodamine B (Sigma Aldrich) was injected into the channel using a syringe pump (Harvard Apparatus) set to 5 uL/min flow rate. Imaging was performed using a confocal microscope (Zeiss), and intensity plots are made using ImageJ software.

FIG. 28A and FIG. 28B present confocal micrographs of 200 μm diameter permeable and solid posts as a fluorescent dye solution flowed through the micro-channel. Water and the small molecule dyes (rhodamine, MW 479 Da) penetrated inside the permeable carbon nanotube post over 90 seconds (see FIG. 29A); by comparison, and as expected, there was no dye penetration inside the solid PDMS post (see FIG. 29B).

FIGS. 29A and 29B show the fluorescence intensity analysis of each type of post as the dye penetrated over time.

To characterize flow of nanoparticles inside the permeable obstacles, a dilute suspension of fluorescent quantum dots (QDs) 10-20 nm in size was injected into a microfluidic channel to observe the flow paths of the QDs inside and outside of a 200 μm diameter permeable post in the channel.

FIG. 30 follows the path of a single QD as it travels through a permeable post (shown with yellow arrows) and compares it with another QD (indicated by dashed red arrows) that passes around the outside of the same post. Due to increased fluid resistance inside the permeable obstacle, the QD travels inside the carbon nanotube post at a significantly reduced velocity, only 8% of the velocity of its counterpart traveling outside the post. These experiments demonstrate the ability of aligned carbon nanotube obstacles to allow pressure-driven flow of both molecular and particulate species inside the permeable material.

Example 2

Mechanical Filtration

A straight-forward yet powerful application that takes advantage of the high void level and ease of patterning of the permeable carbon nanotube obstacles is mechanical filtration.

FIG. 31A-FIG. 31D show a micro-patterned Y-shaped barrier for continuous separation and concentration formed using the techniques described above to apply permeable carbon nanotube obstacles for mechanical separation. In this configuration, large particles, which cannot pass through the permeable obstacles (Y-shaped barrier here), are guided by the barrier into the narrow neck of the barrier, whereas fluid and smaller particles efficiently pass through the barrier, ultimately resulting in a concentration of the larger particles in the sample.

Figure 31A:
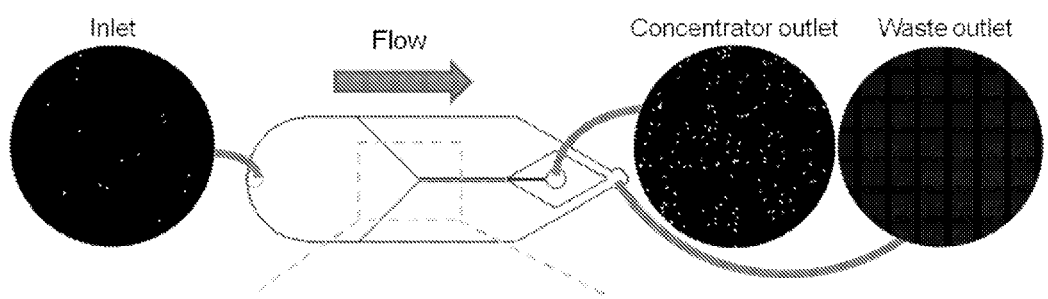
FIGS. 31A-D show the operations of a nanopermeable Y-barrier.
Figure 31B:
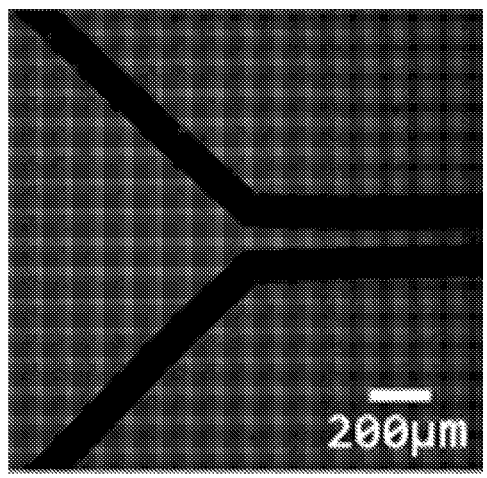
Figure 31C:
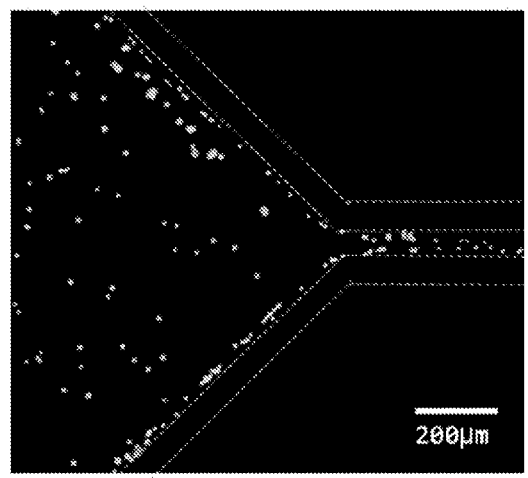
Figure 31D:
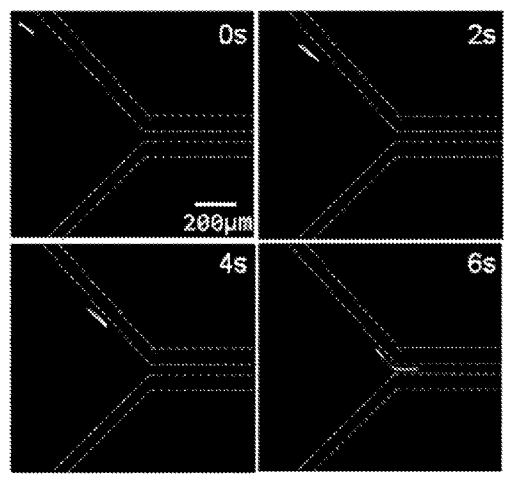

FIG. 31A is a schematic of a device with overall dimensions 3 mm(W)×20 mm(L)×100 μm(H). FIG. 31B is a fluorescent micrograph showing red fluorescent BSA molecules have passed through the permeable barriers. FIG. 31C shows that 10 μm polymer beads cannot pass through the selectively permeable barrier sides, and are directed to the central channel. FIG. 31D presents streak images of a single 10 μm bead as it enters the constricted section of the barrier. The Y-barrier devices were blocked against non-specific binding with 0.5% Tween-20 in DI water. 10 μm green fluorescent polymer beads (Duke Scientific) were injected at 10 μL/min using a syringe pump. Flow from both outlets were collected with tubing and imaged under a fluorescent microscope. Streak images in FIG. 29D were taken under 500 ms exposure.

In FIG. 31A, the inside width of the central channel in the Y-shaped barrier was 100 μm. Blue lines show PDMS channel boundaries and black lines show the obstacle. The circular insets show micrographs of the inlet, concentrator outlet, and waste outlet, showing selective concentration of 10 μm fluorescent beads. The 10 μm fluorescent beads cannot pass through the Y-shape selectively permeable barrier (~80 nm spacing) and are thus guided by the barrier into the narrow neck of the barrier (see FIGS. 7C and 7D), and the 'concentrator outlet'. In contrast, fluid and particles smaller than 80 nm efficiently pass through the barrier (see FIG. 31B) and escape through the 'waste outlet', ultimately resulting in concentration of the larger particles. The flow through the 'waste outlet' was measured to be 10 times that of the flow through the 'concentrator outlet', thereby resulting in an 11-fold concentration of the sample. Higher concentration factors could be achieved by adjusting the ratio of the width of the passage formed by the selectively permeable barriers to the width of the overall PDMS channel, or by cascading several barriers.

Example 3

Selectively Permeable Obstacles Alter Particle Flow Paths

Fluid flow through a permeable obstacle can alter the flow characteristics of the fluid in the vicinity of the obstacle and change the boundary layer and overall fluid flow behavior, relative to the boundary layer and flow behavior that would be observed were the obstacle replaced with an obstacle of the same defined space and made of a material through which fluid does not flow. As noted above, obstacles can be configured to alter the streamlines such that a smaller or a larger number of the particles contacts the obstacles, relative to the number that would contact an obstacle of the same defined space and made of a material through which fluid does not flow (e.g., a solid, non-porous article).

This phenomenon was investigated by flowing suspensions of 10 μm diameter beads through a microchannel containing a 500 μm diameter selectively permeable post and through a microchannel containing a 500 μm diameter permeable post, and comparing the beads' flow trajectories around the two posts. Due to boundary layer modulation by the permeable posts, the 10 μm beads encounter more surface interaction with the permeable posts than with solid posts of the same geometry.

Figure 32A:
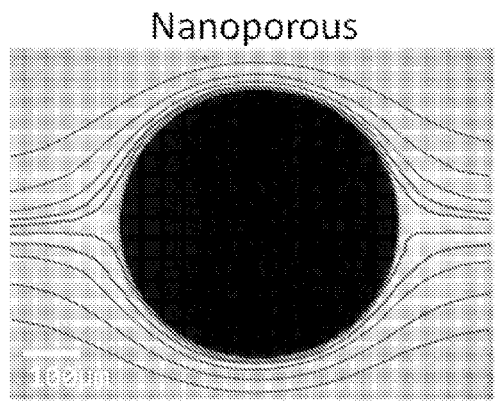
FIG. 32A and FIG. 32B are microphotographs of particle streamline tracks of beads flowing around, respectively, a nanopermeable post and a solid post. The streamline tracks are closer to the nanopermeable post than to the solid post.
Figure 32B:
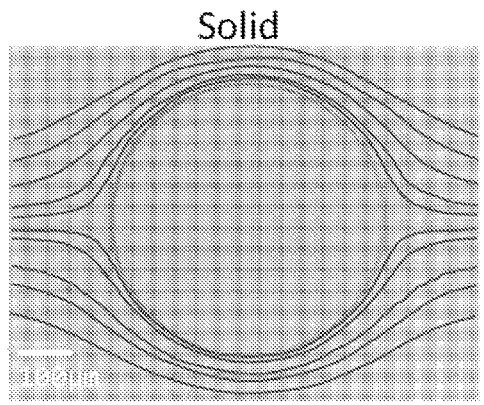
Figure 33A:
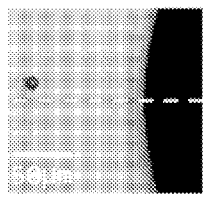
FIGS. 33A-FIG. 33F are micrographs of single particles approaching a nanopermeable post (FIG. 33A-FIG. 33C) and a solid post (FIG. 33D-FIG. 33F) from the same start position. The particles approaching the nanopermeable post eventually touch the post, and the ones approaching the solid post never do.
Figure 33D:
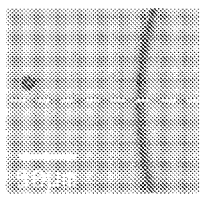
Figure 33B:
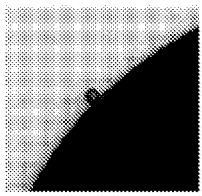
Figure 33E:
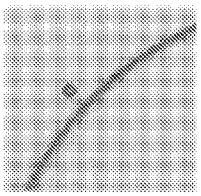
Figure 33C:
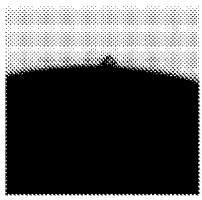
Figure 33F:
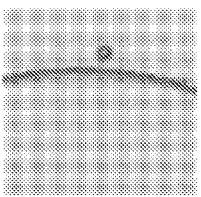

FIG. 32A and FIG. 32B show superimposed particle tracks from multiple beads flowing around the permeable post and around the 500 μm solid PDMS post. Tracks around the permeable post are concentrated in an area that is closer to the post surface than the tracks around the solid post.

FIG. 33A-FIG. 33F are snapshots of two single particles approaching a permeable post (FIG. 33A-FIG. 33C) and a solid post (FIG. 33D-FIG. 33F) from the same start position. The particle approaching the permeable post eventually touches the post, and the one approaching the solid post never does.

Figure 34A:
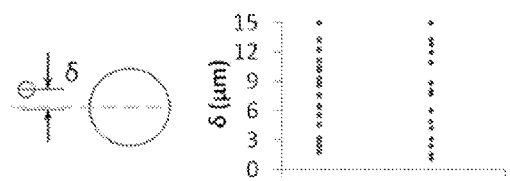
FIGS. 34A-34C are graphs of positional data of multiple beads as they approach both types of posts and a plot of device capture efficiency. The incoming bead flow paths were randomly distributed, at a distance δ from the post center line when 200 μm away from the front of the post. All beads approaching the nanopermeable post from ~17 μm or less away from the centerline eventually touch the post ($\gamma$ or d=0), but only a few beads ever touch the solid post.
Figure 34B:
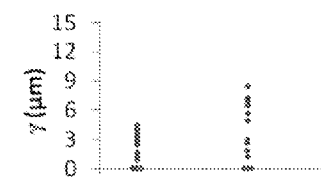
Figure 34C:
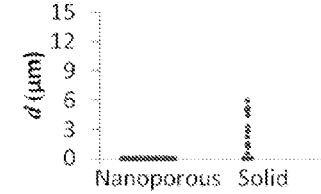

FIG. 34A-FIG. 34C compares the positional data of multiple beads as they approach the two posts. The incoming bead flow paths were randomly distributed, at a distance δ from the post center line when 200 μm away from the front of the post.

All beads approaching the permeable post from 17 μm or less away from the centerline eventually touch the post (γ or d=0), but only a few beads ever touch the solid post. FIG. 35 shows data points of individual bead positions when they are 200 μm in front of the posts and when they are at their closest to the posts. Beads approaching the permeable post pass several microns closer to the post surface than their counterparts approaching the solid post. FIG. 36 presents this in terms of the interception efficiency of the two posts relative to different starting positions of the beads. In this context, the interception efficiency is used to indicate the percentage of beads that will touch the post if multiple incoming beads are randomly distributed within a distance δ about the center line.

Analysis of the trajectories of multiple beads shows that, when solid posts are used, only particles approaching at less than 2.5 μm away from the centerline contact the solid post, whereas permeable posts can provide 100% interception of bioparticles approaching from as far as 17 μm away from the post centerline. Interaction between particles and obstacles can therefore be enhanced seven-fold for this geometry. This improvement is achieved through the ability of permeable surfaces to modulate boundary layer flow dynamics (and therefore streamlines) by allowing fluid transport across the post macro-surface. Enhanced interaction between particle and post can be advantageous for applications where it is desirable to selectively capture a given bioparticle on a surface.

Example 4

Bioparticle Capture Using Functionalized Permeable Obstacles

Two devices combining physical microscale device design with controlled mechanical and chemical properties to capture bioparticles ranging three orders of magnitude in size demonstrated the capability of selectively permeable obstacles to separate bioparticles.

Referring to FIG. 37A-FIG. 37D, a device 700 included a 500 μm diameter post 710 configured to capture CD4+ T-cells (~10 μm). The post 710 was functionalized with anti-CD4 antibodies. Fluid containing 10 μm size fluorescently labeled CD4 T-cells passed through the device at 10 μL/min. FIG. 37A and FIG. 37B, respectively, present a schematic and a SEM both showing the geometry of device 200. FIG. 37C and FIG. 37D present images showing the location of fluorescent captured cells on, respectively, devices with permeable and devices with solid posts of identical geometry. The inset control boxes show capture on non-functionalized chips.

Referring to FIG. 38A-FIG. 38D, a device 800 included an array of circular posts 810 configured to capture *Escherichia coli* bacteria (~1 μm). The posts 810 were functionalized with anti-*E. coli* antibodies (polyclonal *E. coli* antibody (Abcam)). Fluid containing heat-killed fluorescent *E. coli* particles (Invitrogen) passed through the device at 10 μL/min. FIG. 38A and FIG. 38B, respectively, present a schematic and a SEM both showing the geometry of device 300. FIG. 38C and FIG. 38D present images showing the location of fluorescent captured bacteria on, respectively, devices with permeable and devices with solid posts of identical geometry. The inset control boxes show capture on non-functionalized obstacles.

In both devices 700, 800, the permeable posts 710, 810 demonstrated capture enhanced by 6-7 fold relative to solid posts of the same geometry. Non-specific binding was low in all cases. These experiments confirm that the changes in the boundary layer described above enhance interactions between bioparticles and posts, ultimately resulting in increased particle capture efficiency.

Example 5

Comparison of Functionalization Technique Effectiveness

Two different surface functionalization methods were used for the carbon nanotube permeable obstacles and the PDMS solid obstacles. To verify that the improvement in capture found with the permeable obstacles was not a result of the difference in functionalization efficiency, the density of avidin binding sites on the permeable obstacles was qualitatively compared with the density of avidin binding sites on the permeable obstacles.

The carbon nanotube device functionalization was performed using the non-covalent functionalization method described by RJ Chen (S2) using 1,1-carbonyldiimidazole (CDI)-activated Tween. Tween-20 was reacted with CDI (Sigma Aldrich) under DMSO for 2 hours at 40° C. then dried using a Rotovap. The devices were treated with 1% CDI-activated Tween for 30 minutes then flushed with DI water. For the biotin-functionalized devices 700 (see FIG. 37C), 50 μg/ml biotin (Pierce) in PBS was then injected and incubated at room temperature for 1 hour before use. For the antibody-functionalized device 800 (see FIG. 38C), 50 μg/ml fluorescent NeutrAvidin (Thermo Scientific) in PBS was injected and incubated at room temperature for 30 minutes, followed by 30 ug/ml of biotinylated antibody in PBS for 30 minutes. The devices were then washed and blocked for non-specific binding with 1% BSA in PBS.

The PDMS solid obstacles shown in FIG. 37D were functionalized using the methods described in detail by S. K. Murthy, A. Sin, R. G. Tompkins, M. Toner, Langmuir 20, 11649 (December 2004). Freshly bonded devices were pretreated with 4% (v/v) solution of 3-mercaptopropyltrimethoxysilane in ethanol for 30 min at room temperature, followed with incubating with 0.01 μmol/mL GMBS in ethanol for 15 min at room temperature. NeutrAvidin and biotinylated antibodies are then added in the same way as for the carbon nanotube devices. It is noteworthy that the shape and geometry of the nanostructure posts is maintained through all of the wet functionalization steps described herein.

Example 6

Comparison of Functionalization Technique Effectiveness

FIG. 39A-FIG. 39D show a device 400 that combines the mechanical filtration capabilities of the carbon nanotube posts with surface chemistry to efficiently capture virus-sized particles. Using 40 nm fluorescent beads with an avidin-coated surface, we showed that virus-size particles can be captured inside a selectively permeable barrier obstacle containing biotin-functionalized aligned carbon nanotubes. The barrier mechanically excludes 1 μm size particles, which are larger than the 80 nm spacing between individual nanotubes in the network, while chemically trapping the 40 nm beads, which can flow through the permeable obstacle. Since there are ~$10^8$ individual carbon nanotubes per $mm^2$ of area within an obstacle, creating a 400× increase in surface area inside a 100 μm height channel, particles traveling through the nanoporous network will encounter a high degree of contact with the functionalized carbon nanotube sidewalls.

Figure 39A:
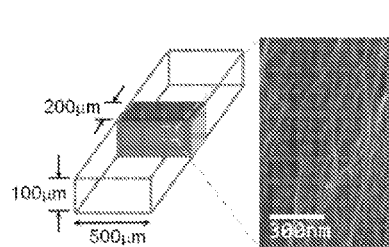
FIG. 39A and FIG. 39B, respectively, present a schematic and a scanning electron micrograph of a cell capture device with a functionalized block barrier.
Figure 39B:
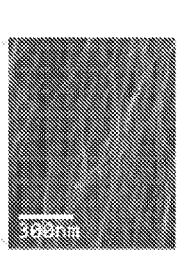
Figure 39C:
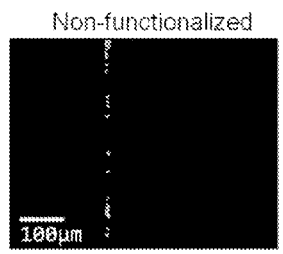
FIG. 39C shows a non-functionalized block barrier which only captures cells too large to enter the barrier. In contrast.
Figure 39D:
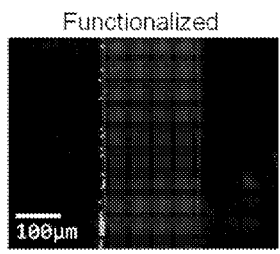
FIG. 39D shows a functionalized barrier showing 40 nm fluorescent beads with an avidin-coated surface captured inside the nanopermeable barrier containing biotin-functionalized aligned carbon nanotubes.

Fluid containing a mixture of non-functionalized 1 μm beads (green) and 40 nm avidin-coated beads (red) passed through the device 400 at 10 μL/min. FIG. 39A and FIG. 39B, respectively, present a schematic and a SEM both showing the geometry of device 400. FIG. 39C and FIG. 39D present images showing the location of fluorescent captured cells on, respectively, devices with permeable posts and devices with solid posts of identical geometry. The inset control boxes show capture on non-functionalized chips. The 1 μm beads are physically trapped in front of both barriers. The 40 nm beads are trapped inside the functionalized barrier.

Thus, the selectively permeable obstacles enhance surface interactions in two ways; the first is through fluid path modulation that impacts particles larger than the inter-carbon nanotube spacing and smaller; the second is through the high internal surface area of the carbon nanotube obstacles, that benefits particles smaller than the inter-carbon nanotube spacing (see FIG. 39A-FIG. 39D). As a consequence, a single device can be optimized to simultaneously separate particles of different size orders, with the added advantage of being able to simultaneously achieve particle concentration.

Example 7

Structural Stability

Figure 41A:
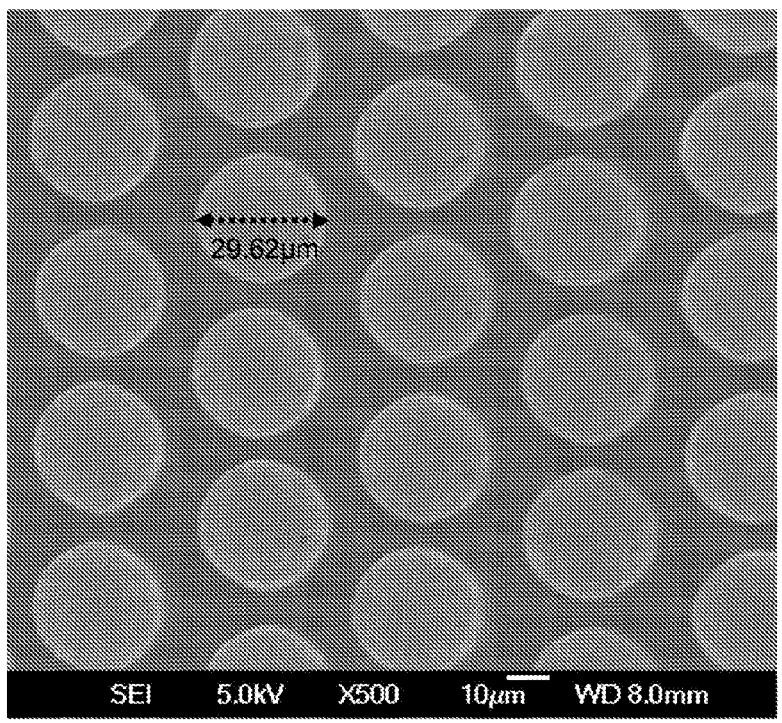
FIG. 41A and FIG. 41B, respectively, show an array of 30 μm nanoporous CNT posts before and after wet treatment.
Figure 41B:
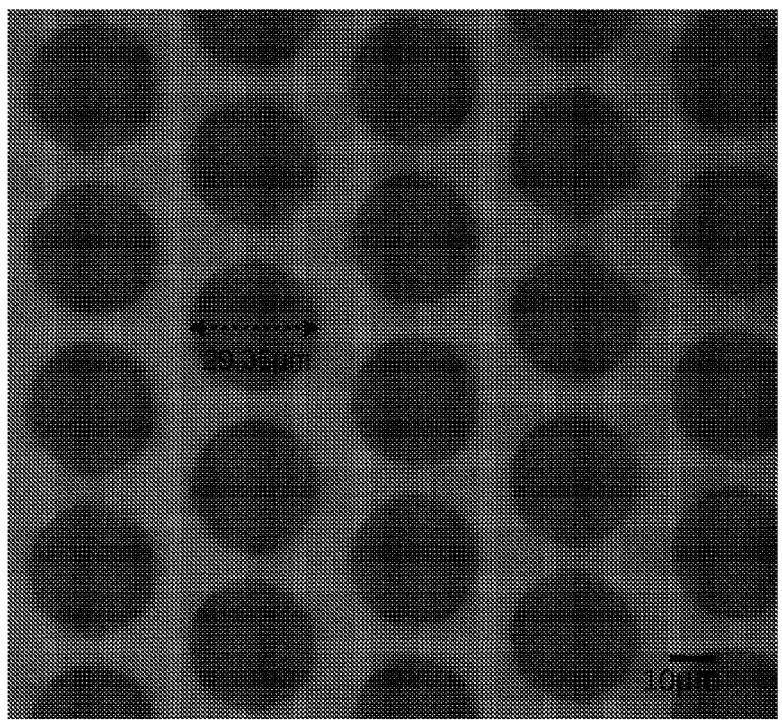

FIG. 41A shows a scanning electron micrograph of an array of posts where individual posts are made from carbon nanotubes. The image shows the shape and size of the posts immediately after growth and prior to wetting with a fluid. The post array was bonded inside a microfluidic channel after plasma treatment as shown in FIG. 25 (*e*) and (*f*). Water with 0.1% Tween-20 was introduced into the channel at a flow rate of 20 ul/min to wet the channel and the posts. FIG. 41B shows a micrograph of the channel with the post array 1 hour after wetting. Comparison between FIG. 41A and FIG. 41B demonstrates the substantial maintenance or preservation of post geometry, e.g., shape and size, after wetting with a fluid. Another example of substantial maintenance of post geometry is described below with reference to FIGS. 46A-F.

Example 8

Manipulating Porosity to Tailor Obstacle Permeability

Figure 42:
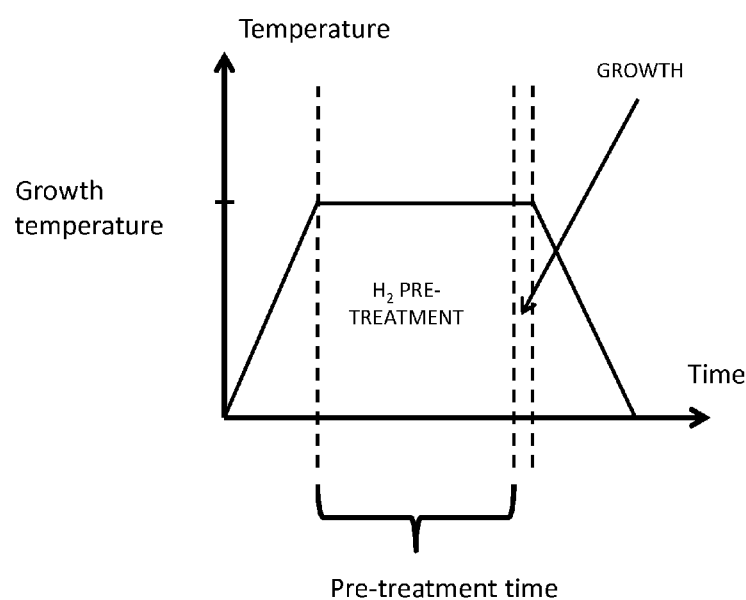
FIG. 42 is a schematic showing the relationship between process parameters that can determine aspects of CNT forest morphology.
Figure 43A:
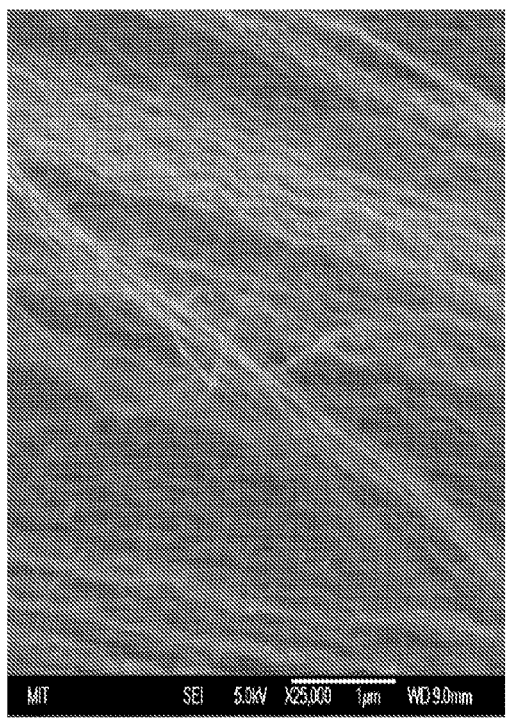
FIG. 43A and FIG. 43B, respectively, show two high-resolution images of a CNT feature/obstacle grown using the baseline process (as described in Section "Methods of Manufacture of Devices with Selectively Permeable Obstacles") and of a CNT feature for which the pre-treatment was increased by 7 minutes.
Figure 43B:
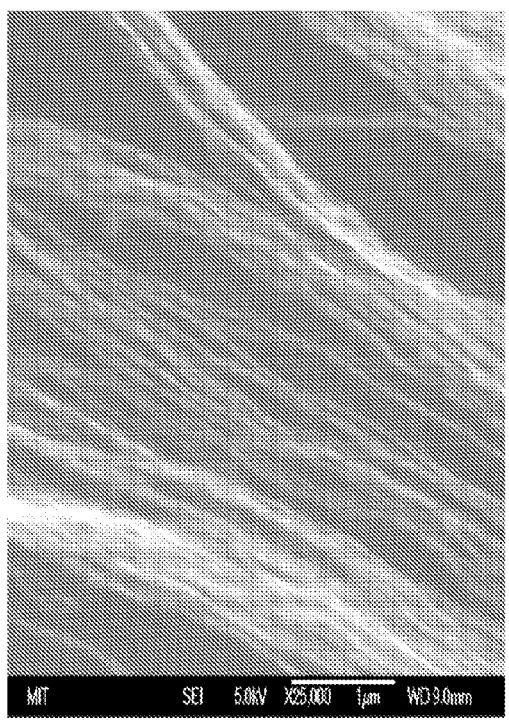

The permeability of vertically-aligned carbon nanotube features is directly dependent on their porosity, which is determined by the forests' properties such as average CNT diameter and average inter-CNT spacing. The average inter-CNT spacing also sets the maximum particle size that can penetrate the CNT features. Control of CNT forest morphology can be achieved by modifying both material specifications (e.g., thickness of the catalyst layer) and growth conditions (e.g., $H_2$ pre-treatment time, growth temperature, see FIG. 42). In FIG. 43A and FIG. 43B we show two high-resolution images of a CNT feature grown using the baseline process (as described in Section "Methods of Manufacture of Devices with Selectively Permeable Obstacles") and of a CNT feature for which the pre-treatment was increased by 7 minutes, respectively. Noticeably, the morphology of the two forests is significantly different, with the baseline feature being characterized by thinner (smaller diameter) CNTs and smaller average CNT-spacing. The forest permeability associated to the baseline and the modified, +7 minutes pre-treatment time processes was measured as follows. First, two rectangular (200 μm wide×2 mm long) features were fabricated using the baseline and the modified process, and integrated in microfluidic channels. The inlet of the devices was then connected to a constant pressure source pumping water with 0.1% TWEEN® 20 at 1 psi, with the outlet being held at atmospheric pressure. The flow rate was measured by collecting water from the outlet for 2 minutes and then measuring its volume using a pipette. Finally, the pressure and the flow rate were used to calculate permeability using Darcy's equation. The results show one order of magnitude increase in permeability when moving from the baseline (measured permeability: $\kappa=3*10^{-14}$ $m^2$) to the modified, +7 minutes pre-treatment time process (measured permeability: $\kappa=2.5*10^{-13}$ $m^2$).

Example 9

Effect of Feature Design on "Effective" Obstacle Permeability

In Example 8, we show that the permeability of carbon nanotube features depends on forest properties such as inter-CNT spacing and tube diameter, and that it can be controlled both by modifying material specifications and growth parameters. The microfluidic performance of CNT obstacles is also dependent on feature design, i.e., on the geometric shape of the CNT obstacles themselves, as this affects both the structural properties (e.g., bending stiffness) and the "effective" permeability of obstacles. Despite having the same material composition, a "full cylinder" CNT obstacle (see FIG. 5A) shows lower effective permeability (i.e., higher resistance to flow) than a "hollow cylinder" CNT obstacle (see FIG. 5B). As such, hollow designs may be advantageous for bioparticle-CNT feature interactions, and therefore provide higher capture efficiency. A comparison between a "full" and a "hollow" cylindrical CNT feature is presented in schematic FIGS. 5A and 5B, which show the larger number of streamlines terminating on and penetrating the hollow post in FIG. 5B.

Example 10

Structural Stability

To demonstrate the ability to preserve or maintain the structural stability of the ultra-porous carbon nanotube elements formed by the techniques described above, the effect of each fabrication step on an array of obstacles, each formed of a cylindrical (500 μm in diameter, 100 μm tall) carbon nanotube was analyzed. For these experiments, fluorescent (red) antibodies, and fluorescent (green) 20 μm beads were used to enhance image contrast and to visualize the particle flow around the obstacle. Beads and antibodies were suspended in PBS and injected at 20 μl/min using a syringe pump.

Figure 46A:
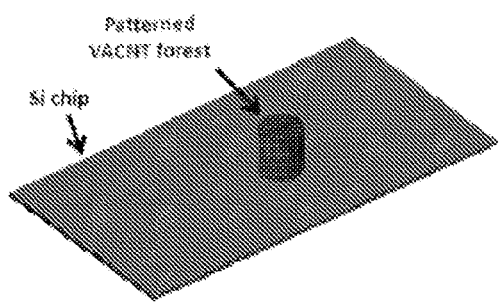
FIGS. 46A, 46B, and 46C are, respectively, schematic diagrams showing an obstacle including multiple nanostructures formed on a substrate, functionalized, and through which fluid sample that includes suspended particles are flowed.
Figure 46D:
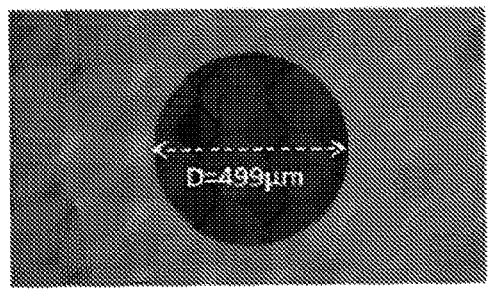
FIG. 46D, 46E, and 46F are images showing a structural property of the obstacle shown in FIG. 46A, FIG. 46B, and FIG. 46C, respectively.
Figure 46B:
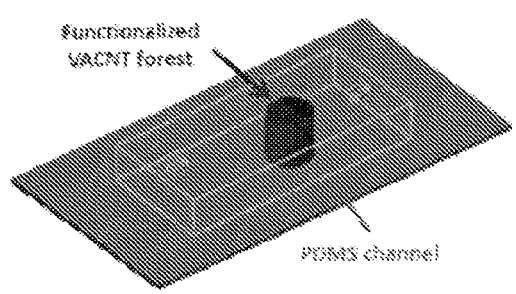
Figure 46E:
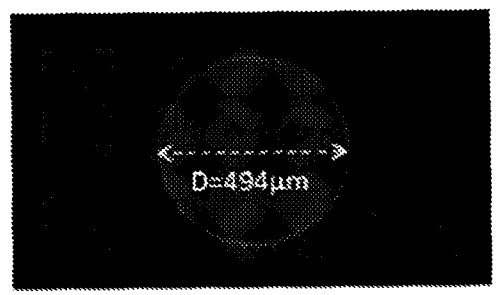
Figure 46C:
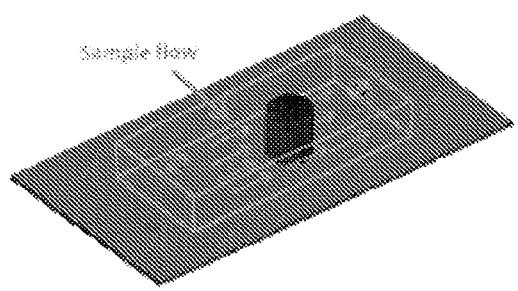
Figure 46F:
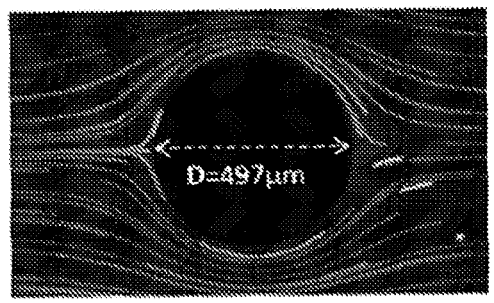

FIG. 46A shows a schematic of an obstacle including multiple carbon nanotube structures patterned on a substrate. FIG. 46D shows that a diameter of the obstacle is approximately 499 μm. FIG. 46B shows a schematic of the obstacle being integrated with the substrate and functionalized using techniques described above. FIG. 46E shows that a diameter of the functionalized substrate is approximately 494 μm. FIG. 46C shows a schematic of fluid sample being flowed past the functionalized obstacle. FIG. 46F shows that a diameter of the functionalized substrate past which the fluid sample flows is approximately 497 μm. The obstacle's geometry is preserved up to 99% of the original shape including during flow-through conditions.

Example 11

Multi-Particle Capture

Figure 47:
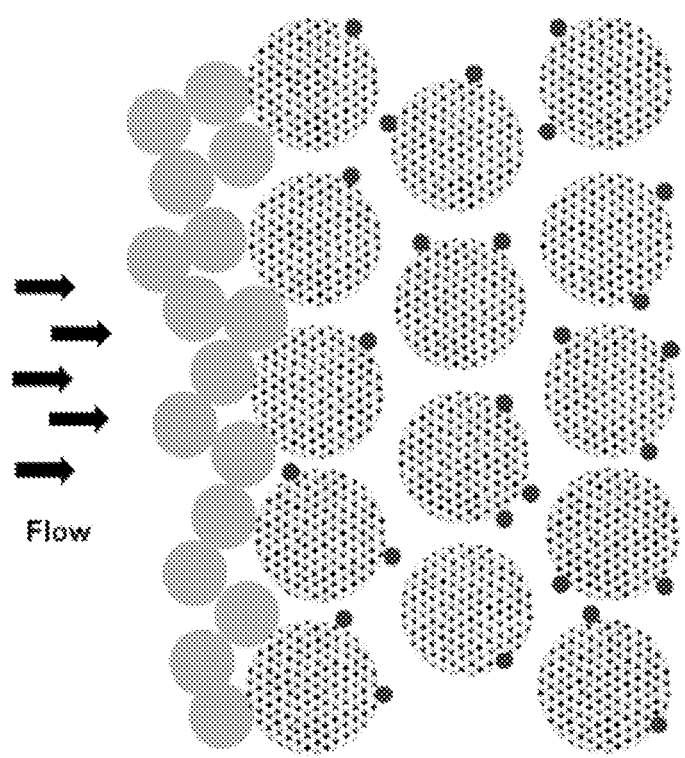
FIG. 47 is a schematic of an array of obstacles including functionalized carbon nanotube structures that can simultaneously isolate particles ranging three orders of magnitude in size. The particles are isolated through a combination of mechanical filtration and chemical affinity-based bio-recognition.

FIG. 47 shows a schematic of an array of obstacles including nanoporous carbon nanotubes that enables simultaneous isolation of three different particle types ranging over three orders of magnitude in size—15 μm polystyrene beads, 2 μm biotin-coated particles, and 40 nm biotin-coated particles. The array of obstacles was formed as cylindrical micro-pillars (30 μm diameter, 100 μm height) that are spaced 5 μm apart from each other and that are wet-functionalized.

For example, functionalization is performed using Tween-20, an amphiphilic molecule that yields a monolayer coverage of the carbon nanotubes, which allows the naturally hydrophobic carbon nanotube surfaces to become hydrophyllic, and also suppresses non-specific binding (NSB) of proteins. First, 1,1 carbonyldiimidazole (CDI) was reacted with Tween 20 for 2 hours at 40° C., resulting in CDI-activated Tween. Pressure-driven injection of a solution of CDI-activated Tween (1 wt % in water) into the microchannel was used to functionalize the micropatterned carbon nanotube features, followed by flushing using deionized (DI) water. A second (optional) functionalization step was then performed to enable selective biological recognition of target species. The nanoporous features were functionalized using 1 hour incubation with CDI-activated Tween-20, followed by 1 hour incubation with 20 μm/ml NeutrAvidin in PBS, resulting in a covalent link between the avidin and the Tween-activated nanotubes.

The array combines micro- and nano-porosity to achieve simultaneous mechanical filtration and chemical bio-particle capture: the intra-pillar/element distance (5 μm) defines the microscale pores and the intra-carbon nanotube spacing (approximately 80 nm) defines the nanoscale porosity. Particles larger than the micro-scale pores cannot penetrate the array of functional element and are mechanically filtered at the front edge of the device, as is the case for the 15 μm polystyrene beads. Particles that are smaller than the micro-pores, yet larger than the average intra-carbon nanotube spacing, can enter the functional array, but not the micro-pillar elements, and are captured on the micropillars' surfaces using chemical affinity (2 μm beads). Finally, particles whose size is below the nano-pore threshold can flow through the carbon nanotube micro-pillars, and are isolated on the functional features using chemical bio-recognition (40 nm beads). This example demonstrates the ability of the carbon nanotube-enhanced microfluidic devices to enable simultaneous multi-physics, multi-scale bioparticle isolation on a single chip.

Devices as described herein can be adapted for implantation into a subject. For example, such a device can be adapted for placement in or near the circulatory system of a subject in order to be able to process blood samples. Such devices can be part of an implantable system as described herein that is fluidically coupled to the circulatory system of a subject, e.g., through tubing or an arteriovenous shunt. In some cases, systems as described herein that include implantable devices, e.g., disposable systems, can remove one or more analytes, components, or materials from the circulatory system. These systems can be adapted for continuous blood flow through the device.

A number of embodiments have been described herein. Nevertheless, it will be understood that various modifications can be made without departing from the spirit and scope. Accordingly, other embodiments are within the scope of the following claims.

What is claimed is:

1. A method of manipulating particles in a fluid sample, the method comprising:
   introducing a fluid sample comprising first particles having a first diameter, second particles having a second diameter that is less than the first diameter, and third particles having a third diameter that is less than the second diameter into a fluidic device comprising:
      a fluid path; and
      an array of obstacles disposed in the fluid path, each obstacle comprising a plurality of aligned nanostructures comprising nanotubes or nanorods or both nanotubes and nanorods, wherein gaps between the obstacles in the array permit particles having diameters less than the first diameter to flow through the gaps between obstacles, and wherein spaces between the nanostructures render each obstacle porous such that the porosity of the obstacles permits particles having diameters less than the second diameter to flow through the obstacle;
   flowing the fluid sample through the device;
   capturing the first particles with the array of obstacles;
   capturing at least some of the second particles within the array of obstacles at obstacle outer boundaries defined by a plurality of obstacles in the array; and
   capturing at least some of the third particles within one or more obstacles in the array.

2. The method of claim 1, wherein flowing the fluid sample through the device comprises flowing the fluid sample through the fluid path in a direction generally perpendicular to an average longitudinal axis of the aligned nanostructures.

3. The method of claim 1, wherein the porosity of each obstacle is substantially 99%.

4. The method of claim 1, wherein the plurality of nanostructures in each obstacle are functionalized with a binding moiety selected to bind to the third particles.

5. The method of claim 1, wherein the outer boundary of each obstacle is functionalized with a binding moiety selected to bind to the second particles on the outer surface.

6. The method of claim 1, wherein the gaps between the obstacles in the array form a network of gaps between the obstacles.

7. The method of claim 6, wherein an average gap size between the obstacles is between 20 and 100 microns in size.

8. A method of manipulating particles in a fluid sample, the method comprising:
   (a) introducing a fluid sample containing particles of a first type into a fluidic device comprising:
      (i) a fluid path; and
      (ii) one or more obstacles, the obstacles comprising a plurality of aligned nanostructures comprising nanotubes or nanorods or both nanotubes and nanorods, and having an obstacle outer boundary, the obstacle occupying a defined space in the fluid path; wherein the one or more obstacles are fixedly arranged within the fluid path such that some streamlines within the fluid path pass around the obstacle outer boundaries through gaps between the obstacles and some streamlines within the fluid path pass through the obstacle outer boundary and into a network of spaces within the obstacle between the nanostructures, and wherein the nanostructures within the obstacles alter a flow field near the obstacle outer boundaries of the obstacles compared to obstacles of the same defined space made of a material through which fluid does not flow; and
   (b) flowing the fluid sample through the fluid path, such that a smaller or greater number of the particles contacts the obstacles, relative to the number that would contact the obstacles of the same defined space if the obstacles were made of a material through which fluid does not flow.

9. The method of claim 8, wherein flowing the fluid sample through the fluid path comprises flowing the fluid sample at a flow rate that
   (i) maintains a geometry of the one or more obstacles such that a space occupied by a substantial number of the obstacles after the fluid sample is flowed through the fluid path is substantially the same as the defined space occupied by the same obstacle before the sample is flowed through the fluid path, and
   (ii) enables the capture of at least some of the particles of the first type in the fluid sample or the selective separation or concentration of at least some of the particles of the first type from the fluid sample or from particles of a second type.

10. The method of claim 8, wherein the one or more obstacles each comprise a total space of less than or equal to about 99 percent.

11. The method of claim 8, wherein the fluidic device comprises an array of multiple obstacles defining a network of gaps between the obstacles.

12. The method of claim 11, wherein an average gap size between the obstacles is between 20 and 100 microns in size.

13. The method of claim 8, wherein the one or more obstacles include at least on their obstacle outer boundary first binding moieties that specifically bind to the first type of particles.

14. The method of claim 8, wherein the one or more obstacles comprise two barriers including a gap between the two barriers that is larger than an average hydrodynamic size of the first type of particle, and wherein an average size of the spaces between the nanostructures within the barriers is smaller than an average hydrodynamic size of the first type of particle and larger than an average hydrodynamic size of the second type of particle, such that the fluidic device enables separation of the second type of particles from the first type of particle.

15. The method of claim 8, wherein the first type of particles comprise epithelial cells, cancer cells, bone marrow cells, fetal cells, progenitor cells, stem cells, foam cells, mesenchymal cells, immune system cells, endothelial cells, endometrial cells, connective tissue cells, trophoblasts, bacteria, fungi, platelets, or pathogens.

16. The method of claim 8, wherein the second type of particles comprise viruses, viral particles, exosomes, microvesicles, nucleic acids, proteins, lipids, and synthetic nanoparticles.

17. A fluidic device for manipulating particles, the device comprising:
   a substrate;
   a fluid path defined in the substrate; and
   an array of obstacles disposed within the fluid path, each obstacle comprising a plurality of aligned nanostructures comprising nanotubes or nanorods or both nanotubes and nanorods, wherein the array defines an array outer boundary that occupies a defined space in the fluid path, and wherein gaps between the obstacles in the array are configured to permit particles having a diameter less than a first diameter to flow through the gaps between the obstacles, and inhibit particles having a diameter greater than the first diameter from flowing through the gaps, wherein the obstacles have an obstacle outer boundary such that each obstacle occupies a defined space within the array, and wherein spaces between the nanostructures render the obstacles porous such that the porosity permits particles having a diameter less than a second diameter to flow through the obstacle and inhibit particles having a diameter greater than the second diameter from flowing through the obstacle, wherein the second diameter is less than the first diameter.

18. The fluidic device of claim 17, wherein first particles having a diameter greater than the first diameter are captured at the array outer surface, second particles having a diameter less than the first diameter and greater than the second diameter are captured within the array at one or more obstacle outer surfaces, and third particles having a diameter less than the second diameter are captured within one or more obstacles, when a fluid sample including the first particles, the second particles, and the third particles is flowed through the fluid path.

19. The device of claim 17, wherein the porosity is substantially 99%.

20. The device of claim 17, wherein the one or more obstacles include, at least on their outer surface, first binding moieties that specifically bind to the first particles, or second binding moieties that bind specifically to the second particles, or both.

* * * * *